(12) United States Patent
Swisher et al.

(10) Patent No.: US 7,976,498 B2
(45) Date of Patent: Jul. 12, 2011

(54) NEEDLE ASSEMBLY INCLUDING OBTURATOR WITH SAFETY RESET

(75) Inventors: David Rork Swisher, St. Charles, MO (US); Kenneth M. Breitweiser, Brighton, IL (US); Joel D. Wiesner, St. Peters, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 1110 days.

(21) Appl. No.: 11/741,529

(22) Filed: Apr. 27, 2007

(65) Prior Publication Data
US 2007/0219461 A1    Sep. 20, 2007

Related U.S. Application Data

(63) Continuation of application No. PCT/US2005/038965, filed on Oct. 27, 2005, which is a continuation of application No. 11/179,090, filed on Jul. 11, 2005, now Pat. No. 7,828,773, and a continuation of application No. 11/179,696, filed on Jul. 11, 2005, now Pat. No. 7,850,650, and a continuation of application No. 11/179,438, filed on Jul. 11, 2005, now Pat. No. 7,905,857.

(51) Int. Cl.
*A61M 5/00* (2006.01)

(52) U.S. Cl. ............. 604/110; 604/164.08; 600/567

(58) Field of Classification Search .......... 604/162, 604/164.01, 164.08, 110, 192; 600/562, 600/564, 567
See application file for complete search history.

(56) References Cited

U.S. PATENT DOCUMENTS

| | | | |
|---|---|---|---|
| 1,115,561 A | 11/1914 | Northey |
| 1,436,707 A | 11/1922 | Gaschke |
| 1,518,531 A | 12/1924 | Lung |
| 2,219,605 A | 10/1940 | Turkel |
| 2,854,976 A | 10/1958 | Heydrich |
| 3,254,533 A | 6/1966 | Tongret |
| 3,539,034 A | 11/1970 | Tafeen |
| 3,610,240 A | 10/1971 | Harautuneian |
| 3,681,991 A | 8/1972 | Eberly, Jr. |
| 3,729,998 A | 5/1973 | Mueller et al. |

(Continued)

FOREIGN PATENT DOCUMENTS
DE    3805567 A1    8/1989
(Continued)

OTHER PUBLICATIONS

Office action dated Jan. 11, 2010 from related U.S. Appl. No. 11/179,696, 8 pgs.

(Continued)

*Primary Examiner* — Nicholas D Lucchesi
*Assistant Examiner* — Laura A Bouchelle
(74) *Attorney, Agent, or Firm* — Lisa E. Winsor, Esq.

(57) ABSTRACT

A needle assembly is able to collect a sample of biological material in a needle of the assembly. The needle assembly has a safety shield capable of being moved on the needle assembly to cover a sharp tip of the needle assembly. The shield can be locked in place over the sharp tip by a locking mechanism. The assembly further includes an obturator that can be inserted into the needle to remove the sample from the needle. A reset member, which in some embodiments is associated with the obturator, is capable of operatively engaging the locking mechanism to release the locking mechanism and allow the shield to be moved away from the sharp tip.

6 Claims, 65 Drawing Sheets

U.S. PATENT DOCUMENTS

| | | |
|---|---|---|
| 3,822,598 A | 7/1974 | Hunter et al. |
| 3,884,230 A | 5/1975 | Wulff |
| 3,890,971 A | 6/1975 | Leeson et al. |
| 3,893,058 A | 7/1975 | Keith |
| 3,893,445 A | 7/1975 | Hofsess |
| 3,904,033 A | 9/1975 | Haerr |
| 3,915,003 A | 10/1975 | Adams |
| 3,946,613 A | 3/1976 | Silver |
| 3,976,070 A | 8/1976 | Dumont |
| 4,008,614 A | 2/1977 | Turner |
| 4,010,737 A | 3/1977 | Vilaghy et al. |
| 4,026,287 A | 5/1977 | Haller |
| 4,099,518 A | 7/1978 | Baylis et al. |
| D249,475 S | 9/1978 | Turner et al. |
| 4,112,762 A | 9/1978 | Turner et al. |
| 4,139,009 A | 2/1979 | Alvarez |
| 4,142,517 A | 3/1979 | Stavropoulos et al. |
| 4,143,853 A | 3/1979 | Abramson |
| 4,160,450 A | 7/1979 | Doherty |
| 4,163,446 A | 8/1979 | Jamshidi |
| 4,177,797 A | 12/1979 | Baylis et al. |
| 4,183,248 A | 1/1980 | West |
| D255,997 S | 7/1980 | Maeda |
| 4,211,214 A | 7/1980 | Chikashige |
| 4,256,119 A | 3/1981 | Gauthier |
| 4,258,713 A | 3/1981 | Wardlaw |
| 4,258,722 A | 3/1981 | Sessions et al. |
| 4,262,676 A | 4/1981 | Jamshidi |
| 4,266,543 A | 5/1981 | Blum |
| 4,266,555 A | 5/1981 | Jamshidi |
| 4,314,565 A | 2/1982 | Lee |
| 4,356,828 A | 11/1982 | Jamshidi |
| 4,392,859 A | 7/1983 | Dent |
| 4,403,617 A | 9/1983 | Tretinyak |
| 4,425,120 A | 1/1984 | Sampson |
| 4,438,884 A | 3/1984 | O'Brien et al. |
| 4,469,109 A | 9/1984 | Mehl |
| 4,482,348 A | 11/1984 | Dent |
| 4,487,209 A | 12/1984 | Mehl |
| 4,513,754 A | 4/1985 | Lee |
| 4,543,966 A | 10/1985 | Islam et al. |
| 4,572,365 A | 2/1986 | Bruno et al. |
| 4,573,976 A | 3/1986 | Sampson |
| 4,613,329 A | 9/1986 | Bodicky |
| 4,619,271 A | 10/1986 | Burger et al. |
| 4,630,616 A | 12/1986 | Tretinyak |
| 4,631,057 A | 12/1986 | Mitchell |
| 4,639,249 A | 1/1987 | Larson |
| 4,642,785 A | 2/1987 | Packard |
| 4,643,199 A | 2/1987 | Jennings |
| 4,643,200 A | 2/1987 | Jennings |
| 4,655,226 A | 4/1987 | Lee |
| 4,664,654 A | 5/1987 | Strauss |
| 4,676,783 A | 6/1987 | Jagger et al. |
| 4,681,567 A | 7/1987 | Masters |
| 4,693,708 A | 9/1987 | Wanderer |
| 4,695,274 A | 9/1987 | Fox |
| D292,493 S | 10/1987 | King |
| D292,494 S | 10/1987 | King |
| D293,215 S | 12/1987 | Bruno et al. |
| 4,723,943 A | 2/1988 | Spencer |
| 4,725,267 A | 2/1988 | Vaillancourt |
| 4,728,320 A | 3/1988 | Chen |
| 4,735,619 A | 4/1988 | Sperry |
| 4,737,144 A | 4/1988 | Choksi |
| 4,738,663 A | 4/1988 | Bogan |
| 4,741,627 A | 5/1988 | Fukui |
| 4,743,233 A | 5/1988 | Schneider |
| 4,747,831 A | 5/1988 | Kulli |
| 4,747,836 A | 5/1988 | Luther |
| 4,747,837 A | 5/1988 | Hauck |
| 4,752,290 A | 6/1988 | Schramm |
| 4,762,516 A | 8/1988 | Luther |
| 4,770,655 A | 9/1988 | Haber et al. |
| 4,772,272 A | 9/1988 | McFarland |
| 4,775,363 A | 10/1988 | Sandsdalen |
| 4,781,684 A | 11/1988 | Trenner |
| 4,781,692 A | 11/1988 | Jagger et al. |
| 4,785,826 A | 11/1988 | Ward |
| 4,790,329 A | 12/1988 | Simon |
| 4,790,827 A | 12/1988 | Haber et al. |
| 4,790,828 A | 12/1988 | Dombrowski |
| 4,793,363 A | 12/1988 | Ausherman et al. |
| 4,795,432 A | 1/1989 | Karczmer |
| 4,804,371 A | 2/1989 | Vaillancourt |
| 4,804,372 A | 2/1989 | Laico |
| 4,810,248 A | 3/1989 | Masters |
| 4,813,426 A | 3/1989 | Haber et al. |
| 4,816,022 A | 3/1989 | Poncy |
| D300,728 S | 4/1989 | Ross |
| 4,819,659 A | 4/1989 | Sitar |
| 4,820,275 A | 4/1989 | Haber et al. |
| 4,826,488 A | 5/1989 | Nelson |
| 4,826,490 A | 5/1989 | Byrne et al. |
| 4,826,491 A | 5/1989 | Schramm |
| 4,834,718 A | 5/1989 | McDonald |
| 4,838,280 A | 6/1989 | Haaga |
| 4,838,282 A | 6/1989 | Strasser et al. |
| 4,842,586 A | 6/1989 | Hogan |
| 4,846,809 A | 7/1989 | Sims |
| 4,900,307 A | 2/1990 | Kulli |
| 4,904,242 A | 2/1990 | Kulli |
| 4,906,235 A | 3/1990 | Roberts |
| 4,909,793 A | 3/1990 | Vining |
| 4,911,694 A | 3/1990 | Dolan |
| 4,911,706 A | 3/1990 | Levitt |
| 4,915,702 A | 4/1990 | Haber |
| D307,558 S | 5/1990 | Messina et al. |
| 4,922,602 A | 5/1990 | Mehl |
| 4,927,414 A | 5/1990 | Kulli |
| 4,929,241 A | 5/1990 | Kulli |
| 4,931,044 A | 6/1990 | Beiter |
| 4,935,013 A | 6/1990 | Haber et al. |
| 4,943,283 A | 7/1990 | Hogan |
| 4,944,725 A | 7/1990 | McDonald |
| 4,950,250 A | 8/1990 | Haber |
| 4,952,207 A | 8/1990 | Lemieux |
| 4,955,866 A | 9/1990 | Corey |
| 4,958,625 A | 9/1990 | Bates et al. |
| 4,960,412 A | 10/1990 | Fink |
| 4,964,854 A | 10/1990 | Luther |
| 4,966,587 A | 10/1990 | Baumgart |
| 4,969,554 A | 11/1990 | Sawaya |
| 4,978,344 A | 12/1990 | Dombrowski |
| 4,986,279 A | 1/1991 | O'Neill |
| 4,994,041 A | 2/1991 | Dombrowski |
| 5,005,585 A | 4/1991 | Mazza |
| 5,012,818 A | 5/1991 | Joishy |
| 5,013,304 A | 5/1991 | Russell et al. |
| 5,031,634 A | 7/1991 | Simon |
| 5,036,860 A | 8/1991 | Leigh et al. |
| 5,047,044 A | 9/1991 | Smith et al. |
| 5,049,136 A | 9/1991 | Johnson |
| 5,051,109 A | 9/1991 | Simon |
| 5,053,017 A | 10/1991 | Chamuel |
| 5,057,085 A | 10/1991 | Kopans |
| 5,059,180 A | 10/1991 | McLees |
| 5,085,648 A | 2/1992 | Purdy et al. |
| 5,092,851 A | 3/1992 | Ragner |
| 5,102,394 A | 4/1992 | Lasaitis |
| 5,108,374 A | 4/1992 | Lemieux |
| 5,126,090 A | 6/1992 | Egolf et al. |
| 5,127,916 A | 7/1992 | Spencer et al. |
| 5,133,727 A | 7/1992 | Bales et al. |
| 5,135,504 A | 8/1992 | McLees |
| 5,147,327 A | 9/1992 | Johnson |
| 5,154,703 A | 10/1992 | Bonaldo |
| 5,171,229 A | 12/1992 | McNeil et al. |
| 5,172,702 A | 12/1992 | Leigh et al. |
| 5,176,256 A | 1/1993 | Sawaya |
| 5,183,468 A | 2/1993 | McLees |
| 5,195,533 A | 3/1993 | Chin et al. |
| 5,195,985 A | 3/1993 | Hall |
| 5,213,115 A | 5/1993 | Zytkovicz et al. |
| 5,215,525 A | 6/1993 | Sturman |
| 5,215,528 A | 6/1993 | Purdy et al. |
| 5,215,533 A | 6/1993 | Robb |

| | | | | | |
|---|---|---|---|---|---|
| 5,217,438 A | 6/1993 | Davis | 5,538,009 A | 7/1996 | Byrne et al. |
| 5,228,451 A | 7/1993 | Bales et al. | 5,542,927 A | 8/1996 | Thorne et al. |
| 5,256,149 A | 10/1993 | Banik et al. | 5,549,565 A | 8/1996 | Ryan et al. |
| 5,257,632 A | 11/1993 | Turkel et al. | 5,549,708 A | 8/1996 | Thorne et al. |
| 5,279,306 A | 1/1994 | Mehl | 5,553,624 A | 9/1996 | Francese et al. |
| 5,279,563 A | 1/1994 | Brucker et al. | 5,558,651 A | 9/1996 | Crawford et al. |
| 5,279,591 A | 1/1994 | Simon | 5,562,629 A | 10/1996 | Haughton |
| 5,282,477 A | 2/1994 | Bauer | 5,562,633 A | 10/1996 | Wozencroft |
| 5,295,977 A | 3/1994 | Cohen et al. | 5,562,683 A | 10/1996 | Chan |
| 5,304,136 A | 4/1994 | Erskine | 5,569,217 A | 10/1996 | Luther |
| 5,312,359 A | 5/1994 | Wallace | 5,569,299 A | 10/1996 | Dill et al. |
| 5,314,406 A | 5/1994 | Arias et al. | 5,570,783 A | 11/1996 | Thorne et al. |
| 5,316,013 A | 5/1994 | Striebel, II et al. | 5,573,008 A | 11/1996 | Robinson et al. |
| 5,320,635 A | 6/1994 | Smith | 5,573,510 A | 11/1996 | Isaacson |
| 5,322,517 A | 6/1994 | Sircom et al. | 5,578,015 A | 11/1996 | Robb |
| 5,324,288 A | 6/1994 | Billings et al. | 5,584,809 A | 12/1996 | Gaba |
| 5,328,482 A | 7/1994 | Sircom et al. | 5,584,810 A | 12/1996 | Brimhall |
| 5,331,971 A | 7/1994 | Bales et al. | 5,584,818 A | 12/1996 | Morrison |
| 5,331,972 A | 7/1994 | Wadhwani et al. | 5,586,990 A | 12/1996 | Hahnen et al. |
| 5,334,158 A | 8/1994 | McLees | 5,591,202 A | 1/1997 | Slater et al. |
| 5,338,311 A | 8/1994 | Mahurkar | 5,595,186 A | 1/1997 | Rubinstein et al. |
| 5,338,314 A | 8/1994 | Ryan | 5,599,310 A | 2/1997 | Bogert |
| 5,341,816 A | 8/1994 | Allen | 5,601,536 A | 2/1997 | Crawford et al. |
| 5,344,408 A | 9/1994 | Partika | 5,601,585 A | 2/1997 | Banik et al. |
| 5,348,022 A | 9/1994 | Leigh et al. | 5,601,599 A | 2/1997 | Nunez |
| 5,348,544 A | 9/1994 | Sweeney et al. | 5,611,781 A | 3/1997 | Sircom et al. |
| 5,356,421 A | 10/1994 | Castro | 5,615,690 A | 4/1997 | Giurtino et al. |
| 5,357,974 A | 10/1994 | Baldridge | 5,616,135 A | 4/1997 | Thorne et al. |
| 5,368,045 A | 11/1994 | Clement et al. | 5,623,969 A | 4/1997 | Raines |
| 5,368,046 A | 11/1994 | Scarfone et al. | 5,624,459 A | 4/1997 | Kortenbach et al. |
| 5,370,623 A | 12/1994 | Kreamer | 5,630,506 A | 5/1997 | Thorne et al. |
| D354,921 S | 1/1995 | Narayanan | 5,630,837 A | 5/1997 | Crowley |
| 5,385,151 A | 1/1995 | Scarfone et al. | 5,632,555 A | 5/1997 | Gregory |
| 5,385,570 A | 1/1995 | Chin et al. | 5,634,473 A | 6/1997 | Goldenberg et al. |
| 5,389,104 A | 2/1995 | Hahnen et al. | 5,643,307 A | 7/1997 | Turkel et al. |
| 5,389,106 A | 2/1995 | Tower | 5,656,031 A | 8/1997 | Thorne et al. |
| 5,394,885 A | 3/1995 | Francese | 5,662,610 A | 9/1997 | Sircom |
| 5,395,375 A | 3/1995 | Turkel et al. | 5,666,965 A | 9/1997 | Bales et al. |
| 5,396,900 A | 3/1995 | Slater et al. | 5,669,883 A | 9/1997 | Scarfone et al. |
| 5,399,167 A | 3/1995 | Deniega | 5,672,161 A | 9/1997 | Allen |
| 5,403,283 A | 4/1995 | Luther | 5,679,907 A | 10/1997 | Ruck |
| 5,405,323 A | 4/1995 | Rogers et al. | 5,685,852 A | 11/1997 | Turkel et al. |
| 5,405,388 A | 4/1995 | Fox | 5,685,862 A | 11/1997 | Mahurkar |
| 5,409,461 A | 4/1995 | Steinman | 5,687,907 A | 11/1997 | Holden |
| 5,411,486 A | 5/1995 | Zadini | 5,690,619 A | 11/1997 | Erskine |
| 5,415,182 A | 5/1995 | Chin et al. | 5,693,022 A | 12/1997 | Haynes |
| 5,417,659 A | 5/1995 | Gaba | 5,693,031 A | 12/1997 | Ryan et al. |
| 5,417,709 A | 5/1995 | Slater | 5,695,467 A | 12/1997 | Miyata et al. |
| 5,419,766 A | 5/1995 | Chang et al. | 5,695,521 A | 12/1997 | Anderhub |
| 5,421,522 A | 6/1995 | Bowen | 5,697,904 A | 12/1997 | Raines et al. |
| 5,423,766 A | 6/1995 | Di Cesare | 5,697,907 A | 12/1997 | Gaba |
| 5,425,718 A | 6/1995 | Tay | 5,700,249 A | 12/1997 | Jenkins |
| 5,425,884 A | 6/1995 | Botz | 5,700,250 A | 12/1997 | Erskine |
| 5,429,138 A | 7/1995 | Jamshidi | 5,702,080 A | 12/1997 | Whittier et al. |
| 5,429,616 A | 7/1995 | Schaffer | 5,702,369 A | 12/1997 | Mercereau |
| 5,454,378 A | 10/1995 | Palmer et al. | 5,706,824 A | 1/1998 | Whittier |
| 5,456,267 A | 10/1995 | Stark | 5,707,392 A | 1/1998 | Kortenbach |
| 5,458,658 A | 10/1995 | Sircom | 5,713,368 A | 2/1998 | Leigh |
| 5,462,062 A | 10/1995 | Rubinstein et al. | 5,713,888 A | 2/1998 | Neuenfeldt et al. |
| 5,466,223 A | 11/1995 | Bressler et al. | 5,715,832 A | 2/1998 | Koblish et al. |
| 5,471,992 A | 12/1995 | Banik et al. | 5,718,688 A | 2/1998 | Wozencroft |
| 5,473,629 A | 12/1995 | Muramoto | 5,722,422 A | 3/1998 | Palmer et al. |
| 5,476,099 A | 12/1995 | Robinson et al. | 5,730,150 A | 3/1998 | Peppel et al. |
| 5,476,102 A | 12/1995 | Como et al. | 5,730,724 A | 3/1998 | Plishka et al. |
| 5,478,313 A | 12/1995 | White | 5,735,827 A | 4/1998 | Adwers |
| 5,480,385 A | 1/1996 | Thorne et al. | 5,738,660 A | 4/1998 | Luther |
| 5,482,054 A | 1/1996 | Slater et al. | 5,738,665 A | 4/1998 | Caizza |
| 5,487,734 A | 1/1996 | Thorne et al. | 5,746,753 A | 5/1998 | Sullivan et al. |
| 5,492,532 A | 2/1996 | Ryan et al. | 5,752,923 A | 5/1998 | Terwilliger |
| 5,501,675 A | 3/1996 | Erskine | D395,609 S | 6/1998 | Knieriem et al. |
| 5,507,296 A | 4/1996 | Bales et al. | 5,758,655 A | 6/1998 | Como Rodriguez et al. |
| 5,507,297 A | 4/1996 | Slater et al. | 5,776,157 A | 7/1998 | Thorne et al. |
| 5,507,298 A | 4/1996 | Schramm et al. | 5,795,336 A | 8/1998 | Romano et al. |
| 5,514,100 A | 5/1996 | Mahurkar | 5,807,275 A | 9/1998 | Jamshidi |
| 5,514,152 A | 5/1996 | Smith | 5,807,277 A | 9/1998 | Swaim |
| 5,522,398 A | 6/1996 | Goldenberg et al. | 5,810,744 A | 9/1998 | Chu et al. |
| 5,526,821 A | 6/1996 | Jamshidi | 5,817,069 A | 10/1998 | Arnett |
| 5,533,516 A | 7/1996 | Sahatjian | 5,823,970 A | 10/1998 | Terwilliger |
| 5,533,974 A | 7/1996 | Gaba | 5,823,971 A | 10/1998 | Robinson et al. |

| | | | | | |
|---|---|---|---|---|---|
| 5,823,997 A | 10/1998 | Thorne | 6,096,005 A | 8/2000 | Botich |
| 5,824,002 A | 10/1998 | Gentelia et al. | 6,102,920 A | 8/2000 | Sullivan et al. |
| D400,806 S | 11/1998 | Tillack | 6,106,484 A | 8/2000 | Terwilliger |
| D400,808 S | 11/1998 | Schwan | 6,110,128 A | 8/2000 | Andelin et al. |
| 5,836,917 A | 11/1998 | Thorne et al. | 6,110,129 A | 8/2000 | Terwilliger |
| 5,836,921 A | 11/1998 | Mahurkar | 6,110,176 A | 8/2000 | Shapira |
| 5,840,044 A | 11/1998 | Dassa et al. | RE036,885 E | 9/2000 | Blecher et al. |
| 5,843,001 A | 12/1998 | Goldenberg | 6,117,108 A | 9/2000 | Woehr et al. |
| 5,848,692 A | 12/1998 | Thorne et al. | 6,117,112 A | 9/2000 | Mahurkar |
| 5,853,393 A | 12/1998 | Bogert | 6,117,115 A | 9/2000 | Hill et al. |
| 5,860,955 A | 1/1999 | Wright et al. | 6,132,401 A | 10/2000 | Van Der Meyden |
| 5,865,806 A | 2/1999 | Howell | 6,135,110 A | 10/2000 | Roy |
| 5,871,453 A | 2/1999 | Banik et al. | 6,142,956 A | 11/2000 | Kortenbach et al. |
| 5,873,886 A | 2/1999 | Larsen et al. | 6,142,957 A | 11/2000 | Diamond et al. |
| 5,879,332 A | 3/1999 | Schwemberger et al. | 6,149,629 A | 11/2000 | Wilson et al. |
| 5,879,337 A | 3/1999 | Kuracina et al. | 6,171,284 B1 | 1/2001 | Kao |
| 5,879,338 A | 3/1999 | Mahurkar | 6,174,292 B1 | 1/2001 | Kortenbach et al. |
| 5,882,337 A | 3/1999 | Bogert et al. | 6,193,671 B1 | 2/2001 | Turturro et al. |
| 5,885,226 A | 3/1999 | Rubinstein et al. | 6,197,007 B1 | 3/2001 | Thorne et al. |
| 5,891,105 A | 4/1999 | Mahurkar | 6,203,527 B1 | 3/2001 | Zadini |
| 5,893,845 A | 4/1999 | Newby | 6,210,373 B1 | 4/2001 | Allmon |
| 5,893,876 A | 4/1999 | Turkel et al. | 6,217,556 B1 | 4/2001 | Ellingson et al. |
| 5,895,361 A | 4/1999 | Turturro | 6,221,029 B1 | 4/2001 | Mathis et al. |
| 5,897,507 A | 4/1999 | Kortenbach et al. | 6,221,047 B1 | 4/2001 | Greene et al. |
| 5,906,594 A | 5/1999 | Scarfone et al. | 6,224,569 B1 | 5/2001 | Brimhall |
| 5,910,130 A | 6/1999 | Caizza et al. | 6,224,576 B1 | 5/2001 | Thorne et al. |
| 5,910,132 A | 6/1999 | Schultz | 6,234,773 B1 | 5/2001 | Hill et al. |
| 5,911,705 A | 6/1999 | Howell | 6,254,575 B1 | 7/2001 | Thorne, Jr. et al. |
| 5,913,859 A | 6/1999 | Shapira | 6,261,242 B1 | 7/2001 | Roberts et al. |
| 5,916,715 A | 6/1999 | Fulford, Jr. et al. | 6,264,617 B1 | 7/2001 | Bales et al. |
| 5,928,162 A | 7/1999 | Giurtino et al. | D446,135 S | 8/2001 | Chen |
| 5,928,163 A | 7/1999 | Roberts et al. | 6,280,399 B1 | 8/2001 | Rossin et al. |
| 5,928,200 A | 7/1999 | Thorne et al. | 6,280,401 B1 | 8/2001 | Mahurkar |
| 5,935,109 A | 8/1999 | Donnan | 6,280,419 B1 | 8/2001 | Vojtasek |
| 5,947,930 A | 9/1999 | Schwemberger et al. | 6,280,420 B1 | 8/2001 | Ferguson et al. |
| 5,951,489 A | 9/1999 | Bauer | D448,314 S | 9/2001 | Chen |
| 5,951,525 A | 9/1999 | Thorne et al. | 6,283,925 B1 | 9/2001 | Terwilliger |
| 5,951,582 A | 9/1999 | Thorne et al. | 6,287,278 B1 | 9/2001 | Woehr et al. |
| 5,954,696 A | 9/1999 | Ryan | 6,293,700 B1 | 9/2001 | Lund et al. |
| 5,954,698 A | 9/1999 | Pike | 6,302,852 B1 | 10/2001 | Fleming, III et al. |
| 5,957,863 A | 9/1999 | Koblish et al. | 6,309,376 B1 | 10/2001 | Alesi |
| 5,957,887 A | 9/1999 | Osterlind et al. | 6,312,394 B1 | 11/2001 | Fleming, III |
| 5,957,892 A | 9/1999 | Thorne | 6,315,737 B1 | 11/2001 | Skinner |
| 5,961,526 A | 10/1999 | Chu et al. | 6,321,782 B1 | 11/2001 | Hollister |
| 5,961,534 A | 10/1999 | Banik et al. | 6,322,537 B1 | 11/2001 | Chang |
| 5,964,717 A | 10/1999 | Gottlieb et al. | 6,328,701 B1 | 12/2001 | Terwilliger |
| 5,967,490 A | 10/1999 | Pike | 6,328,713 B1 | 12/2001 | Hollister |
| 5,976,115 A | 11/1999 | Parris et al. | 6,334,857 B1 | 1/2002 | Hollister et al. |
| 5,979,840 A | 11/1999 | Hollister et al. | 6,336,915 B1 | 1/2002 | Scarfone et al. |
| 5,980,488 A | 11/1999 | Thorne | 6,340,351 B1 | 1/2002 | Goldenberg |
| 5,989,196 A | 11/1999 | Chu et al. | 6,358,252 B1 | 3/2002 | Shapira |
| 5,989,229 A | 11/1999 | Chiappetta | 6,358,265 B1 | 3/2002 | Thorne, Jr. et al. |
| 5,989,241 A | 11/1999 | Plishka et al. | 6,361,525 B2 | 3/2002 | Capes et al. |
| 5,993,426 A | 11/1999 | Hollister | 6,379,333 B1 | 4/2002 | Brimhall et al. |
| 6,000,846 A | 12/1999 | Gregory et al. | 6,379,338 B1 | 4/2002 | Garvin |
| 6,001,080 A | 12/1999 | Kuracina et al. | 6,383,144 B1 | 5/2002 | Mooney |
| 6,004,294 A | 12/1999 | Brimhall et al. | 6,406,459 B1 | 6/2002 | Allmon |
| 6,007,560 A | 12/1999 | Gottlieb et al. | 6,409,701 B1 | 6/2002 | Cohn et al. |
| 6,015,391 A | 1/2000 | Rishton et al. | 6,416,484 B1 | 7/2002 | Miller et al. |
| 6,022,324 A | 2/2000 | Skinner | 6,423,034 B2 | 7/2002 | Scarfone et al. |
| 6,024,708 A | 2/2000 | Bales et al. | 6,439,768 B1 | 8/2002 | Wu et al. |
| 6,024,727 A | 2/2000 | Thorne et al. | 6,443,910 B1 | 9/2002 | Krueger et al. |
| 6,033,369 A | 3/2000 | Goldenberg | 6,443,927 B1 | 9/2002 | Cook |
| 6,036,361 A | 3/2000 | Gregory et al. | 6,443,929 B1 | 9/2002 | Kuracina et al. |
| 6,036,675 A | 3/2000 | Thorne et al. | 6,478,751 B1 | 11/2002 | Krueger et al. |
| 6,047,729 A | 4/2000 | Hollister et al. | 6,485,468 B2 | 11/2002 | Vojtasek |
| 6,050,954 A | 4/2000 | Mittermeier | 6,485,473 B1 | 11/2002 | Lynn |
| 6,050,976 A | 4/2000 | Thorne et al. | 6,488,663 B1 | 12/2002 | Steg |
| 6,053,877 A | 4/2000 | Banik et al. | 6,500,129 B1 | 12/2002 | Mahurkar |
| 6,063,037 A | 5/2000 | Mittermeier et al. | 6,501,384 B2 | 12/2002 | Chapman |
| 6,063,040 A | 5/2000 | Owen et al. | 6,517,516 B1 | 2/2003 | Caizza |
| 6,071,284 A | 6/2000 | Fox | 6,519,569 B1 | 2/2003 | White et al. |
| 6,080,115 A | 6/2000 | Rubinstein | 6,520,938 B1 | 2/2003 | Funderburk |
| 6,083,176 A | 7/2000 | Terwilliger | 6,537,255 B1 | 3/2003 | Raines |
| 6,083,202 A | 7/2000 | Smith | 6,537,259 B1 | 3/2003 | Niermann |
| 6,086,563 A | 7/2000 | Moulton et al. | 6,544,194 B1 | 4/2003 | Kortenbach et al. |
| 6,090,078 A | 7/2000 | Erskine | 6,551,287 B2 | 4/2003 | Hollister |
| 6,090,108 A | 7/2000 | McBrayer et al. | 6,551,328 B2 | 4/2003 | Kortenbach |
| 6,095,967 A | 8/2000 | Black et al. | 6,554,778 B1 | 4/2003 | Fleming, III |

| | | |
|---|---|---|
| 6,569,125 B2 | 5/2003 | Jepson et al. |
| 6,575,919 B1 | 6/2003 | Reiley et al. |
| 6,582,402 B1 | 6/2003 | Erskine |
| 6,582,446 B1 | 6/2003 | Marchosky |
| 6,585,704 B2 | 7/2003 | Luther et al. |
| 6,592,556 B1 | 7/2003 | Thorne |
| 6,595,954 B1 | 7/2003 | Luther |
| 6,595,955 B2 | 7/2003 | Ferguson et al. |
| 6,613,018 B2 | 9/2003 | Bagga et al. |
| 6,616,604 B1 | 9/2003 | Bass et al. |
| 6,616,630 B1 | 9/2003 | Woehr et al. |
| 6,623,458 B2 | 9/2003 | Woehr et al. |
| 6,626,850 B1 | 9/2003 | Kupec et al. |
| D480,977 S | 10/2003 | Wawro et al. |
| D481,321 S | 10/2003 | Knieriem et al. |
| 6,629,959 B2 | 10/2003 | Kuracina et al. |
| 6,634,789 B2 | 10/2003 | Babkes |
| 6,635,033 B1 | 10/2003 | Hill et al. |
| 6,638,252 B2 | 10/2003 | Moulton |
| 6,638,254 B2 | 10/2003 | Nakagami |
| 6,641,562 B1 | 11/2003 | Peterson |
| 6,652,486 B2 | 11/2003 | Bialecki et al. |
| 6,652,490 B2 | 11/2003 | Howell |
| 6,663,592 B2 | 12/2003 | Rhad et al. |
| 6,673,047 B2 | 1/2004 | Crawford |
| 6,673,060 B1 | 1/2004 | Fleming, III |
| 6,682,510 B2 | 1/2004 | Niermann |
| 6,689,102 B2 | 2/2004 | Greene |
| 6,692,471 B2 | 2/2004 | Boudreaux |
| 6,695,814 B2 | 2/2004 | Greene et al. |
| 6,698,921 B2 | 3/2004 | Siefert |
| 6,699,221 B2 | 3/2004 | Vaillancourt |
| 6,702,786 B2 | 3/2004 | Olovson |
| 6,709,419 B2 | 3/2004 | Woehr |
| 6,719,732 B2 | 4/2004 | Courteix |
| 6,723,075 B2 | 4/2004 | Davey et al. |
| 6,727,805 B2 | 4/2004 | Hollister et al. |
| 6,730,043 B2 | 5/2004 | Krueger et al. |
| 6,731,216 B2 | 5/2004 | Ho et al. |
| 6,740,063 B2 | 5/2004 | Lynn |
| 6,749,576 B2 | 6/2004 | Bauer |
| 6,749,588 B1 | 6/2004 | Howell et al. |
| 6,749,595 B1 | 6/2004 | Murphy |
| 6,755,793 B2 | 6/2004 | Lamoureux et al. |
| 6,761,704 B2 | 7/2004 | Crawford |
| 6,761,706 B2 | 7/2004 | Vaillancourt |
| 6,764,567 B2 | 7/2004 | Sperko et al. |
| 6,767,336 B1 | 7/2004 | Kaplan |
| 6,770,050 B2 | 8/2004 | Epstein |
| 6,770,053 B2 | 8/2004 | Scarfone et al. |
| 6,796,962 B2 | 9/2004 | Ferguson et al. |
| 6,796,968 B2 | 9/2004 | Ferguson et al. |
| 6,798,348 B1 | 9/2004 | Wilker et al. |
| 6,811,308 B2 | 11/2004 | Chapman |
| 6,821,267 B2 | 11/2004 | Veillon, Jr. et al. |
| 6,827,488 B2 | 12/2004 | Knieriem et al. |
| 6,832,990 B2 | 12/2004 | Kortenbach et al. |
| 6,832,992 B2 | 12/2004 | Wilkinson |
| 6,839,651 B2 | 1/2005 | Lantz et al. |
| 6,846,314 B2 | 1/2005 | Shapira |
| 6,849,051 B2 | 2/2005 | Sramek et al. |
| 6,855,128 B2 | 2/2005 | Swenson |
| 6,855,130 B2 | 2/2005 | Saulenas et al. |
| 6,860,871 B2 | 3/2005 | Kuracina et al. |
| 6,875,183 B2 | 4/2005 | Cervi |
| 6,890,308 B2 | 5/2005 | Islam |
| 6,902,546 B2 | 6/2005 | Ferguson |
| 6,916,292 B2 | 7/2005 | Morawski et al. |
| 6,916,311 B2 | 7/2005 | Vojtasek |
| 6,916,314 B2 | 7/2005 | Schneider |
| 6,923,813 B2 | 8/2005 | Phillips et al. |
| 6,936,036 B2 | 8/2005 | Wilkinson |
| D512,506 S | 12/2005 | Layne et al. |
| D512,924 S | 12/2005 | Ikeda |
| 6,976,783 B2 | 12/2005 | Chen |
| 6,981,948 B2 | 1/2006 | Pellegrino et al. |
| 6,983,062 B2 | 1/2006 | Smith |
| 6,984,213 B2 | 1/2006 | Horner et al. |
| 6,984,216 B2 | 1/2006 | Sendijarevic et al. |
| 6,989,003 B2 | 1/2006 | Wing et al. |
| 7,001,363 B2 | 2/2006 | Ferguson et al. |
| 7,004,927 B2 | 2/2006 | Ferguson et al. |
| 7,008,402 B2 | 3/2006 | Ferguson et al. |
| 7,018,343 B2 | 3/2006 | Plishka |
| 7,021,824 B2 | 4/2006 | Wawro et al. |
| 7,033,324 B2 | 4/2006 | Giusti et al. |
| 7,036,984 B2 | 5/2006 | Penney et al. |
| 7,063,703 B2 | 6/2006 | Reo |
| 7,108,679 B2 | 9/2006 | Alchas |
| 7,112,191 B2 | 9/2006 | Daga |
| 7,118,552 B2 | 10/2006 | Shaw |
| 7,147,607 B2 | 12/2006 | Wang |
| 7,179,244 B2 | 2/2007 | Smith et al. |
| 7,204,812 B2 | 4/2007 | Wang |
| 7,207,973 B2 | 4/2007 | Barrelle |
| 7,226,434 B2 | 6/2007 | Carlyon et al. |
| 7,238,169 B2 | 7/2007 | Takagi et al. |
| 7,247,148 B2 | 7/2007 | Murashita |
| 7,255,475 B2 | 8/2007 | Quinn et al. |
| 7,264,613 B2 | 9/2007 | Woehr et al. |
| 7,300,420 B2 | 11/2007 | Doyle |
| 7,303,548 B2 | 12/2007 | Rhad et al. |
| 7,316,507 B2 | 1/2008 | Sisk et al. |
| 7,341,573 B2 | 3/2008 | Ferguson et al. |
| 7,357,784 B2 | 4/2008 | Ferguson |
| 7,377,908 B2 | 5/2008 | Buetikofer et al. |
| 7,413,562 B2 | 8/2008 | Ferguson et al. |
| 7,488,306 B2 | 2/2009 | Nguyen |
| 7,500,965 B2 | 3/2009 | Menzi et al. |
| 7,513,888 B2 | 4/2009 | Sircom |
| 2003/0002562 A1 | 1/2003 | Yerlikaya et al. |
| 2003/0114797 A1 | 6/2003 | Vaillancourt et al. |
| 2003/0144627 A1 | 7/2003 | Woehr et al. |
| 2003/0176810 A1 | 9/2003 | Maahs et al. |
| 2003/0220617 A1 | 11/2003 | Dickerson |
| 2004/0071182 A1 | 4/2004 | Quinn et al. |
| 2004/0077973 A1 | 4/2004 | Groenke et al. |
| 2004/0078007 A1 | 4/2004 | Nguyen |
| 2004/0092889 A1 | 5/2004 | Ferguson et al. |
| 2004/0153005 A1 | 8/2004 | Krueger |
| 2004/0162526 A1 | 8/2004 | Vaillancourt |
| 2004/0186434 A1 | 9/2004 | Harding et al. |
| 2004/0225260 A1 | 11/2004 | Villa et al. |
| 2004/0236288 A1 | 11/2004 | Howell et al. |
| 2005/0027263 A1 | 2/2005 | Woehr et al. |
| 2005/0043691 A1 | 2/2005 | Ferguson |
| 2005/0054987 A1 | 3/2005 | Perez et al. |
| 2005/0070850 A1 | 3/2005 | Albrecht |
| 2005/0070851 A1 | 3/2005 | Thompson et al. |
| 2005/0070855 A1 | 3/2005 | Ferguson et al. |
| 2005/0075609 A1 | 4/2005 | Latona |
| 2005/0113716 A1 | 5/2005 | Mueller, Jr. et al. |
| 2005/0119652 A1 | 6/2005 | Vetter et al. |
| 2005/0131345 A1 | 6/2005 | Miller |
| 2005/0137500 A1 | 6/2005 | Wingler |
| 2005/0165404 A1 | 7/2005 | Miller |
| 2005/0192536 A1 | 9/2005 | Takagi et al. |
| 2005/0267383 A1 | 12/2005 | Groenke et al. |
| 2005/0273057 A1 | 12/2005 | Popov |
| 2005/0277845 A1 | 12/2005 | Cooke et al. |
| 2005/0288605 A1 | 12/2005 | Pellegrino et al. |
| 2006/0052721 A1 | 3/2006 | Dunker et al. |
| 2006/0064101 A1 | 3/2006 | Arramon |
| 2006/0116603 A1 | 6/2006 | Shibazaki et al. |
| 2006/0178625 A1 | 8/2006 | Lim et al. |
| 2006/0189934 A1 | 8/2006 | Kuracina et al. |
| 2006/0189936 A1 | 8/2006 | Carlyon et al. |
| 2006/0200195 A1 | 9/2006 | Yang |
| 2006/0276772 A1 | 12/2006 | Moos et al. |
| 2007/0110122 A1 | 5/2007 | Sisk et al. |
| 2007/0116089 A1 | 5/2007 | Bisch et al. |
| 2008/0097345 A1 | 4/2008 | Ferguson |
| 2008/0112461 A1 | 5/2008 | Bisch et al. |
| 2008/0294065 A1 | 11/2008 | Waldhoff et al. |

FOREIGN PATENT DOCUMENTS

| | | |
|---|---|---|
| EP | 1358846 A1 | 11/2003 |
| JP | 6-241914 A | 9/1994 |

| | | | |
|---|---|---|---|
| WO | 96-22800 A1 | 8/1996 | |
| WO | 97-42989 A1 | 11/1997 | |
| WO | 2004060138 A2 | 7/2004 | |
| WO | 2004091687 A2 | 10/2004 | |
| WO | 2005009246 A1 | 2/2005 | |
| WO | 2005053774 A1 | 6/2005 | |
| WO | WO 2005053774 A1 * | 6/2005 | |
| WO | 2005060679 A2 | 7/2005 | |

OTHER PUBLICATIONS

Office action dated Feb. 3, 2010 from related U.S. Appl. No. 11/179,090, 5 pgs.

Office action dated Feb. 4, 2010 from related U.S. Appl. No. 11/179,438, 7 pgs.

* cited by examiner

NEEDLE ASSEMBLY INCLUDING OBTURATOR WITH SAFETY RESET

This application is a continuation of PCT/US2005/038965, filed Oct. 27, 2005 (expired) which was a continuation of U.S. patent application Ser. No. 11/179,090 now U.S. Pat. No. 7,828,773, Ser. No. 11/179,696 now U.S. Pat. No. 7,850,650 and Ser. No. 11/179,438 now U.S. Pat. No. 7,905,857, all filed Jul. 11, 2005.

BACKGROUND OF THE INVENTION

This invention relates generally to needle assemblies and more particularly to needle assemblies that have shields to cover sharp ends of needles.

Needle assemblies of the present invention have particular, although not exclusive application in the field of medicine and have needles with sharpened ends for use in piercing the skin to withdraw materials as needed. The needle is supported by some other structure that is used to manipulate the needle. The most common example is a syringe. However, some needle assemblies require the application of substantial force in use. One example of such a needle assembly is a bone marrow needle assembly that is used to penetrate cortical bone to reach the intramedullary canal for withdrawing liquid or a biopsy sample of bore marrow, or for infusing the canal with a selected material. Typically, the needle includes a cannula and a stylet that is received in the cannula and has a hard, sharp tip that can penetrate cortical bone. The tip projects out from the distal end of the cannula. The stylet can be withdrawn from the cannula after the needle penetrates the bone to the so that the hollow interior of the cannula can be used as a conduit for liquid or a receptacle to collect bone marrow.

In order to penetrate cortical bone, a substantial amount of force must be applied to the needle. For this reason, bone needle assemblies conventionally mount the needle in a handle that is sized and shaped so that the technician may comfortably grip the handle and apply the force necessary to penetrate the bone. The handle may comprise two handle members that can be selectively put together and separated for inserting the stylet into the cannula and removing the stylet from the cannula. A proximal handle member mounts the stylet and a distal handle member mounts the cannula. "Proximal" and "distal" refer to the relative location of the handle members to the technician when the needle assembly is in use. The proximal handle member is in contact with the palm of the technician's hand in use, and the distal handle member is on the opposite side of the proximal handle member from the palm.

Some needle assemblies, including bone needle assemblies, have associated safety mechanisms that shield the sharp tips of the needle components when they are not needed and after they have become contaminated with potentially hazardous biological material. The safety mechanism includes a shield and usually a mechanism for locking the shield in place over the sharpened tip. As a matter of convenience, and to enhance the probability that the safety feature will be used by a medical technician, the safety feature may be secured to the needle assembly. However, the safety feature must be retained out of the way when the needle assembly is being used, for example, to collect a liquid or solid sample from the intramedullary canal. The safety feature then must be released from its stowed position and moved to an operative position in which its shield covers the sharpened tip of the needle.

In cases where a sample (e.g., a bone marrow sample) is collected by the needle assembly, the sample has to be removed from the needle assembly. An obturator is a device including a long thin shaft, and in some cases includes a blunt tip, that can fit inside the cannula for pushing the sample of bone marrow out of the cannula. This can be done with the safety shield in position covering the sharp end of the cannula to protect the technician. In some cases it will be determined that the sample is not satisfactory and it will be necessary to obtain a second sample. It is not necessary to use a new needle assembly, because the needle assembly would be reused on the same patient. However, the shield is held in place over the tip of the needle assembly making it unusable for a collecting a second sample. Accordingly, there is a need for a needle assembly that can be easily reset for multiple uses, but which will not result in inadvertent release of the safety shield.

SUMMARY OF THE INVENTION

In one aspect of the present invention, a needle assembly generally comprises mounting structure and a needle mounted on the mounting structure and extending outwardly therefrom. The needle has a longitudinal axis, a sharp end and a central axial passageway. A safety shield associated with the needle comprises a tubular housing adapted for movement relative to the needle between a stowed position in which the tubular housing is spaced from the sharp end of the needle and a deployed position in which the tubular housing covers the sharp end. A locking mechanism of the safety shield is adapted to releasably lock the tubular housing in position covering the sharp end of the needle. An obturator includes a shaft sized and shaped for reception in the central axial passageway of the needle. A reset member operatively connected to the shaft is selectively operatively engageable with the locking mechanism of the safety shield for releasing the locking mechanism to permit the tubular housing to be move away from the sharp end of the needle.

In another aspect of the present invention, an obturator may be used with a needle assembly to remove a sample of biological material collected in the needle assembly. The needle assembly includes a safety shield having a locking mechanism capable of locking the safety shield in place on the needle assembly. The obturator generally comprises a grip for holding and manipulating the obturator and a shaft extending from the grip. The shaft is sized and shaped for reception in a central axial passageway of the needle assembly for pushing the sample out of the central axial passageway. A reset member operatively connected to the grip and adapted for engagement with the locking mechanism of the safety shield for releasing the locking mechanism.

In yet another aspect of the present invention, a method for obtaining a sample of biological material from a subject using a needle assembly and resetting the needle assembly for subsequent use, generally comprises the step of pushing a needle of the needle assembly having a central axial passageway into the subject to collect a sample of biological material from the subject in the central axial passageway. A shaft of an obturator is inserted into the central axial passageway of the needle to push the sample out of the central axial passageway. The obturator is manipulated to bring a reset member on the obturator into engagement with a locking mechanism of a shield on the needle assembly to release the locking mechanism. The shield is then moved.

In a further aspect of the present invention, a needle assembly generally comprises mounting structure and a needle mounted on the mounting structure and extending outwardly therefrom. The needle has a longitudinal axis, a sharp end and a central axial passageway. A safety shield associated with the needle comprises a tubular housing adapted for movement relative to the needle between a stowed position in which the tubular housing is spaced from the sharp end of the needle and a deployed position in which the tubular housing covers the sharp end. A locking mechanism is adapted to releasably lock the tubular housing in position covering the sharp end of the needle. The tubular housing has distal and proximal ends and at least one peripheral slot extending radially inwardly from the periphery and axially along the housing from the distal end of the housing. A reset key adapted to actuate release of the locking mechanism to permit the shield to be moved relative to the needle comprises a support and at least one rib on the support sized and arranged for reception in the peripheral slot of the tubular housing for entering the tubular housing to actuate release of the locking mechanism.

In yet a further aspect of the present invention, a reset key for use in releasing a locking mechanism of a safety shield covering a sharp tip of a needle for movement of the safety shield relative to the needle generally comprises a support defining a central open space sized and shaped for receiving at least a portion of the safety shield. Ribs mounted on the support and located at positions spaced circumferentially of each other generally around the perimeter of the central open space are shaped and arranged for reception in slots on the safety shield when the safety shield is received in the central open space for actuating release of the locking mechanism.

In still a further aspect of the present invention, a reset key for use in releasing a locking mechanism of a safety shield covering a sharp tip of a needle for movement of the safety shield relative to the needle generally comprises a shroud sized and shaped for receiving at least a majority of the safety shield therein. A reset member associated with the shroud can actuate release of the locking mechanism when the safety shield is received in the shroud.

In another aspect of the present invention, a needle assembly generally comprises mounting structure and a needle mounted on the mounting structure and extending outwardly therefrom. The needle has a longitudinal axis, a sharp end, and a central axial passageway. A safety shield associated with the needle comprises a tubular housing adapted for movement relative to the needle between a stowed position in which the tubular housing is spaced from the sharp end of the needle and a deployed position in which the tubular housing covers the sharp end. A locking mechanism is adapted to releasably lock the tubular housing in position covering the sharp end of the needle. An unlocking mechanism is adapted to engage the locking mechanism to unlock the tubular housing from the needle. An obturator includes a shaft sized and shaped for reception in the central axial passageway of the needle. A reset member operatively connects to the shaft and selectively engages the unlocking mechanism of the safety shield for moving the unlocking mechanism into selective engagement with the locking mechanism for releasing the locking mechanism to permit the tubular housing to move away from the sharp end of the needle.

In yet another aspect of the present invention, a resettable needle safety shield for use in selectively shielding and unshielding a sharp tip of a needle generally comprises a housing sized and shaped for substantially surrounding the sharp needle tip to hinder access to the sharp tip and a locking mechanism associated with the housing. The locking mechanism is adapted to lock the housing in position substantially surrounding the sharp needle tip. An unlocking mechanism is associated with the housing for movement relative to the housing between a first position in which the locking mechanism is free to lock the housing in position relative to the sharp needle tip and a second position in which the unlocking mechanism releases the locking mechanism to permit movement of the housing relative to the needle.

In still another aspect of the present invention, a resettable needle safety shield for use in selectively shielding and unshielding a sharp tip of a needle generally comprises a housing sized and shaped for substantially surrounding the sharp needle tip to hinder access to the sharp tip and a locking mechanism associated with the housing. The locking mechanism is adapted to lock the housing in position substantially surrounding the sharp needle tip. The housing includes an end wall having at least one hole therein arranged in relation to the locking mechanism for receiving structure through the end wall for use in releasing the locking mechanism.

In a further aspect of the present invention, an obturator for use with a needle assembly to remove a sample of biological material collected in a hollow needle of the needle assembly generally comprises a grip for holding and manipulating the obturator. A shaft extending from the grip is sized and shaped for reception in a central axial passageway of the needle assembly for pushing the sample out of the central axial passageway. A shield is slidably supported on the shaft for engaging and shielding a sharp end of the hollow needle when the obturator shaft is being inserted into the needle to remove the sample.

In yet a further aspect of the present invention, a needle assembly generally comprises a mounting structure and a needle mounted on the mounting structure and extending outwardly therefrom. The needle has a longitudinal axis, a sharp end and a central axial passageway. A safety shield is associated with the needle and comprises a tubular housing having an open end. The tubular housing is adapted for movement relative to the needle between a stowed position in which the tubular housing is spaced from the sharp end of the needle and a deployed position in which the tubular housing covers the sharp end. A locking mechanism is adapted to releasably lock the tubular housing in position covering the sharp end of the needle. A reset member is selectively operatively engageable with the locking mechanism of the safety shield for releasing the locking mechanism to permit the tubular housing to be move away from the sharp end of the needle. The safety shield further comprises a resilient membrane substantially covering the open end of the tubular housing. The membrane is resiliently deformable upon engagement with the reset member to permit the reset member to move into operative engagement with the locking mechanism for releasing the locking mechanism.

In another aspect of the present invention, a needle assembly generally comprises mounting structure and a needle mounted on the mounting structure and extending outwardly therefrom. The needle has a longitudinal axis, a sharp end and a central axial passageway. A safety shield associated with the needle comprises a tubular housing having an open end. The tubular housing is adapted for movement relative to the needle between a stowed position in which the tubular housing is spaced from the sharp end of the needle and a deployed position in which the tubular housing covers the sharp end. A locking mechanism is adapted to releasably lock the tubular housing in position covering the sharp end of the needle. A reset member supported on the safety shield for sliding movement relative to the safety shield generally parallel to a outer surface of the safety shield, the resent member being selectively operatively engageable with the locking mechanism of the safety shield for releasing the locking mechanism to permit the tubular housing to be move away from the sharp end of the needle.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
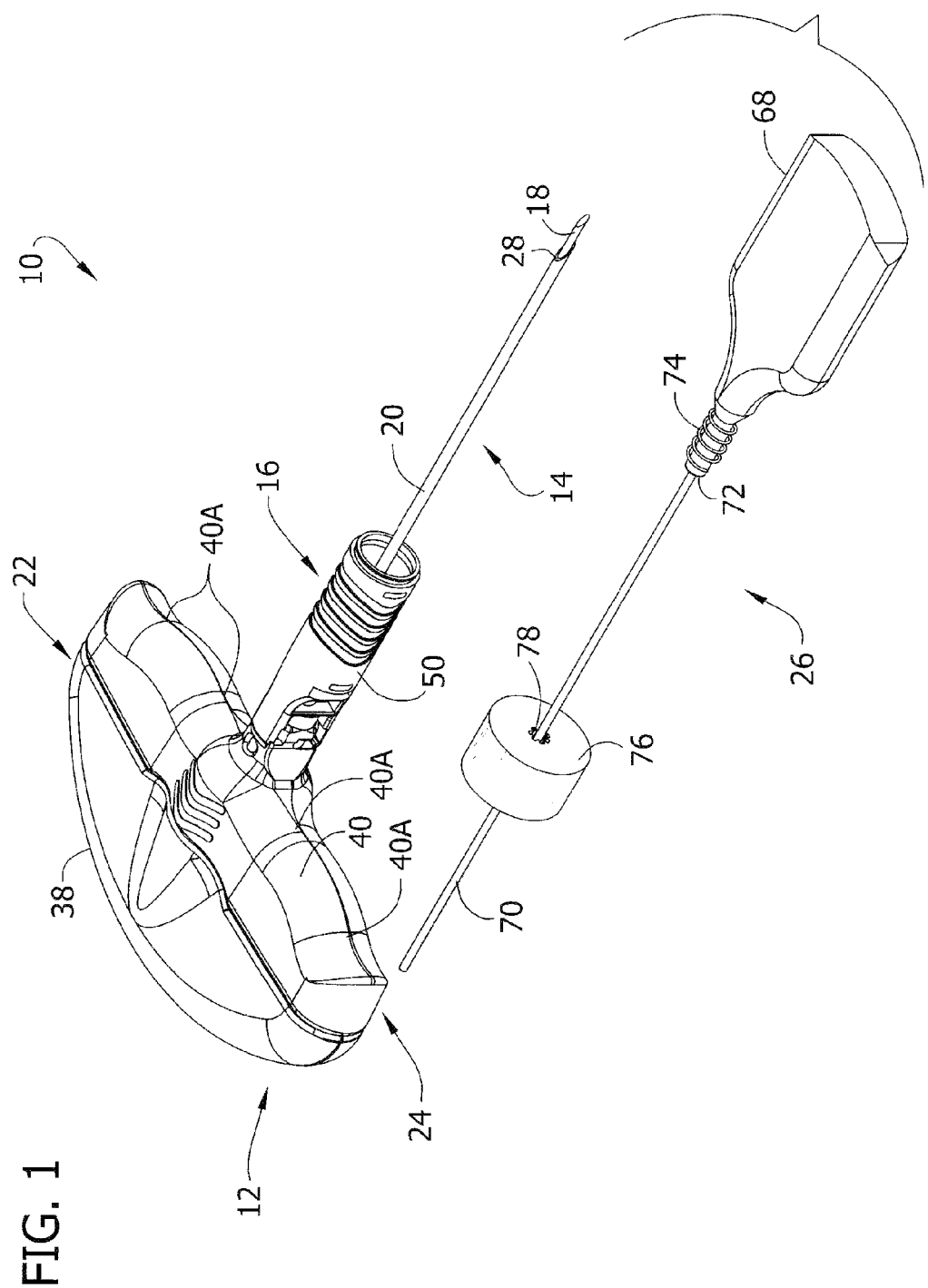
FIG. 1 is a perspective of a bone needle assembly including an obturator.

Referring now to the drawings and in particular to FIG. 1, a medical instrument constructed according to the principles of the present invention is shown in the form of a bone needle assembly, generally indicated at 10. The bone needle assembly includes a handle 12 (broadly, "mounting structure"), a needle 14 and a cannula safety shield 16, all reference numbers indicating their subjects generally. The needle 14 includes a stylet 18 and a cannula 20 that can receive the stylet. The handle 12 includes a first or proximal handle member (indicated generally at 22) mounting the stylet 18, and a second or distal handle member (indicated generally at 24) mounting the cannula 20. It will be understood that a needle could include only a single component part, or more than two parts within the scope of the present invention. Similarly, a handle could be a single part or more than two parts. The mounting structure for the needle 14 can be other than a handle without departing from the present invention. The needle assembly 10 further includes an obturator 26 (described more fully below) that may be used to remove a sample captured in the cannula 20.

The cannula 20 has a central axial passage extending the length of the cannula and opening at both ends of the cannula. A distal tip 28 of the cannula 20 is beveled and sharpened. A proximal end portion of the cannula 20 is received in the distal handle member 24. The stylet 18 is solid and includes a sharp distal tip, and a proximal end portion received in the proximal handle member 22. The stylet 18 can be inserted through the axial passage opening in the proximal end portion of the cannula 20 and received entirely through the axial passage of the cannula so that its sharp distal tip projects axially outward from the distal tip 28 of the cannula. The stylet 18 provides the tool for penetrating the cortical bone, and can be removed from the cannula 20 once the intramedullary canal is accessed by the needle 14.

The handle 12 formed by the proximal and distal handle members 22, 24 has an ergonomic shape that can be comfortably received in a medical technician's hand, and allows the technician to easily control the needle assembly 10 as he or she applies the substantial forces needed to penetrate the bone. More specifically, the top or proximal surface 38 of the proximal handle member 22 is rounded in conformance with the shape of the palm of the hand. The bottom or distal surface 40 of the distal handle member 24 is also rounded, but is undulating in shape thereby forming finger wells 40A for receiving the technician's fingers. The form of the handle can be other than described herein without departing from the scope of the present invention. The proximal and distal handle members 22, 24 can be connected together in a suitable manner when the stylet 18 is received in the cannula 20, so that the handle 12 acts essentially as a single piece when used to drive the needle 14 through a patient's skin and into the bone. The proximal and distal handle members 22, 24 can be disconnected and moved apart for removing the stylet 18 from the cannula 20.

The cannula safety shield 16 may be moved to cover the distal tip 28 of the cannula 20 after the needle assembly 10 has been used. The safety shield 16 includes a generally tubular housing 50 and an internal locking mechanism (generally indicated at 52 in FIG. 2) capable of releasably locking the tubular housing in position covering the distal tip 28 of the cannula 20. The tubular housing 50 may have any shape that is suitable for hindering access to the sharp tip 28. The tubular housing 50 need not be solid or circular in cross section within the scope of the present invention. The tubular housing 50 and handle 12 may include structure to secure the tubular housing in a retracted position adjacent the handle when not needed. An example of such structure is shown in co-assigned U.S. application Ser. No. 11/146,173, filed Jun 6, 2005, the disclosure of which is incorporated herein by reference.

The locking mechanism 52 inside the safety shield 16 comprises a canting member including a base 56 having a hole and a pair of arms 60 (only one is shown) extending generally axially from the base. The arms 60 are connected together by a U-shaped member 62 at their ends and each has an upwardly (as oriented in the figures) bent tab 64 (only one is shown) projecting axially outward from the end. Before the locking mechanism 52 is activated to lock the tubular housing 50 in position, the ends of the arms 60 ride on the exterior surface of the cannula 20. This holds the canting member so that the base 56 is orthogonal so the longitudinal axis of the cannula 20 and the base can move along the cannula (with the safety shield 16), with the cannula sliding unimpeded through the hole in the base. Once the ends of the arms 60 pass the distal tip 28 of the cannula 20, the locking mechanism 52 is weighted so that the ends of the arms move in a generally radial direction toward an opposite side of the longitudinal axis of the needle 14. This causes the base 56 of the canting member to cant relative to the axis of the needle 14 so that the hole in the base is no longer orthogonal to the axis of the cannula. As a result, the base 56 at the edge of the hole grippingly engages the cannula 20 to lock the safety shield 16 in place. It will be understood that a locking mechanism could take on other forms than shown and described without departing from the scope of the present invention. Moreover, the canting member may take on other configurations within the scope of the present invention.

The needle assembly 10 is driven into the bone by grasping the handle 12 and pushing the stylet 18 through the skin, underlying tissue and cortical bone. Once this penetration has been achieved, the stylet 18 is no longer required. The proximal handle member 22 is disconnected from the distal handle member 24 and moved axially away from the distal handle member so that the stylet 18 slides out of the central axial passageway of the cannula 20 while the cannula remains in the bone. In order to collect a sample of bone marrow, the distal handle member is advanced further into the bone. The sharp tip 28 of the cannula 20 cuts into the bone marrow and a sample is received in the central axial passageway of the cannula. The cannula 20 can then be withdrawn from the patient by pulling on the distal handle member 24. The sample remains lodged in the central axial passageway of the cannula 20 near the sharp tip 28. It will be understood that a needle assembly may be used to collect a sample other than of bone marrow within the scope of the present invention.

Figure 2:
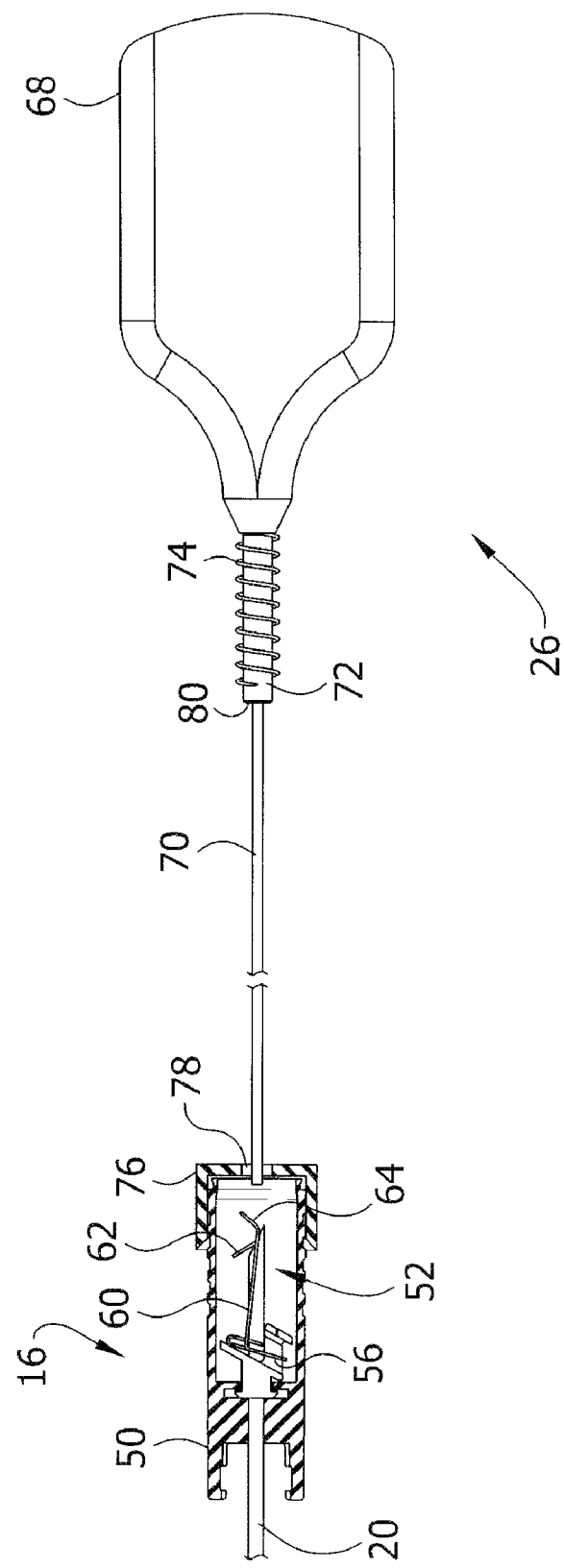
FIG. 2 is a fragmentary partial section of the needle assembly with the obturator engaging a safety shield of the needle assembly and parts broken away to show internal construction.

The obturator 26 is used to remove a lodged sample of bone marrow that has been collected in the central axial passageway of cannula 20. The obturator 26 includes a grip 68 and a long, thin shaft 70 extending from the grip that is sized to be received in the central axial passageway of the cannula 20 in generally close fitting relation therein. The grip 68 is sized and shaped to be grasped by a user for manipulating the obturator 26, as will be described. A tubular reset member 72 extends from the grip 68 in the same direction as the shaft 70 and is generally coaxial with the shaft in the illustrated embodiment. The reset member 72 has an open end 73 opposite the grip 68. A coil compression spring 74 surrounds the reset member 72 and is operatively secured to the grip 68. An annular aligning device in the form of a cap 76 is slidably mounted on the free end of the shaft 70 (opposite the grip 68), and is capable of centering the shaft relative to the tubular housing 50. In one version (not shown) the cap 76 may be attached to the spring 74 for use in retaining the cap on the obturator 26. The cap 76 has an opening 78 having an annular, resilient membrane that can engage and center the shaft 70 in the opening. As shown in FIG. 2, the cap receives a distal end portion of the tubular housing 50 in generally close-fitting relation so that the shaft 70 of the obturator 26 is aligned with the central axial passageway of the cannula 20. The cap 76 and tubular housing 50 may be formed so that the cap has a releasable, snap-acting attachment with the housing when engaging the housing. However, the attachment may be omitted or take on other forms without departing from the scope of the present invention.

Figure 3:
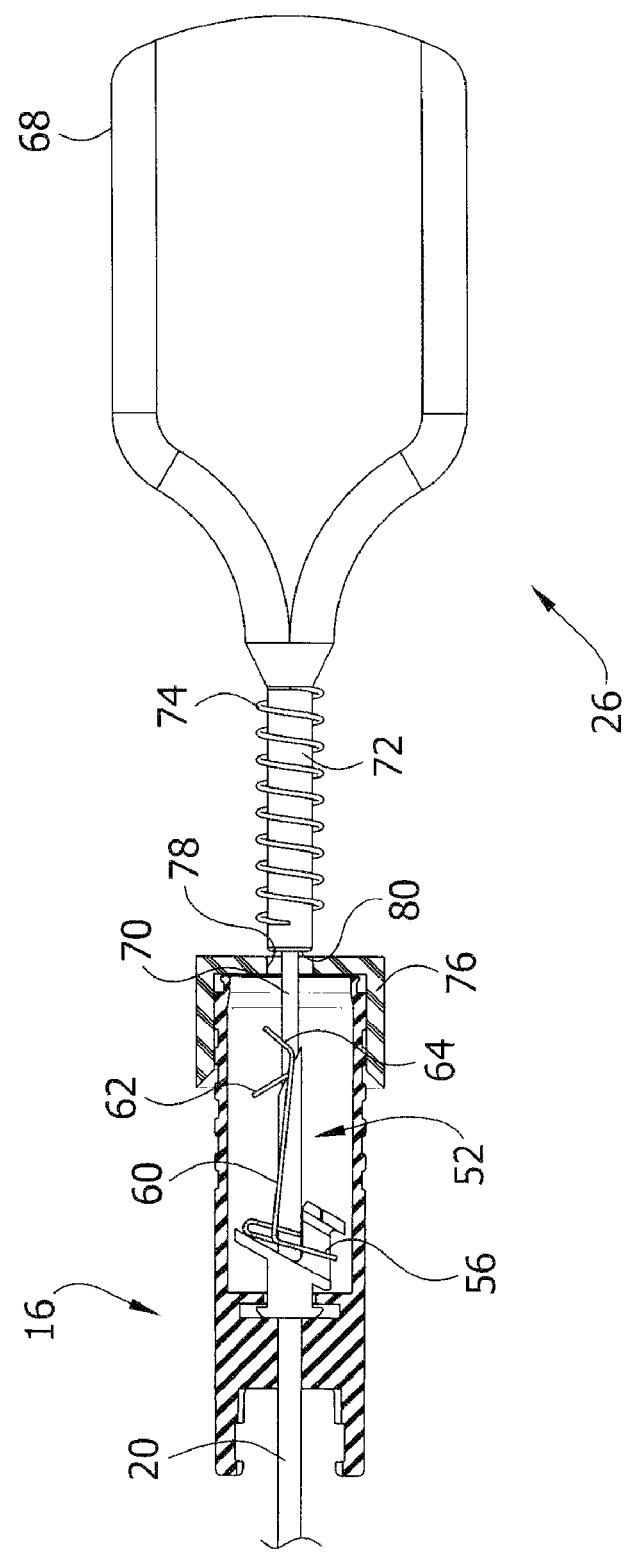
FIG. 3 is the fragmentary elevation of FIG. 2 but showing the obturator inserted to a position in which a sample collected by the needle assembly is pushed out of the needle assembly.

FIG. 2 illustrates the initial position of the obturator 26 with the cap 76 engaging the proximal end of the tubular housing 50. The free end of the shaft 70 has not yet entered the central axial passageway of the cannula 20. The grip 68 is pushed to advance the shaft 70 into the central axial passageway, which pushes the sample toward the proximal end of the central axial passageway. As shown in FIG. 3, the shaft 70 is advanced until it protrudes out of the proximal end of the central axial passageway, thereby pushing the sample (not shown) out of the cannula 20 where it can be collected in a Petri dish or other suitable container. As the shaft 70 is advanced, it slides through the cap 76. The locking mechanism 52 remains engaged so that the safety shield 16 does not move. In the position shown in FIG. 3, the spring 74 surrounding the reset member 72 engages the cap 76, but is not substantially deflected by this engagement. Thus, the technician experiences slight resistance to further inward movement of the shaft 70 into the central axial passageway of the cannula 20.

The technician may observe the sample ejected from the central axial passageway of the cannula 20. If it is determined that the sample is satisfactory, the obturator 26 can be pulled so that the shaft 70 slides back through and out of the cannula 20. The needle assembly 10 can be discarded, or possibly but less likely, cleaned and sterilized for a subsequent use. However, if the sample is not satisfactory it will be necessary to obtain a second sample. This can be done using the same needle assembly 10, but the tubular housing 50 is locked in place by the locking mechanism 52 over the sharp tip 28 of the cannula 20. The tubular housing 50 needs to be moved away from the tip 28 before the needle assembly 10 can be used to obtain a second sample.

Figure 4:
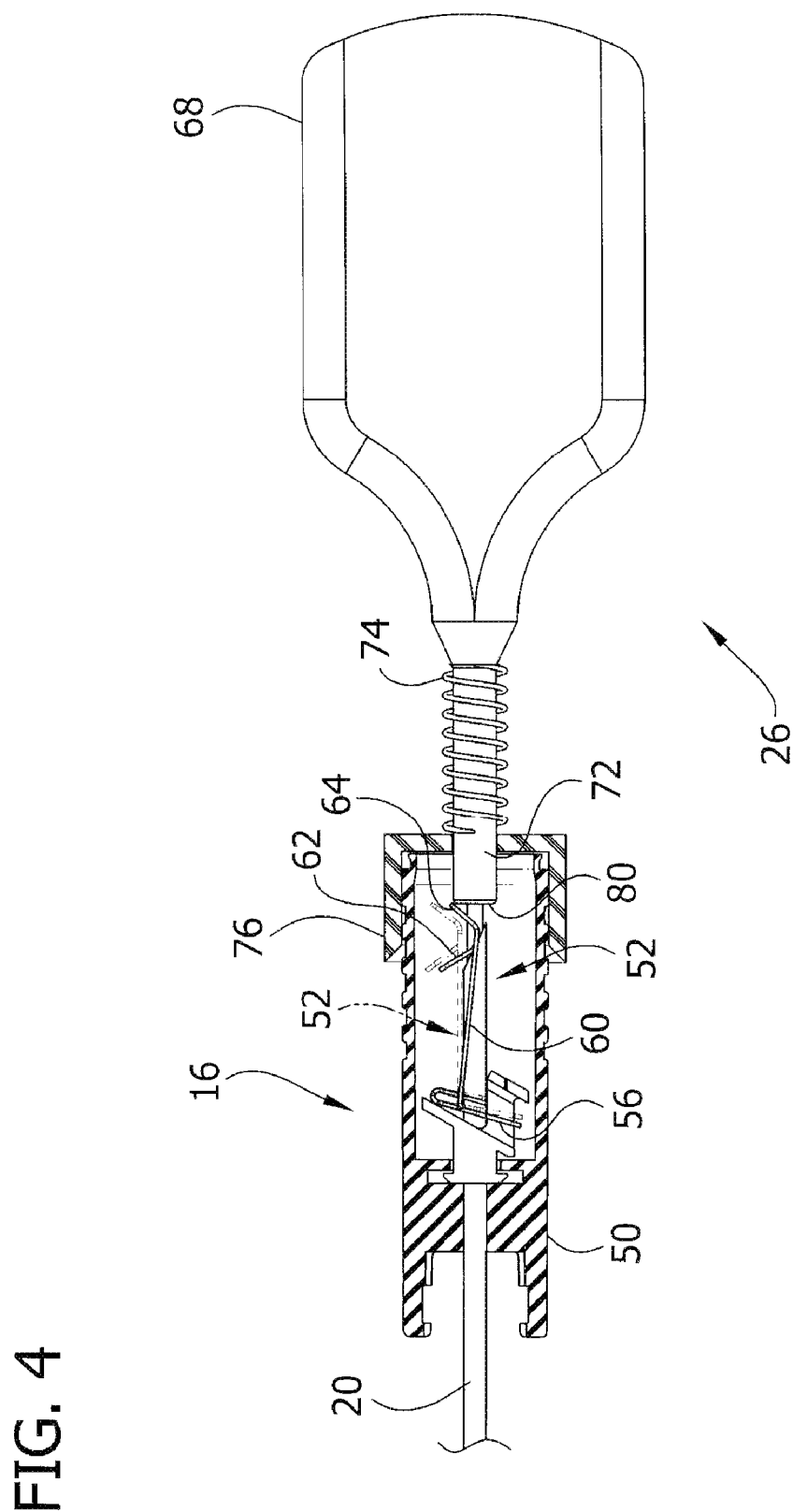
FIG. 4 is the fragmentary elevation of FIG. 2 but showing use of the obturator to reset a locking mechanism of the safety shield.
Figure 5:
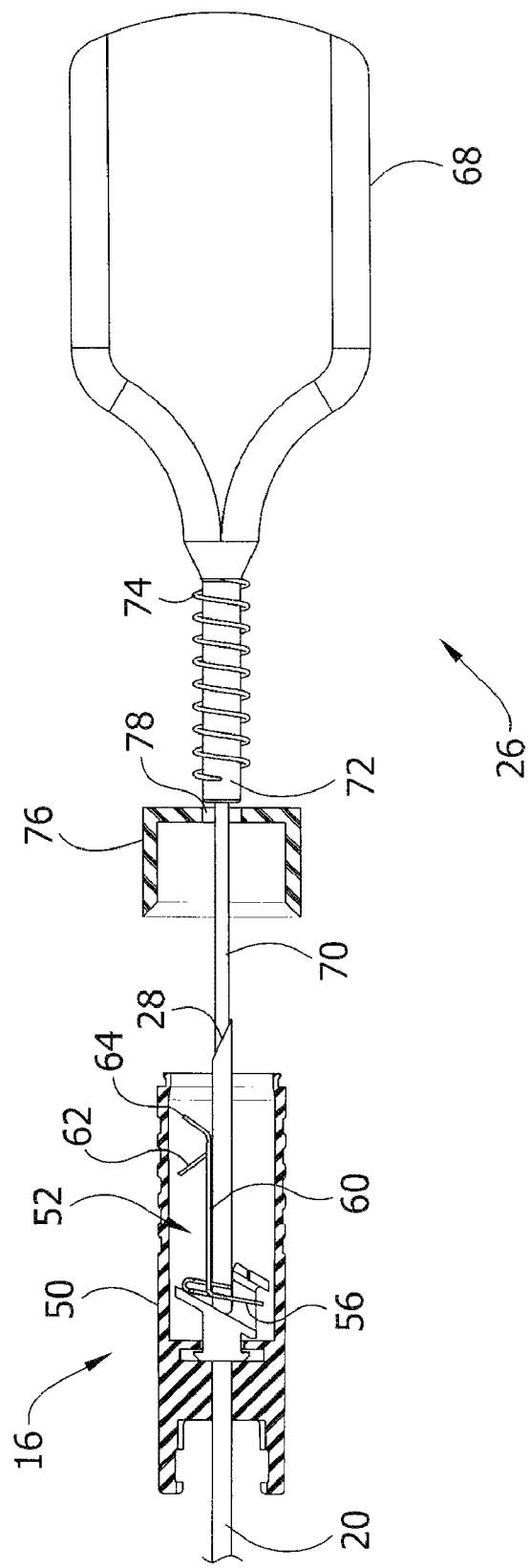
FIG. 5 is the fragmentary elevation of FIG. 2 but showing the safety shield being withdrawn from a sharp end of the needle assembly after release of the locking mechanism.
Figure 6:
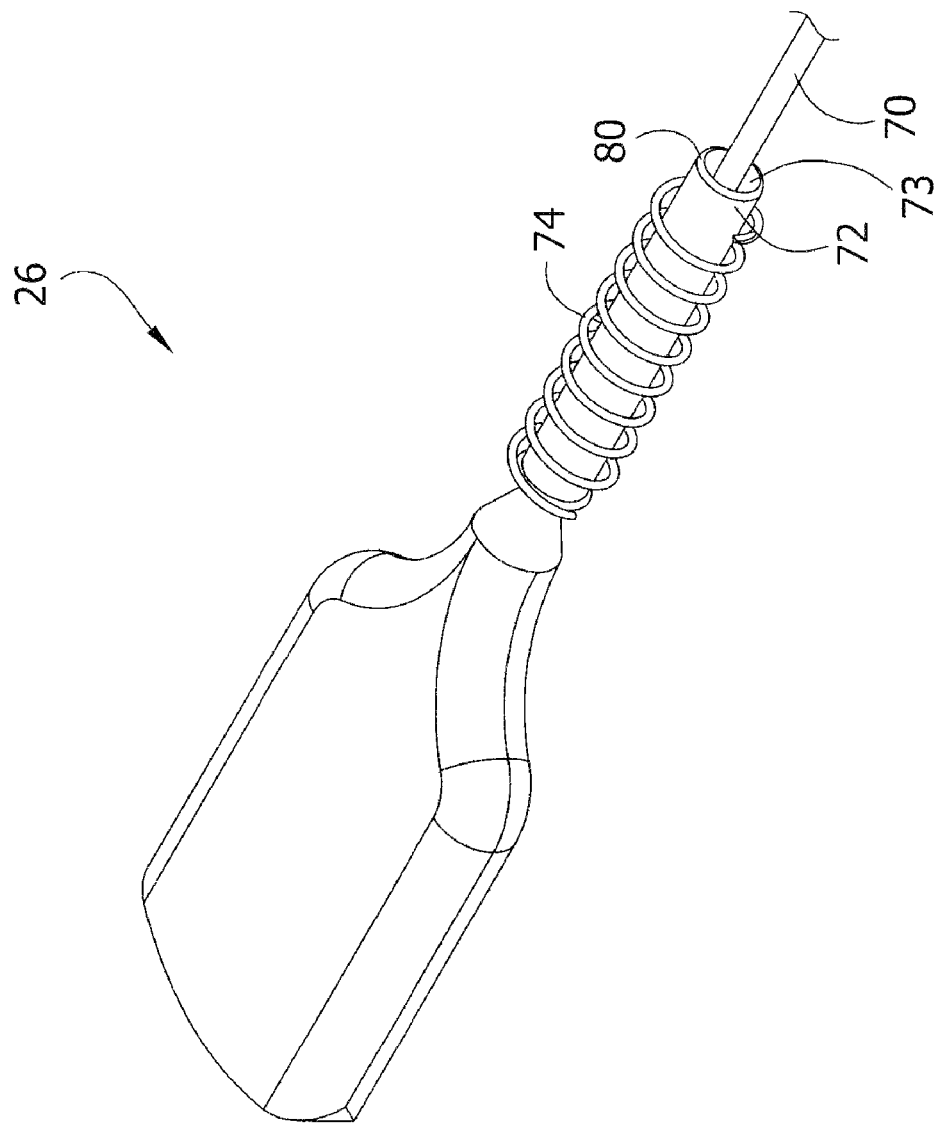
FIG. 6 is an end elevation of the obturator.
Figure 7:
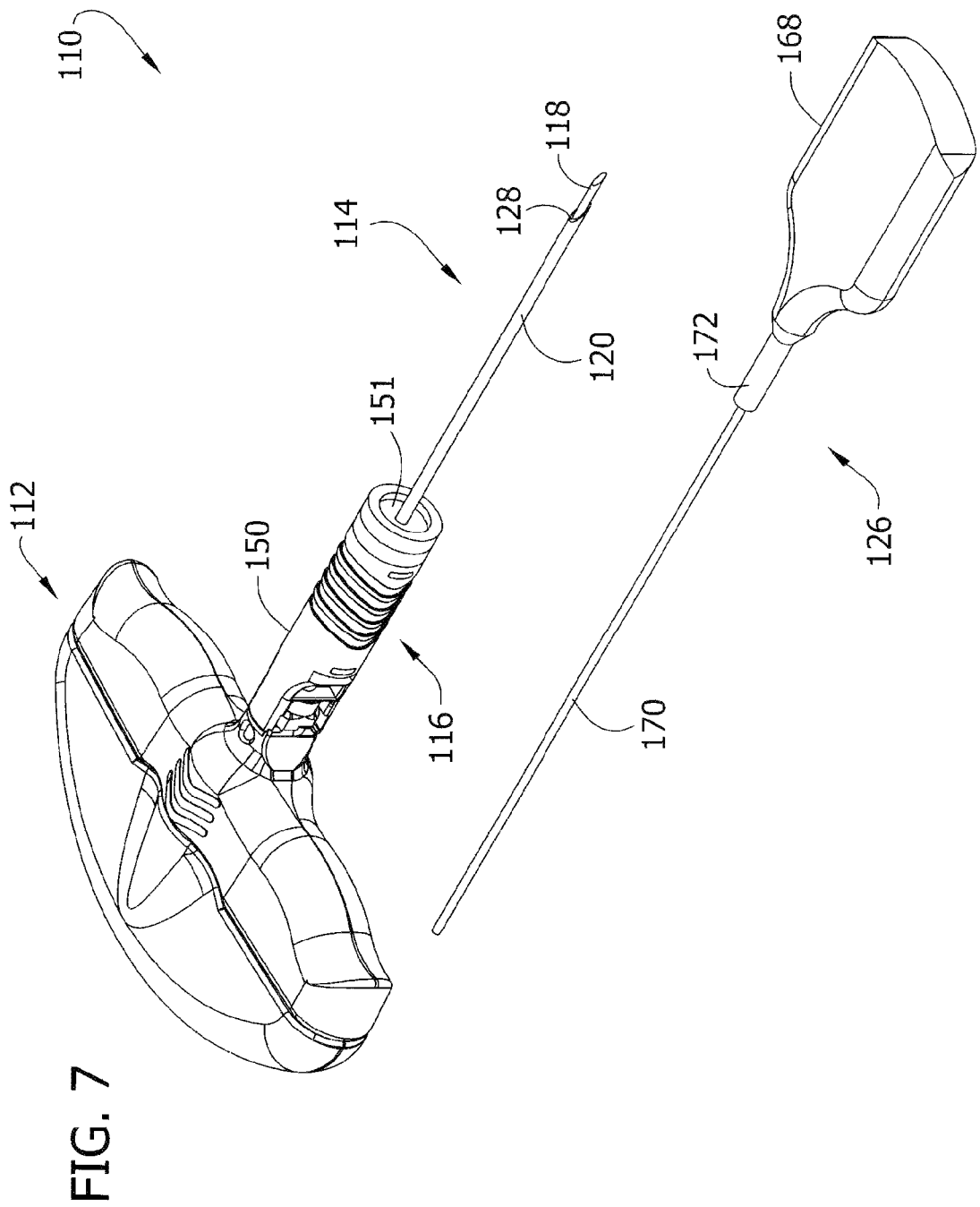
FIG. 7 is a perspective of a needle assembly of a second embodiment including an obturator.

The obturator 26 of the present invention is particularly adapted to permit the tubular housing 50 to be released and moved back from the sharp tip 28 of the cannula 20. From the position shown in FIG. 3, the grip 68 can be advanced toward the tubular housing 50 against the bias of the spring 74 so that the reset member 72 is received into the tubular housing and engages the locking mechanism 52. More particularly, the tabs 64 of the canting member engage a leading free edge portion 80 of the reset member 72 so that the reset member wedges the canting member up to a position in which the base is again substantially orthogonal to the axis of the cannula 20, as shown in phantom in FIG. 4. The open end 73 can receive a portion of the cannula 20 to allow the reset member 72 to be advanced far enough to reset the locking mechanism 52. Movement of the canting member in this manner positions the hole in the base 56 so that the cannula 20 can slide easily through the canting member. Thus as shown in FIG. 5, the tubular housing 50 can be grasped to pull back the safety shield 16 toward the distal housing member 24 so that the sharp tip 28 of the cannula 20 is once again exposed. The obturator shaft 70 can be removed and the stylet 18 can be reinserted into the cannula 20 for a second collection of a sample. It will be appreciated that the spring 74 inhibits the accidental release of the locking mechanism 52. The technician must intentionally overcome the resisting bias of the spring to de-activate the locking mechanism 52.

Referring now to FIGS. 7-11, a needle assembly 110 of a second embodiment is shown to comprise a handle 112 and a needle 114 extending from the handle. A cannula safety shield 116 received on the cannula 120 can be slid down to cover the sharp tip 128 of the cannula. The construction and operation of the handle 112 and needle 114 are substantially the same as for the handle 112 and needle 114 of the needle assembly 110 of the first embodiment. The same reference characters will be used to indicate corresponding parts of the needle assembly 110 of the second embodiment, plus "100". Moreover, the handle 112 and needle 114 will not be further described in view of their similarity to the first embodiment. The safety shield 116 includes a tubular housing 150 and a locking mechanism 152. The locking mechanism 152 may be substantially the same as the locking mechanism 152 of the first embodiment. The tubular housing 150 is similar to the tubular housing 150 of the first embodiment. However, a proximal end of the tubular housing 150 would be open except for an annular, flexible membrane 151 (broadly, "an aligning device") that covers the open end. The membrane 151 has a central aperture 153 that is aligned with the proximal opening of the central axial passageway in the cannula 120. The membrane 151 is used to guide an obturator 126 into the central axial passageway, as will be described.

The obturator 126 comprises a grip 168 and a long, thin shaft 170 extending from the grip and sized for being received in the central axial passageway of the cannula 120. The obturator 126 further includes a tubular reset member 172 projecting from the grip 168 and surrounding the portion of the shaft 170 adjacent to the grip. The construction of the obturator 126 is similar to the obturator 126 of the first embodiment, except that there is no spring 174 or annular cap 176.

Figure 8:
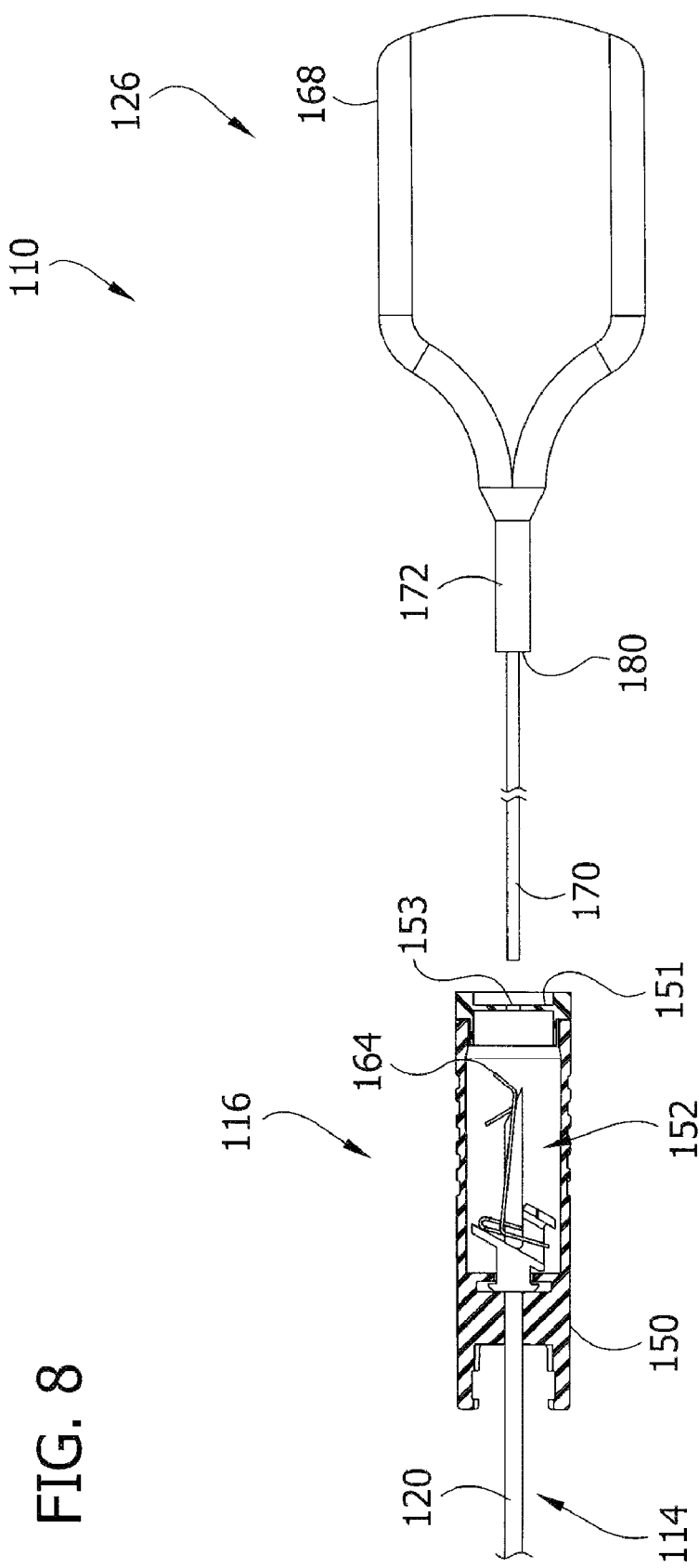
FIG. 8 is a fragmentary partial section of the needle assembly of FIG. 7 illustrating the obturator just prior to insertion into the needle assembly and parts broken away to show internal construction.
Figure 9:
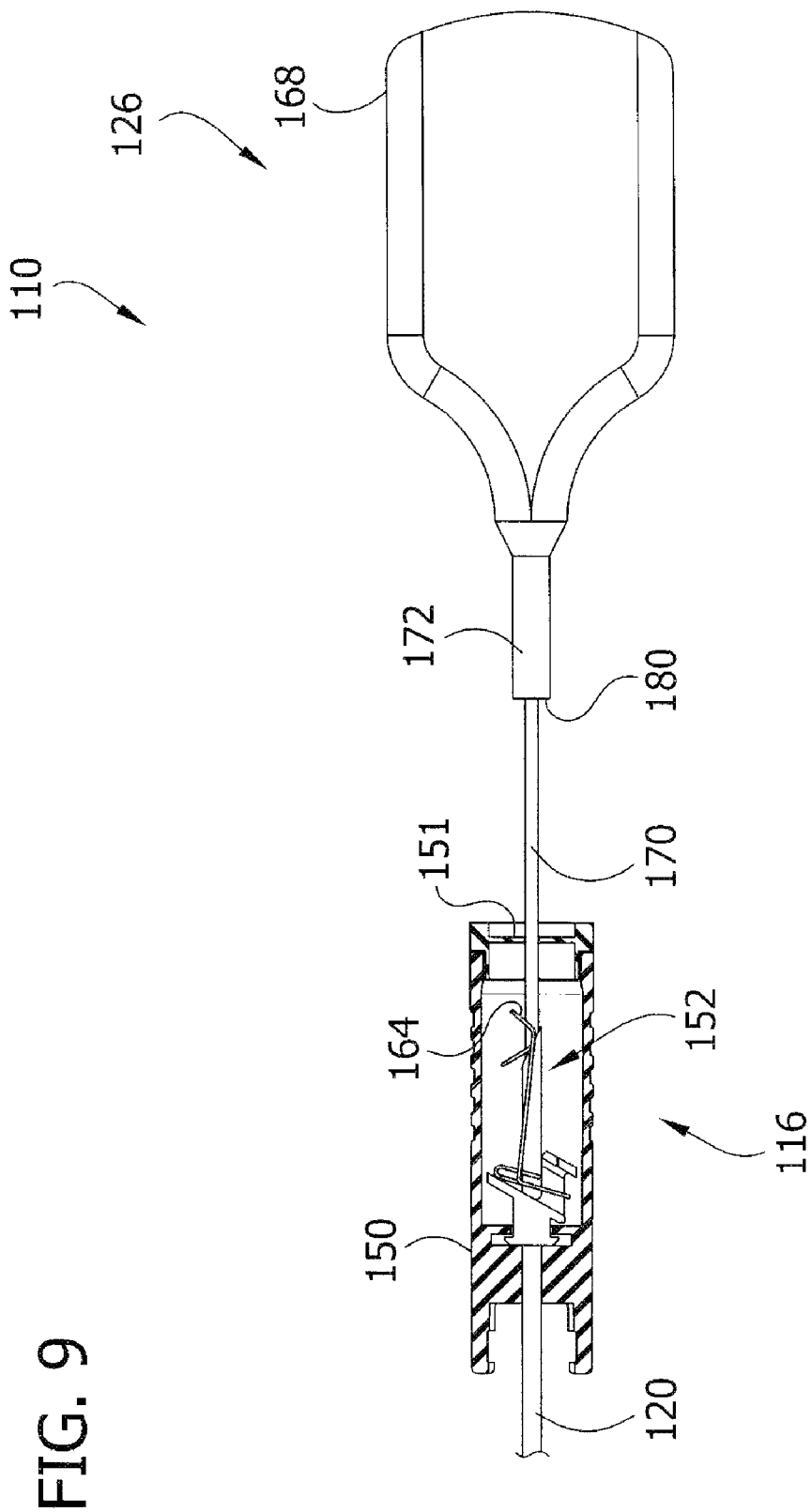
FIG. 9 is the fragmentary partial section of FIG. 8 but showing the obturator inserted into the needle assembly a distance sufficient to remove a sample from the obturator.

FIGS. 8-11 illustrate the operation of the obturator 126 of the second embodiment to remove a bone marrow sample (not shown) from the central axial passageway of the cannula 120 and, if desired, to de-activate the locking mechanism 152 of the safety shield 116 to permit the shield to be withdrawn from the sharp tip 128 of the cannula to reset the needle assembly 110 for a second use. As shown in FIG. 8, the medical technician aligns the shaft 170 with the aperture 153 in the membrane 151 of the safety shield 116, which results in the shaft also being aligned with the central axial passageway of the cannula 120. The shaft 170 is then inserted through the aperture 153 and into the central axial passageway, as shown in FIG. 9. It will be appreciated that the membrane 151 engages the shaft 170 when the shaft is inserted into the aperture 153 and thereby operates to guide the shaft into the central axial passageway. However, other structure for guiding the obturator shaft 170 may be provided, or guiding structure may be entirely omitted without departing from the scope of the present invention. The shaft 170 is sized in length so that at about the same time as a leading edge portion 180 of the reset member 172 engages the membrane 151, or slightly before, the shaft will have passed completely through the cannula 120 and project out the proximal end thereof. The sample (not shown) will have been ejected from the cannula 120 at this point. The reset member 172 may engage the membrane 151, which provides a slight resistance to further advancement of the shaft 170 into the safety shield 116 and central axial passageway of the cannula 120. This signals to the operator that the obturator 126 has been pushed far enough into the cannula 120.

Figure 10:
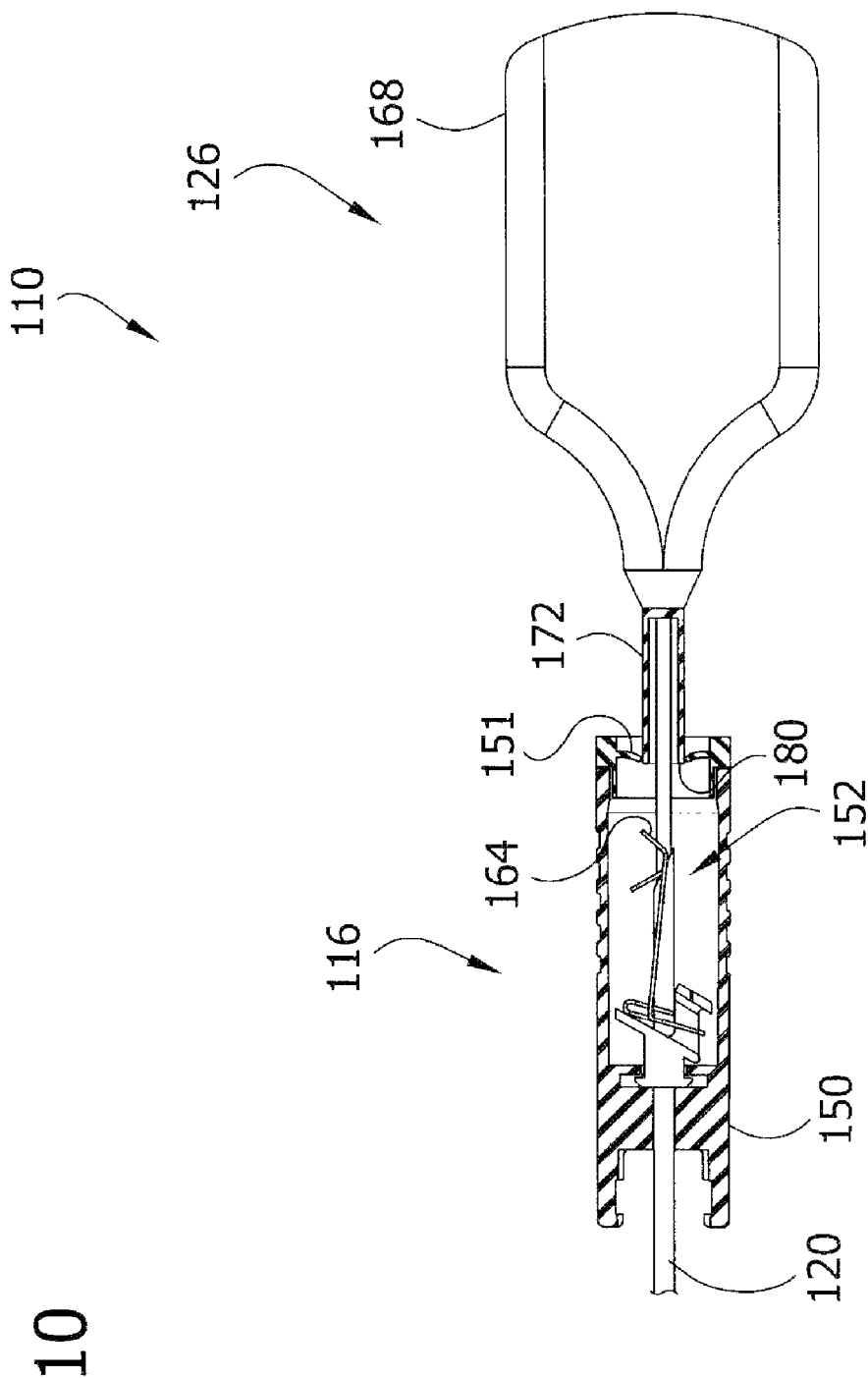
FIG. 10 is the fragmentary partial section of FIG. 8 but showing a reset feature of the obturator entering a safety shield of the needle assembly.
Figure 11:
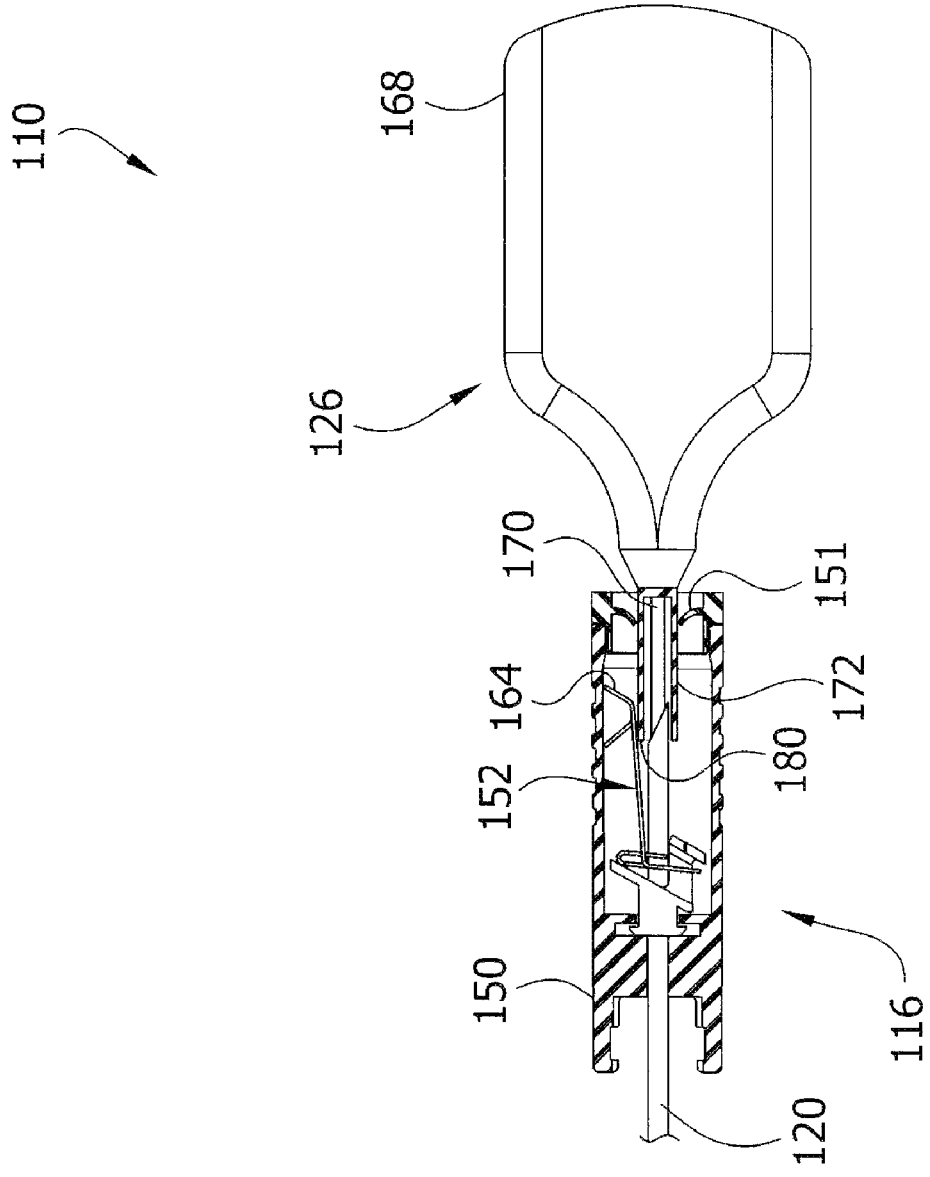
FIG. 11 is the fragmentary partial section of FIG. 8 but showing the obturator resetting a locking mechanism of the safety shield to permit the safety shield to be withdrawn from a sharp end of the needle assembly.

If the sample is satisfactory, the obturator 126 can be withdrawn from the cannula 120 and tubular housing 150, and the needle assembly 110 discarded. However, if a second bone marrow sample needs to be taken, the obturator 126 can be advanced from the position shown in FIG. 9 further into the safety shield 116. As shown in FIG. 10, the reset member 172 deflects and stretches the membrane 151, causing the aperture 153 to enlarge to the extent that the reset member 172 is admitted into the tubular housing 150 through the aperture. The reset member 172 is the only part of the obturator shown in section in FIG. 10. The reset member 172 continues to advance to the position in FIG. 11. As the reset member 172 advances, the leading edge portion 180 engages the tabs 164 of the locking mechanism 152 pushing the locking mechanism back to its position where the safety shield 116 is free to slide along the cannula 120. Thus in substantially the same was as shown in FIG. 5, the tubular housing 150 can be grasped and moved proximally away from the sharp tip 128 of the cannula 120 to ready the needle assembly 110 for a second use.

Figure 12:
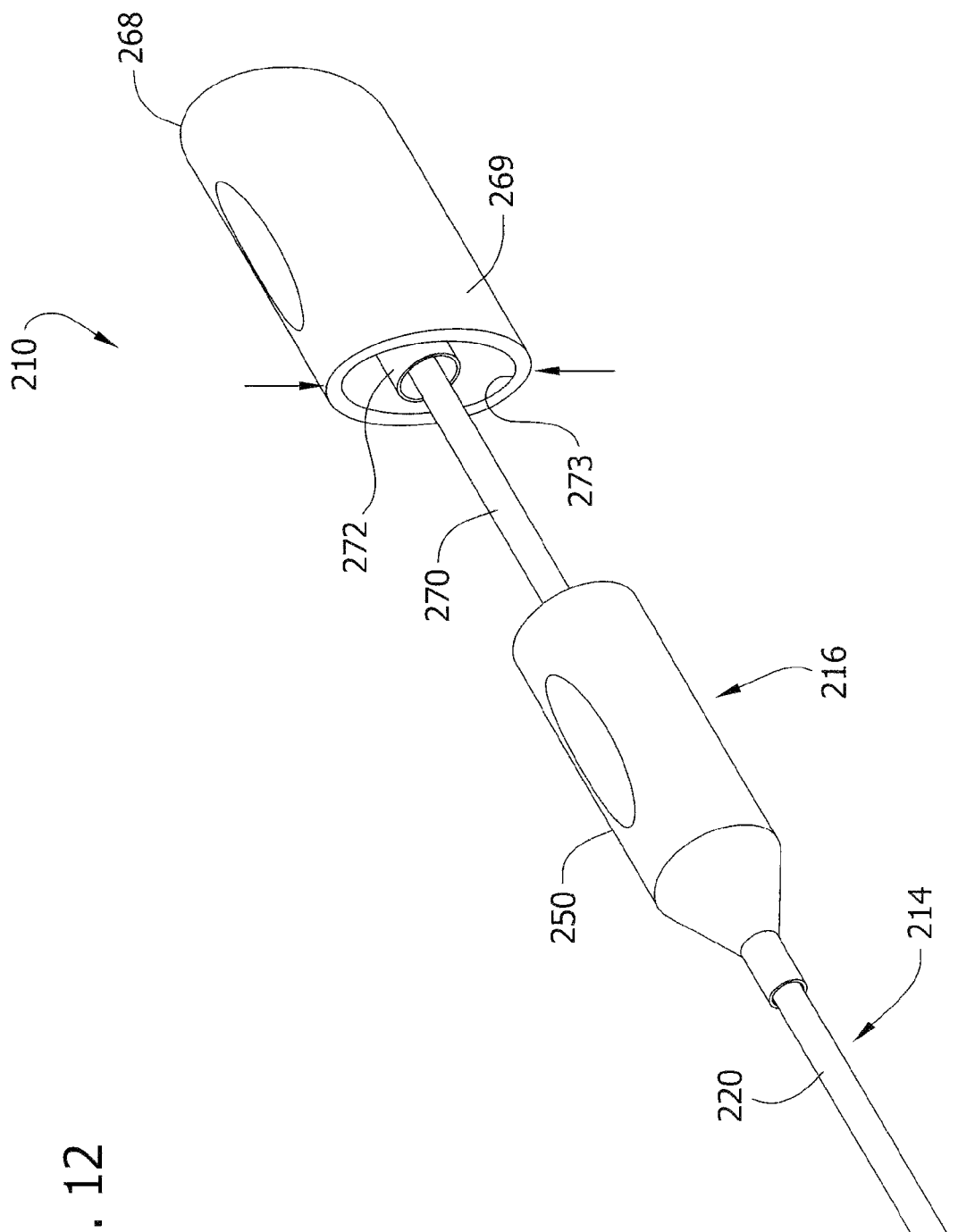
FIG. 12 is a perspective of a needle assembly of a third embodiment including an obturator.

A needle assembly 210 of a third embodiment is shown in FIG. 12. Parts of the needle assembly 210 of the third embodiment are indicated by the same reference numerals as for the needle assembly 210 of the first embodiment, plus "200". The obturator 226 includes a grip 268 having a generally tubular portion 269 that extends along the shaft 270 to a distance which fully surrounds the reset member 272. The cross section of an opening 273 defined by the tubular portion 269 of the grip 268 is elliptical (or otherwise not the same shape as the cross section of the tubular housing 250). The shaft 270 may be inserted into the tubular housing 250 and central axial passageway of the cannula 220 as before. However when the grip 268 reaches the tubular housing 250, it engages the tubular housing because the elliptical cross sectional shape of the opening 273 does not match the circular cross sectional shape of the tubular housing. This prevents the reset member 272 from being inadvertently inserted into the tubular housing 250 resulting in an unintended release of the locking mechanism 252 which could cause the contaminated sharp tip 228 of the cannula 220 to be exposed when the obturator 226 is removed from the central axial passageway.

If it is necessary to de-activate the locking mechanism 252 and withdraw the safety shield 216 from the sharp tip (not shown) of the cannula 220, the obturator 226 can be reconfigured so that the reset member 272 can move into the tubular housing 250. This can be accomplished by squeezing on opposite sides of the grip 268, such as indicated by the arrows in FIG. 12. For instance, the points at which the grip 268 is engaged for squeezing may be the opposite ends of the major axis of the ellipse. The grip 268 is formed of an elastic and resilient material that allows the elliptical shape of the opening 273 to become more nearly circular to match the shape of the tubular housing 250. Once the shapes are matched, the grip 268 and reset member 272 can be advanced, with the grip receiving the tubular housing 250 therein and the tubular housing receiving the reset member 272. The reset member operates to de-activate the locking mechanism 252 in the same way as described previously herein.

Figure 13:
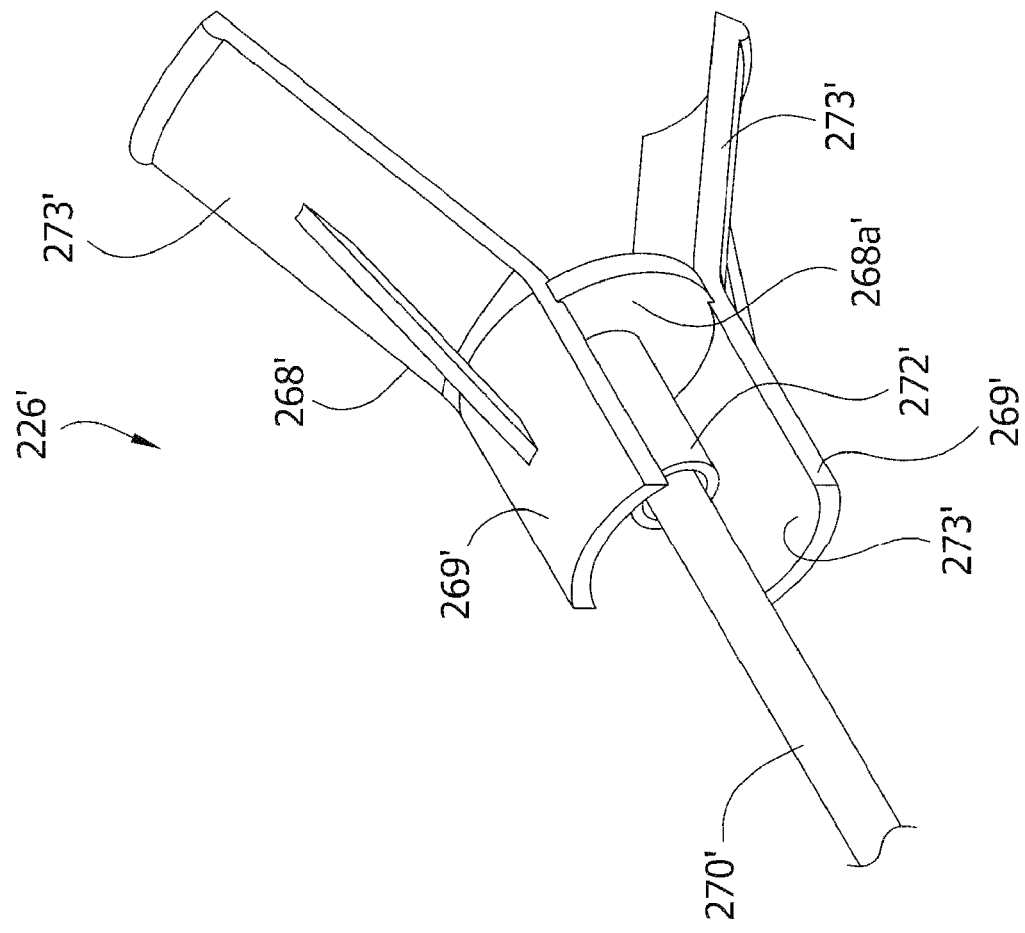
FIG. 13 is a perspective of a modified obturator similar to that of FIG. 12.
Figure 14:
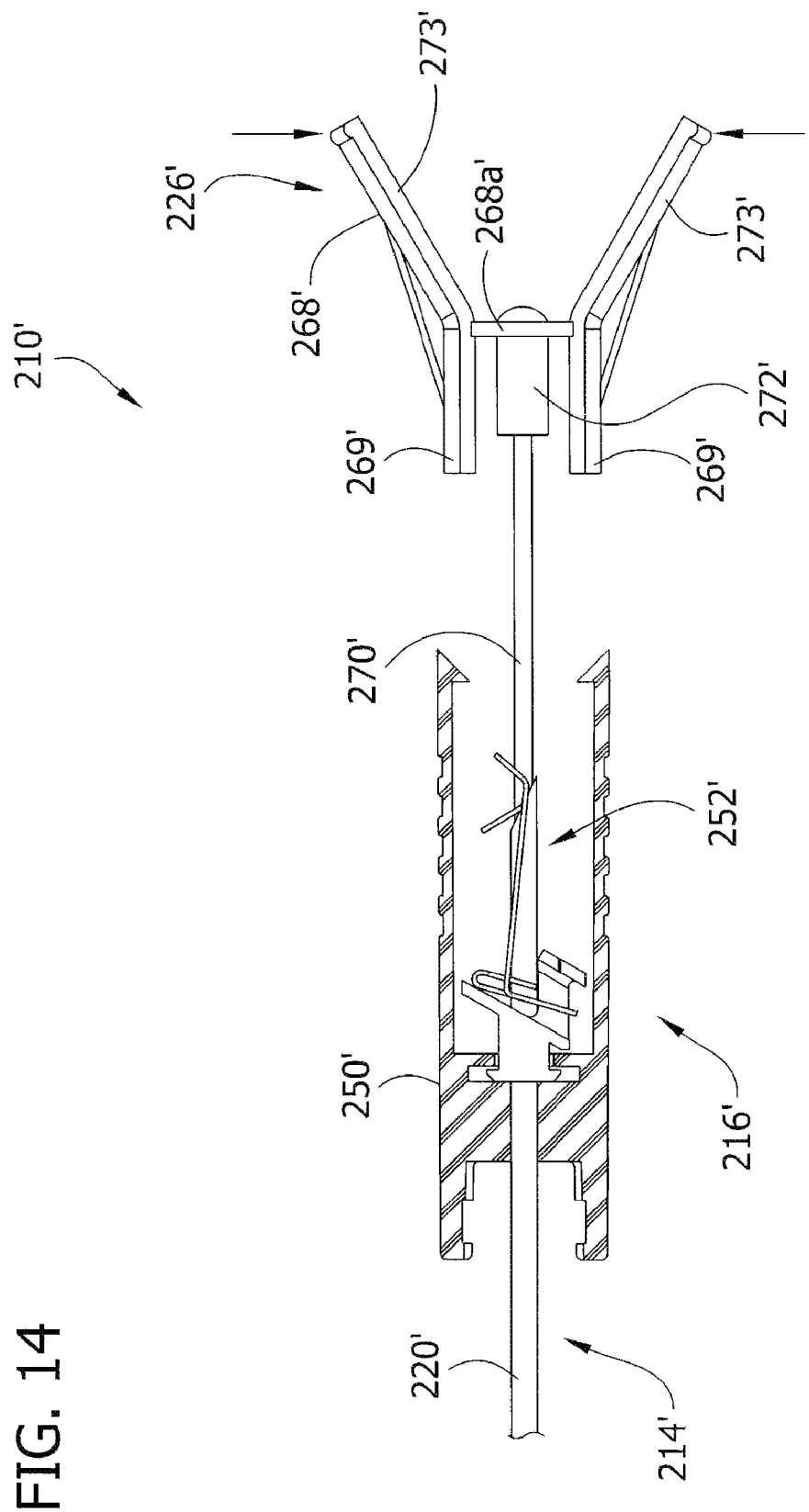
FIG. 14 is a fragmentary partial section showing the obturator of FIG. 13 inserted into the needle assembly but prior to resetting a locking mechanism thereof with parts broken away to show internal construction.

Referring now to FIGS. 13 and 14, a modified obturator 226' of the second embodiment is shown. The same reference numerals as used for the needle assembly 210 of the third embodiment will be used to indicate corresponding parts in the modified version, with the addition of a trailing prime. It is noted that the tubular housing 250' of the safety shield 216' does not include the membrane 151 of the second embodiment, but otherwise may be of the same construction. However, a membrane (not shown) could be employed in this modified version. The principle of operation is similar to the third embodiment. More specifically the grip 268' includes a circular base 268a' from which two projecting members 269' extend a distance greater than the axial extent of the reset member 272'. The projecting members 269' at their free ends are spaced apart across an opening 273' a distance less than the diameter of the tubular housing 250', but are not sized to fit inside the tubular housing. Accordingly when the obturator shaft 270' is inserted into the central axial passageway of the cannula 220' a distance which brings the grip 268' into engagement with the tubular housing 250', the free ends of the projecting members 269' engage the tubular housing and prevent further advancement. Thus, the reset member 272' remains outside the tubular housing 250' and the locking mechanism 252' is not inadvertently de-activated.

To allow the locking mechanism 252' to be de-activated and the safety shield 216' withdrawn from the sharp tip of the cannula 220, the grip 268' is provided with wings 273', each projecting outward from the base 268a' adjacent to a respective one of the projecting members 269'. The wings extend generally in the opposite direction from the base 268a' as the projecting members 269', but also extend radially outward so that the wings 273' diverge from each other. The wings 273' can be gripped and squeezed as indicated in FIG. 14 so that the free ends of the projecting members 269' move apart from each other. The base 268a' acts as the fulcrum about which the projecting members 269' pivot. This movement allows the projecting members 269' to receive the tubular housing 250' between them. The reset member 272' can be advanced into the tubular housing 250' to de-activate the locking mechanism 252' as described previously herein.

Figure 15:
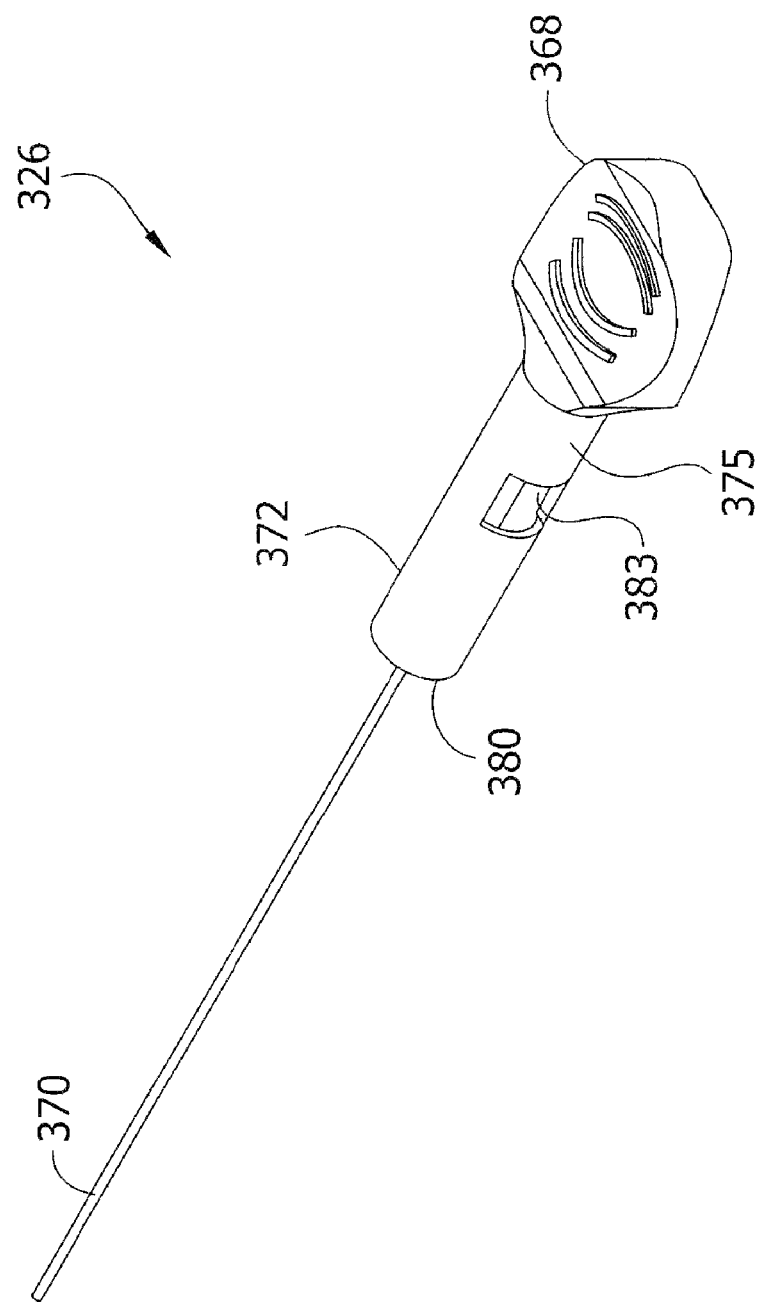
FIG. 15 is a perspective of an obturator of a needle assembly of a fourth embodiment.
Figure 16:
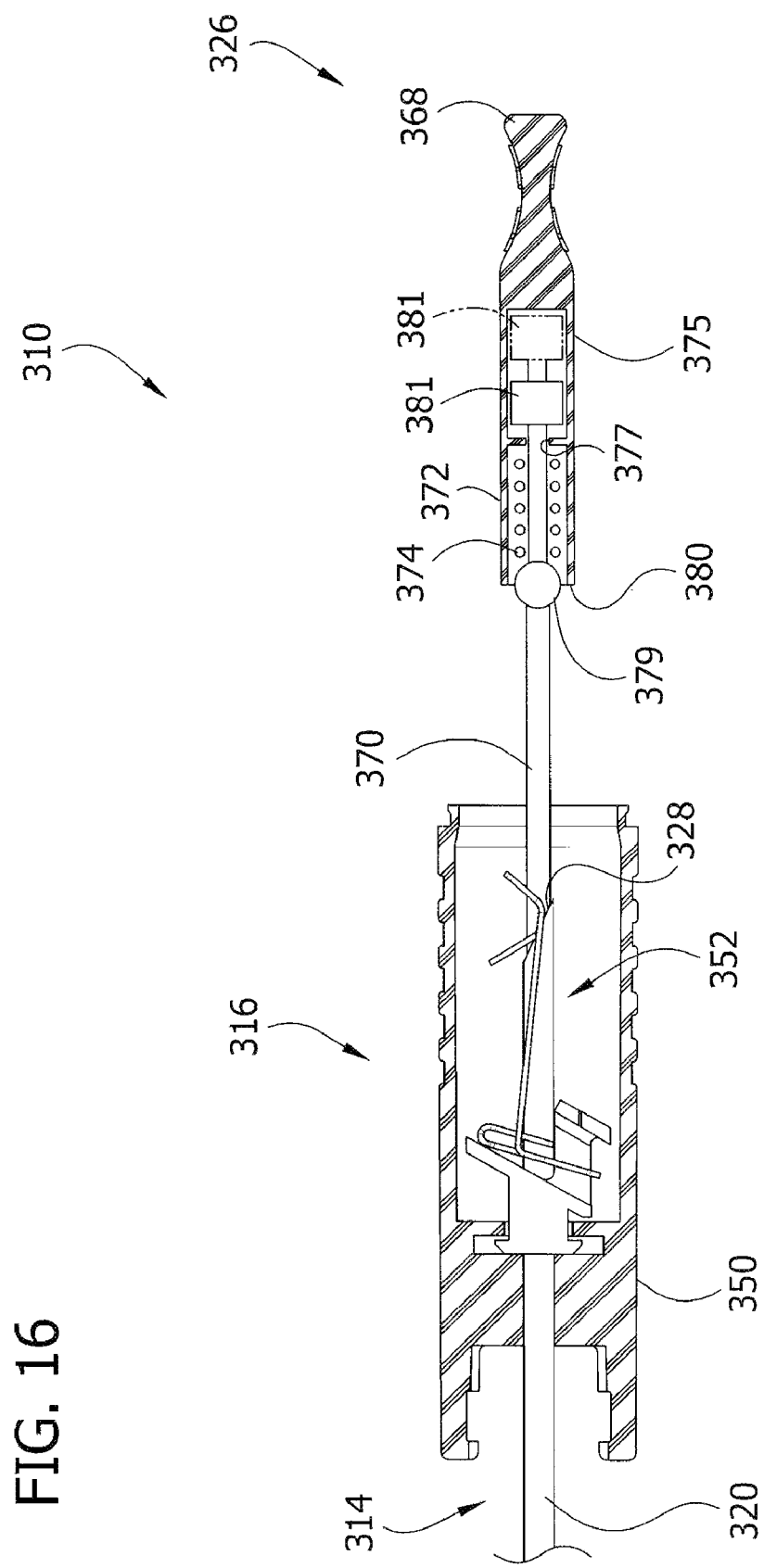
FIG. 16 is a fragmentary partial section of the obturator partially inserted into the needle assembly with parts broken away to show internal construction.

Referring now to FIGS. 15 and 16, a needle assembly 310 of a fourth embodiment includes component parts that are indicated by the same reference numerals as used for the needle assembly 310 of the first embodiment, plus "300". The needle 314 and safety shield 316 shown in FIG. 16 may have the same construction and operation as the corresponding parts in the embodiment shown in FIG. 14. The obturator 326 of the fourth embodiment includes a grip 368 and a hollow cylindrical portion 375 extending axially from the grip. The reset member 372 is located on the axially opposite side of the hollow portion 375 from the grip 368. A hole 377 in the hollow portion 375 allows its interior to communicate with the interior of the tubular reset member 372. The shaft 370 includes an obstruction 379 positioned adjacent the free edge portion 380 of the reset member 372. The shaft 370 extends through the reset member 372 and the hole 377 into the hollow portion 375. The end of the shaft 370 is formed with an indicator plaque 381 that is wider than the hole 377 in the hollow portion 375 so that the shaft 370 may not be withdrawn from the hollow portion. It will be understood that the plaque 381 may have other shapes (e.g., cylindrical with a larger diameter than the hole 377) without departing from the scope of the present invention. The shaft 370 may be moved axially relative to the reset member 372 and hollow portion 375. A coil compression spring 374 is located in the tubular reset member 372. The spring bears against a wall around the hole 377 that separates the interior of the reset member 372 from the interior of the hollow portion 375. The other end of the spring 374 bears against the obstruction 379 on the shaft 370. Thus, the spring 374 biases the shaft 370 axially outwardly from the grip 368, hollow portion 375 and reset member 372.

The hollow portion 375 includes a window 383 defined in the hollow portion 375 that is transparent or translucent. The window could be formed simply by an opening in the hollow portion. The other parts of the hollow portion 375 are opaque. Thus, when the plaque 381 is in the position shown in solid lines in FIG. 16, it cannot be seen through the window 383. However as will be described, the shaft 370 can be moved to bring the plaque 381 into registration with the window 383 so that the plaque is visible through the window. The plaque 381 may be colored to increase its visibility.

In operation to remove a bone marrow sample from the cannula 320, the shaft 370 is aligned with the central axial passage of the cannula and inserted. Although no alignment device is shown, a cap like the cap 376 shown in FIG. 1, a membrane like the membrane 151 shown in FIG. 8, or some other suitable aligning device can be used to assist getting the shaft 370 inside the central axial passageway can be used. The shaft 370 can be easily advanced through the central axial passageway of the cannula 320 until the obstruction 379 engages the distal end of the cannula. The obstruction 379 is too large to fit into the central axial passageway and so resistance to further advancement of the shaft 370 into the cannula 320 is felt by the medical technician. The shaft 370 is sized so that at this point the shaft extends completely through the cannula 320 and the sample (not shown) will have been ejected.

If it is necessary to reset the needle assembly 310 for collecting another bone marrow sample, then the obturator 326 can be advanced against the bias of the spring 374. This allows the reset member 372 to enter the tubular housing 350 of the safety shield 316 for engaging the locking mechanism 352 to de-activate it as described previously. However, the shaft 370 remains stationary relative to the cannula 320 because of the engagement of the obstruction 379 with the cannula. This causes the plaque 381 to move relative to the hollow portion 375 so that it is brought into registration with the window 383 (shown in phantom in FIG. 16). The appearance of the plaque 381 indicates that the reset member 372 has been inserted far enough to de-activate the locking mechanism 352. The technician is given visual confirmation that de-activation has occurred so that he or she knows that the safety shield 316 can be withdrawn (i.e., substantially as shown in FIG. 5). It will be understood that other ways of confirming de-activation of the locking mechanism 352 can be used within the scope of the present invention.

Figure 17:
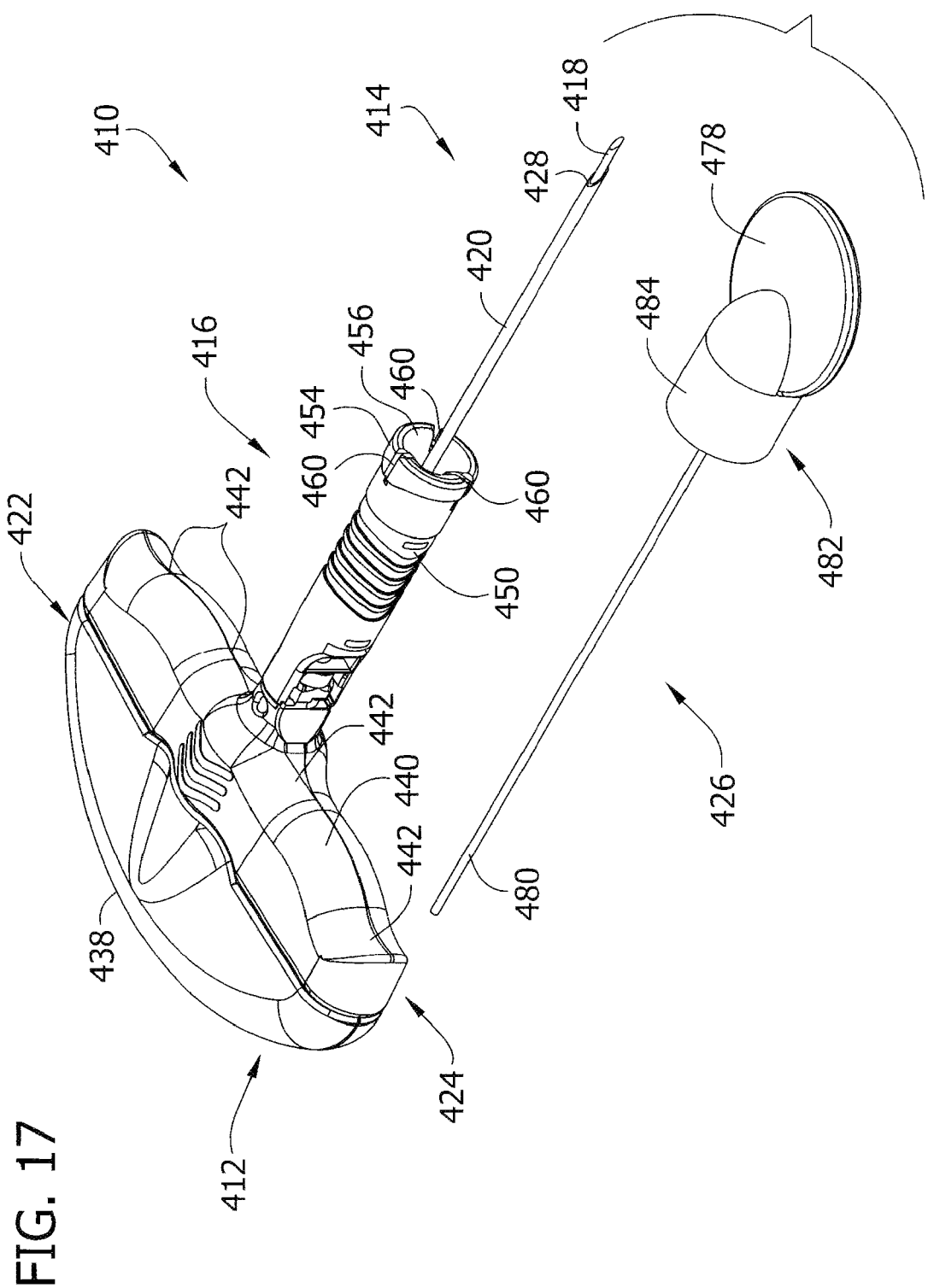
FIG. 17 is a perspective of a bone needle assembly of a fourth embodiment including an obturator.

Referring now to FIGS. 17-24, a medical instrument constructed according to the principles of the present invention is shown in the form of a bone needle assembly, generally indicated at 410 (see, FIG. 17). The bone needle assembly includes a handle 412 (broadly, "mounting structure"), a needle 414 and a cannula safety shield 416, all reference numbers indicating their subjects generally. The needle 414 includes a stylet 418 and a cannula 420 that can receive the stylet. The handle 412 includes a first or proximal handle member (indicated generally at 422) mounting the stylet 418, and a second or distal handle member (indicated generally at 424) mounting the cannula 420. It will be understood that a needle could include only a single component part, or more than two parts within the scope of the present invention. Similarly, a handle could be a single part or more than two parts. The mounting structure for a needle can be other than a handle without departing from the present invention. The needle assembly 410 further includes an obturator 426, which is described more fully below, that may be used to remove a sample captured in the cannula 420.

The cannula 420 has a central axial passage extending the length of the cannula and opening at both ends of the cannula. A distal tip 428 of the cannula 420 is beveled and sharpened, and a proximal end portion of the cannula 420 is received in the distal handle member 424. The stylet 418 is solid and includes a sharp distal tip, and a proximal end portion of the stylet is received in the proximal handle member 422. The stylet 418 can be inserted through the central axial passage opening in the proximal end portion of the cannula 420 and received entirely through the axial passage of the cannula so that its sharp distal tip projects axially outward from the distal tip 428 of the cannula (as shown in FIG. 17). The stylet 418 provides the tool for penetrating the cortical bone, and can be removed from the cannula 420 once the intramedullary canal is accessed by the needle 414.

The handle 412 formed by the proximal and distal handle members 422, 424 has an ergonomic shape that can be comfortably received in a medical technician'ss hand, and allows the technician to easily control the needle assembly 410 as he or she applies the substantial forces needed to penetrate the bone. More specifically, the top or proximal surface 438 of the proximal handle member 422 is rounded in conformance with the shape of the palm of the hand. The bottom or distal surface 440 of the distal handle member 424 is also rounded, but is undulating in shape thereby forming finger wells 442 for receiving the technician'ss fingers. The form of the handle can be other than described herein without departing from the scope of the present invention. Moreover, needle mounting structure can be other than a handle within the scope of the present invention. The proximal and distal handle members 422, 424 can be connected together in a suitable manner when the stylet 18 is received in the cannula 420, so that the handle 412 acts essentially as a single piece when used to drive the needle 414 through a patient'ss skin and into the bone. The proximal and distal handle members 422, 424 can be disconnected and moved apart for removing the stylet 418 from the cannula 420.

The cannula safety shield 416 may be moved to cover the distal tip 428 of the cannula 420 after the needle assembly 410 has been used. The safety shield 416 includes a generally tubular housing 450 and an internal locking mechanism (generally indicated at 452 in FIG. 18) capable of releasably locking the tubular housing in position covering the distal tip 428 of the cannula 420. The tubular housing 450 has a proximal end closer to the handle 412 and a distal end farther away from the handle. A distal end piece of the tubular housing 450 (generally indicated at 454) includes a funnel-shaped distal end surface 456 of the tubular housing 450 and a central aperture 458 generally aligned with the central axial passageway of the cannula 420. Although illustrated as a separately formed part attached to the tubular housing 450, the distal end piece 454 and tubular housing may be formed as a single piece of material. The shape of the distal end surface 456 may be other than described (e.g., lying in a plane perpendicular to the longitudinal axis of the cannula 420) within the scope of the present invention. Three slots 460 located on the periphery of the tubular using distal end piece 454 each extend radially inwardly from the periphery of the end piece at its distal end and also extend axially along the end piece toward the proximal end of the tubular housing 450. The number of slots and their precise configuration may be other than described without departing from the scope of the present invention. The function of the slots 460 will be described hereinafter. The tubular housing 450 and handle 412 may include structure to secure the tubular housing in a retracted position adjacent the handle when not needed. An example of such structure is shown in co-assigned U.S. application Ser. No. 11/146,173, filed Jun 6, 2005, the disclosure of which is incorporated herein by reference.

The locking mechanism 452 inside the safety shield 416 comprises a canting member including a base 462 having a hole and a pair of arms 464 (only one is shown) extending generally axially from the base. The arms 464 are connected together by a U-shaped member 466 at their ends and each has an upwardly (as oriented in the figures) bent tab 468 (only one is shown) projecting axially outward from the end. Before the locking mechanism 452 is activated to lock the tubular housing 450 in position, the ends of the arms 464 ride on the exterior surface of the cannula 420. This holds the canting member so that the base 462 is generally orthogonal so the longitudinal axis of the cannula 420 and the base can move along the cannula (with the safety shield 416), with the cannula sliding substantially unimpeded through the hole in the base. Once the ends of the arms 464 pass the distal tip 428 of the cannula 420, the locking mechanism 452 is constructed so that the ends of the arms move in a generally radial direction toward an opposite side of the longitudinal axis of the cannula 420. This causes the base 462 of the canting member to cant relative to the axis of the cannula 420 so that the hole in the base is no longer orthogonal to the axis of the cannula. As a result, the base 462 at the edge of the hole grippingly engages the cannula 420 to lock the safety shield 416 in place. The locking mechanism 452 further includes angled surfaces 469A, 469B fixed to the tubular housing 450 that can engage the canting member base 462 to keep the canting member in its canted, locking position upon movement of the tubular housing 450 in either direction relative to the cannula 420. It will be understood that a locking mechanism could take on other forms than shown and described without departing from the scope of the present invention.

The safety shield 416 further includes an annular reset plunger 470 located inside the tubular housing 450 near its distal end. The reset plunger 470 is movable axially relative to the housing 450 toward the proximal end and includes a frustoconically shaped front surface 472 that is engageable with the tabs 468 of the locking mechanism to release the locking mechanism, as will be more fully described hereinafter. A spring 474 engages the reset plunger 470 and biases it toward the distal end of the tubular housing 450. Thus, unless the reset plunger 470 is forcibly moved, it normally does not interfere with the operation of the locking mechanism 452.

The needle assembly 410 is driven into the bone by grasping the handle 412 and pushing the stylet 418 through the skin, underlying tissue and cortical bone. Once this penetration has been achieved, the stylet 418 is no longer required. The proximal handle member 422 is disconnected from the distal handle member 424 and moved axially away from the distal handle member so that the stylet 418 slides out of the central axial passageway of the cannula 420 while the cannula remains in the bone. In order to collect a sample of bone marrow, the distal handle member 424 is advanced further into the bone. The sharp tip 428 of the cannula 420 cuts into the bone marrow and a sample is received in the central axial passageway of the cannula. The cannula 420 can then be withdrawn from the patient by pulling on the distal handle member 424. The sample remains lodged in the central axial passageway of the cannula 420 near the sharp tip 428. It will be understood that a needle assembly may be used to collect a sample other than of bone marrow within the scope of the present invention. Moreover, it is not necessary that a cannula be used to collect any sample. For instance, the cannula could also be used to withdraw or infuse fluid.

The obturator 426 is used to remove a lodged sample of bone marrow that has been collected in the central axial passageway of cannula 420. The obturator 426 includes a grip 478 and a long, thin shaft 480 extending from the grip that is sized to be received in the central axial passageway of the cannula 420 in generally close fitting relation therein. The grip 478 is sized and shaped to be grasped by a user (e.g., between the thumb and pointer finger) for manipulating the obturator 426, as will be described. As shown best in FIGS. 22 and 23, a reset key, generally indicated 482, extends from the grip 478 in the same direction as the shaft 480, and as illustrated is formed as one piece of material with the grip. In the illustrated fourth embodiment, the reset key 482 (broadly, "a reset member") comprises a tubular shroud 484 (broadly, "a support") defining a central open space 486 sized and shaped to receive a portion of the tubular housing 450 therein. Although shown as a solid tubular piece of material with an open end, the shroud 484 need not be solid around its circumference within the scope of the present invention. Three elongate ribs 488 formed on an inner wall 490 of the tubular shroud 484 extend generally parallel to the axis of the shroud and are arranged for reception in the slots 60 of the tubular housing 450 as will be described. It will be appreciated that a reset key (not shown) may not be part of an obturator (i.e., the reset key would not include a shaft like shaft 480) without departing from the scope of the present invention.

Figure 18:
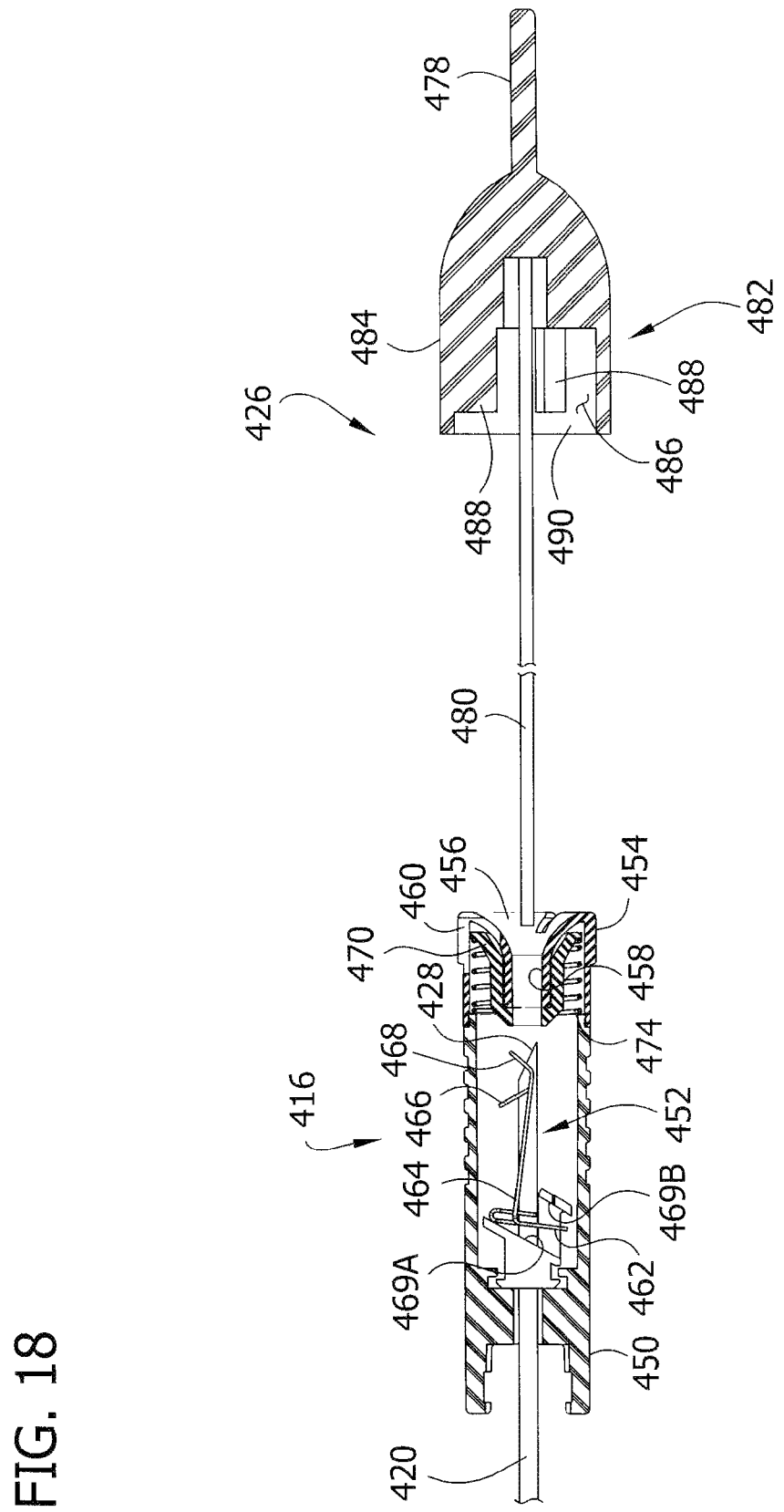
FIG. 18 is a fragmentary partial section of the needle assembly with the obturator entering a safety shield of the needle assembly.
Figure 19:
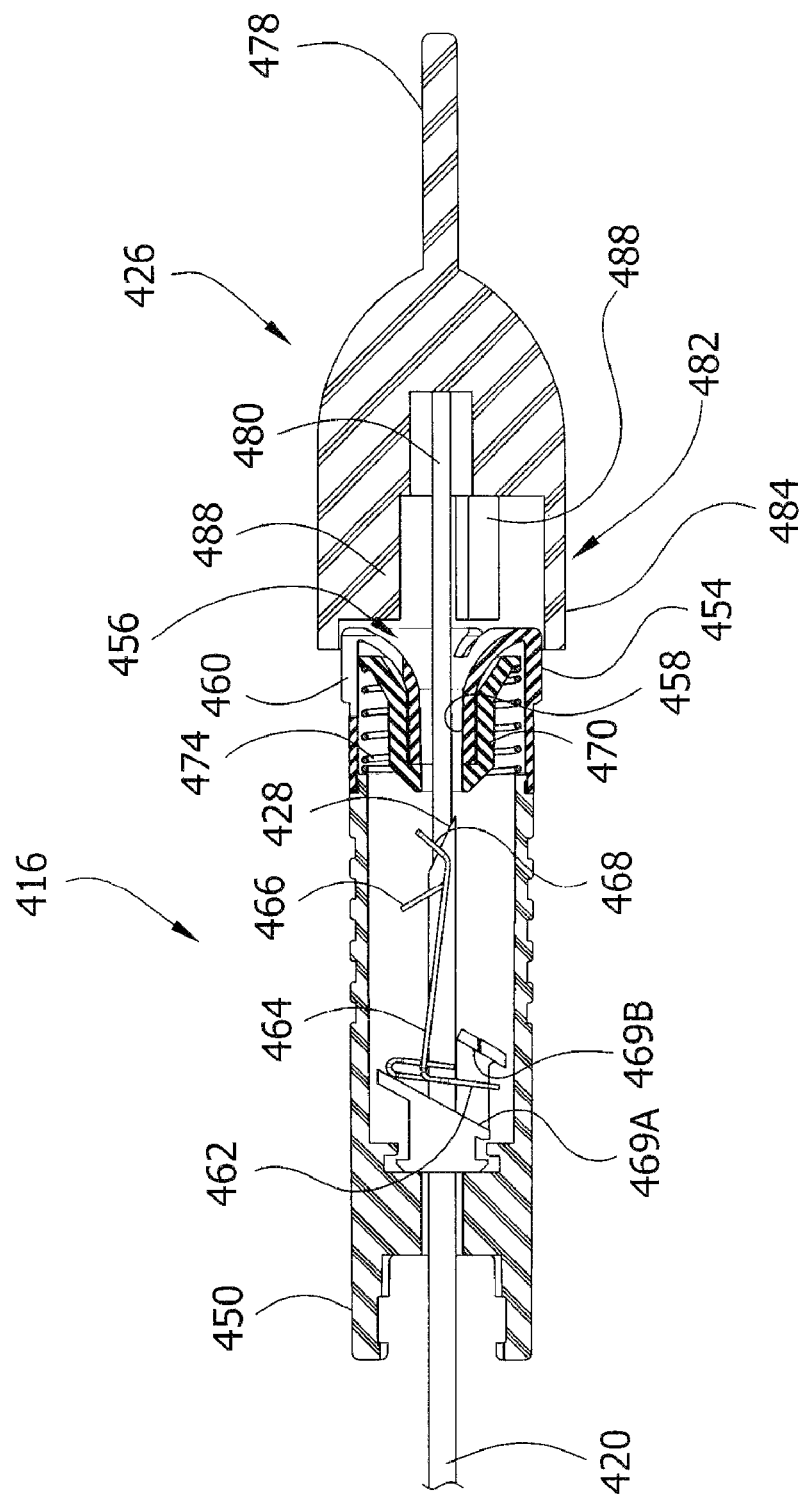
FIG. 19 is the fragmentary elevation of FIG. 18 but showing the obturator inserted to a position in which a sample collected by the needle assembly is pushed out of the needle assembly.

FIG. 18 illustrates the initial position of the obturator 426 with the shaft 480 entering the distal end of the tubular housing 450. The free end of the shaft 480 has not yet entered the central axial passageway of the cannula 420 or the aperture 458 of the distal end piece 454. The funnel-shaped surface 456 of the distal end piece 454 guides the shaft 480 toward the aperture 458 that is aligned with the central axial passageway of the cannula 420, thereby facilitating reception of the shaft in the passageway. The grip 478 is pushed to advance the shaft 480 through the aperture 458 in the funnel-shaped surface 456 and into the central axial passageway, which pushes the sample toward the proximal end of the central axial passageway. The shaft 480 is advanced until it protrudes out of the proximal end of the central axial passageway, thereby pushing the sample (not shown) out of the cannula 420 where it can be collected in a Petri dish or other suitable container. The relative location of the tubular shroud 484 and safety shield 416 are in this position are illustrated in FIG. 19. As the shaft 480 is advanced, it slides through the aperture 458 in the distal end piece 454. The locking mechanism 452 remains engaged so that the safety shield 416 does not move and the sharp tip 428 remains covered.

The technician may observe the sample ejected from the central axial passageway of the cannula 420. If it is determined that the sample is satisfactory, the obturator 426 can be pulled so that the shaft 480 slides back through and out of the cannula 420. The needle assembly 410 can be discarded, or possibly but less likely, cleaned and sterilized for a subsequent use. If the sample is not satisfactory, however, it will be necessary to obtain a second sample from the same patient. This can be done using the same needle assembly 410, but the tubular housing 450 is locked in place by the locking mechanism 452 over the sharp tip 428 of the cannula 420. The tubular housing 450 needs to be moved away from the tip 428 before the needle assembly 410 can be used to obtain a second sample.

The obturator 426 of the present invention is particularly adapted to permit the safety shield 416 to be released and moved back from the sharp tip 428 of the cannula 420. It should be understood, however, that a device other than an obturator 426 incorporating the resetting, or unlocking, features of the obturator described herein, but not functioning as an obturator, is also contemplated as within the scope of the present invention. From the position shown in FIG. 19, the grip 478 can be advanced toward the tubular housing 450 so that the ribs 488 are received into the corresponding peripheral slots 460 in the tubular housing 450. It will be necessary to align the ribs 488 with corresponding ones of the slots 460 before the ribs may enter the slots. The slots 460 and ribs 488 may be shaped and/or arranged to make this easier or harder to accomplish as desired. In the illustrated embodiment, the three slots 460 and three ribs 488 are all the same size and shape and located at 120 degree intervals. This arrangement makes it relatively easy to align the obturator 426 and safety shield 416 so that the ribs 488 will be received in the slots 460. However, as stated previously, other arrangements and configurations are envisioned. For example and without limiting the breadth of the present disclosure, the slots 460 and ribs 488 can be arranged at unequal intervals. Moreover, the slots 460 and ribs 488 may have different sizes so that the ribs will be received in the slots in only one relative orientation of the obturator 426 and the safety shield 416. Those of ordinary skill in the art will appreciate other possible configurations and/or arrangements. The bias of the spring 474 resists further advancement of the ribs 488 and hence of the obturator 426. This provides a tactile signal to the technician that the obturator shaft 480 has been inserted far enough into the central axial passageway of the cannula 420 to remove the sample, and that further insertion will result in release of the locking mechanism 452.

Figure 20:
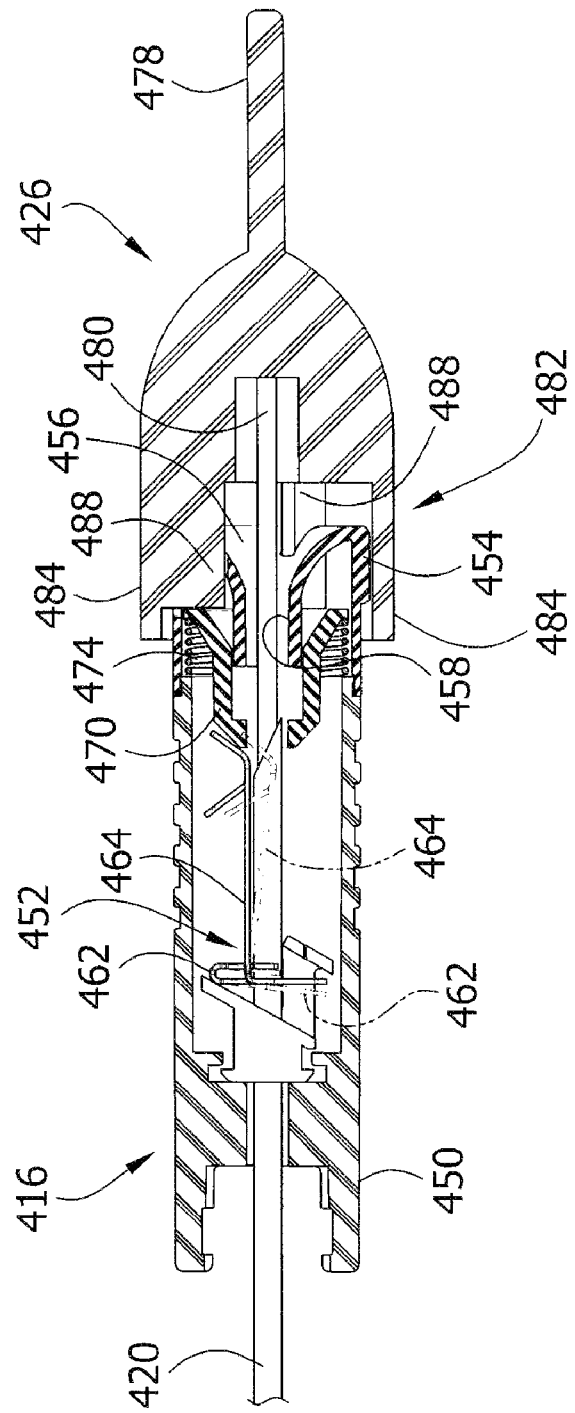
FIG. 20 is the fragmentary elevation of FIG. 18 but showing use of the obturator to reset a locking mechanism of the safety shield.
Figure 21:
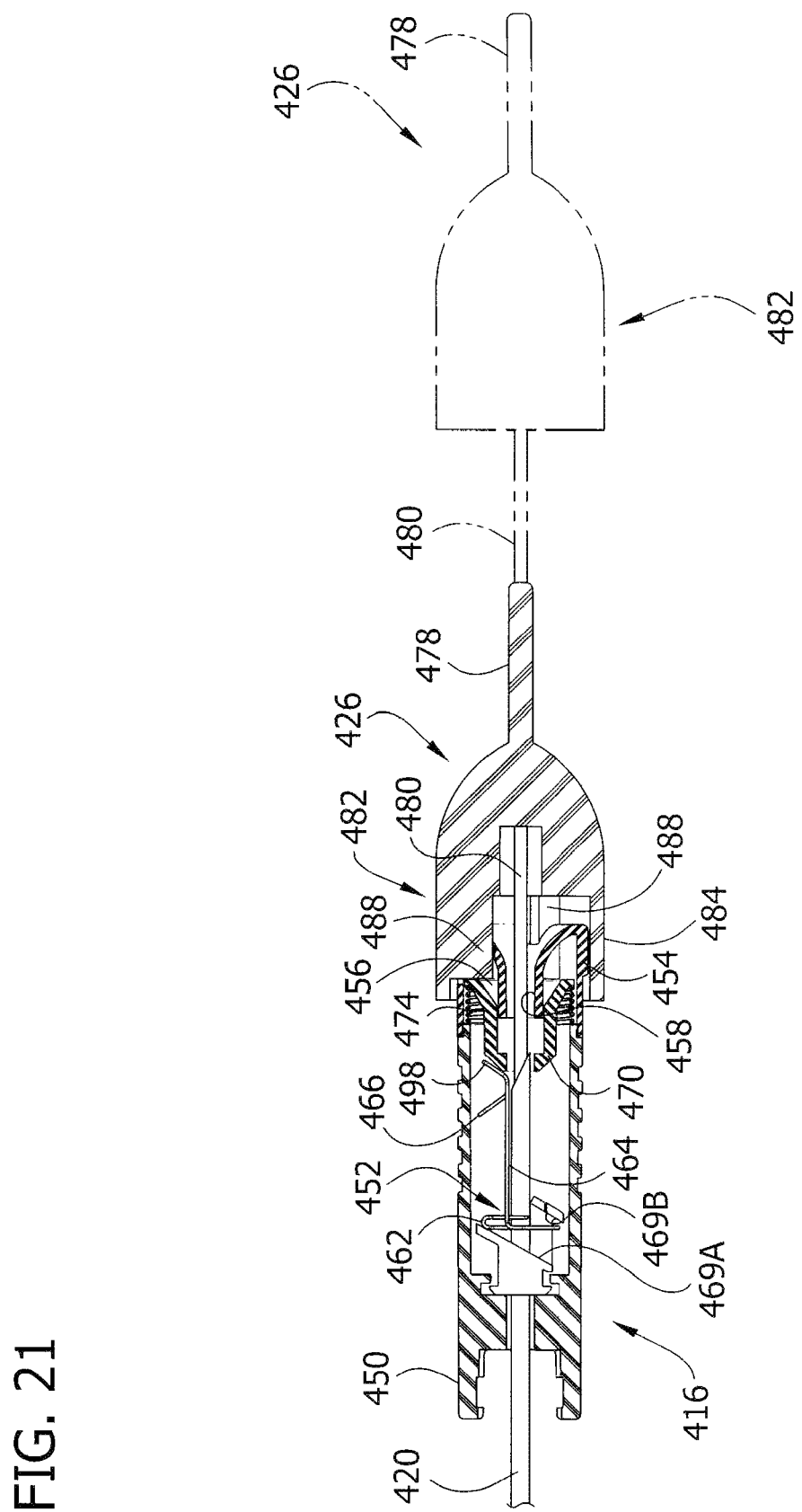
FIG. 21 is the fragmentary elevation of FIG. 18 but showing the safety shield set for withdrawal from a sharp end of the needle assembly after release of the locking mechanism.
Figure 22:
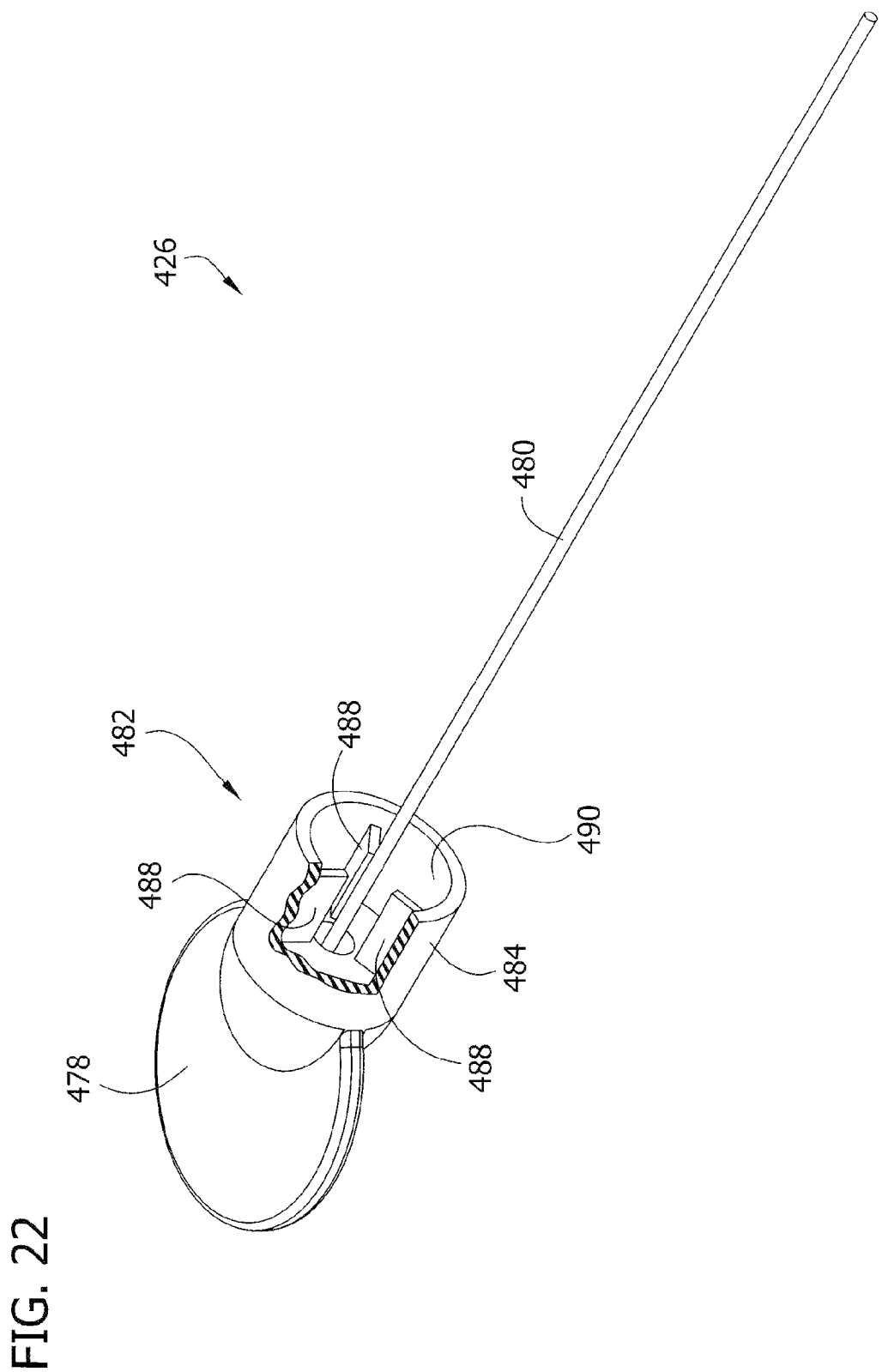
FIG. 22 is a fragmentary perspective of the obturator with parts broken away to show internal construction.
Figure 23:
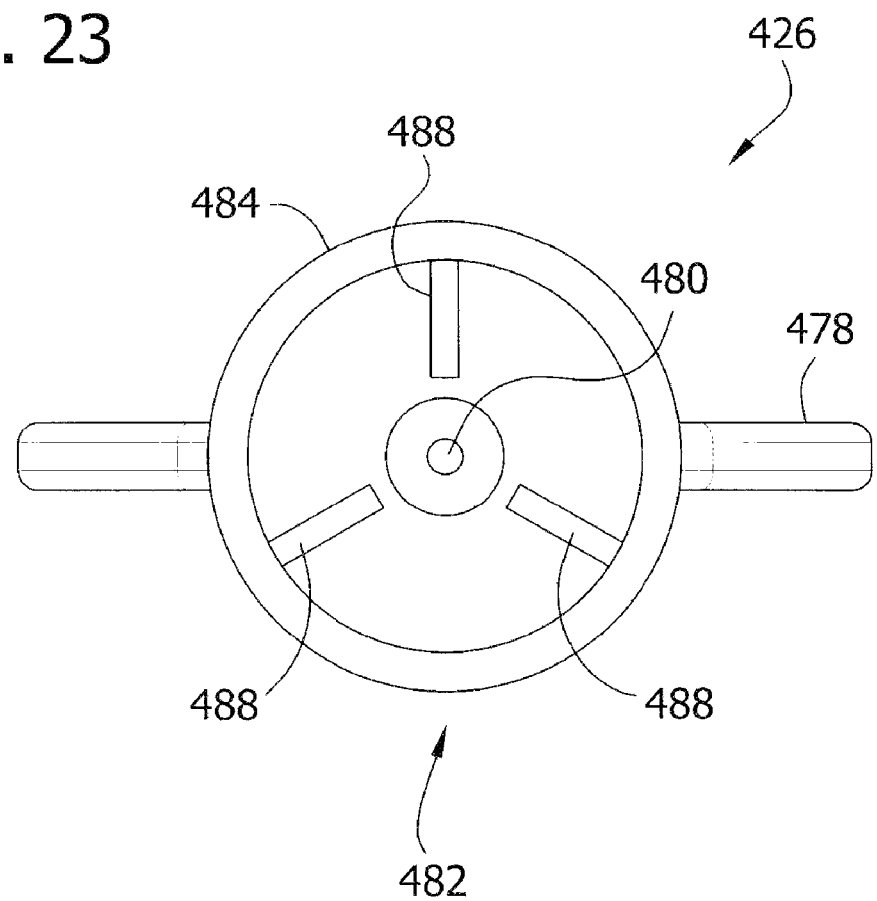
FIG. 23 is an end view of the obturator.
Figure 24:
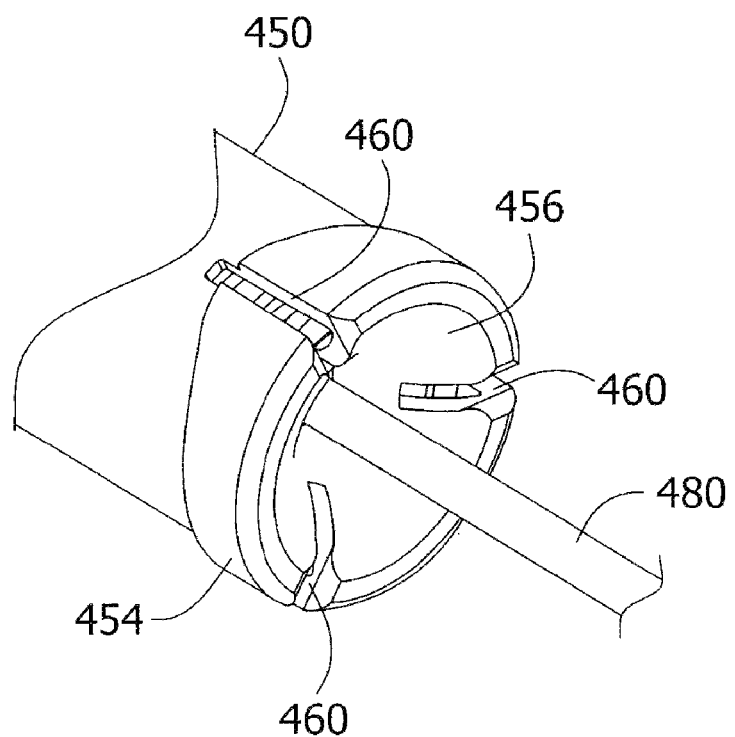
FIG. 24 is a fragmentary perspective of the obturator entering the safety shield.

If the safety shield 416 is to be reset to expose the sharp tip 428 of the cannula 428, the grip 478 can be advanced toward the tubular housing 450 so that the ribs 488 move into the slots 460 and push the reset plunger 470 against the bias of the spring 474 axially toward the proximal end of the tubular housing 450. The front surface 472 of the reset plunger 470 engages the tabs 468 of the canting member moving the arms 464 back to a position more nearly parallel to the longitudinal axis of the cannula 420. This moves the base 462 of the canting member to a position substantially orthogonal to the longitudinal axis of the cannula 420 so that the cannula can once again slide freely through the hole in the base (FIG. 20). The locking mechanism 452 is thereby released. Thus as shown in FIG. 21, the tubular housing 450 can be grasped to pull back the safety shield 416 toward the distal housing member 424 so that the sharp tip 428 of the cannula 420 is once again exposed. The obturator shaft 480 can be removed and the stylet 418 can be reinserted into the cannula 420 for a second collection of a sample. When the ribs 488 move back out of the slots 460, the spring 474 moves the reset plunger 470 back toward the distal end of the tubular housing 450 so that the locking mechanism 452 is again free to operate for locking the safety shield 416 over the sharp tip 428 of the cannula 420.

Figure 25:
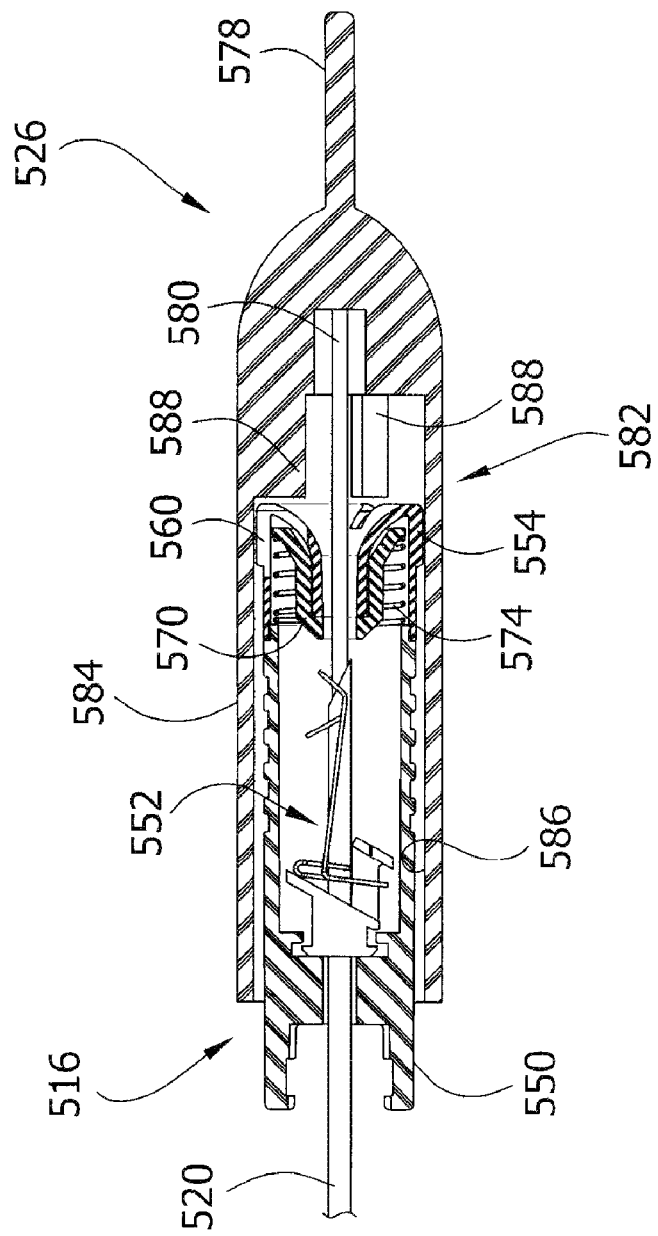
FIG. 25 is a fragmentary partial section of a needle assembly of a fifth embodiment in a configuration similar to FIG. 19.
Figure 26:
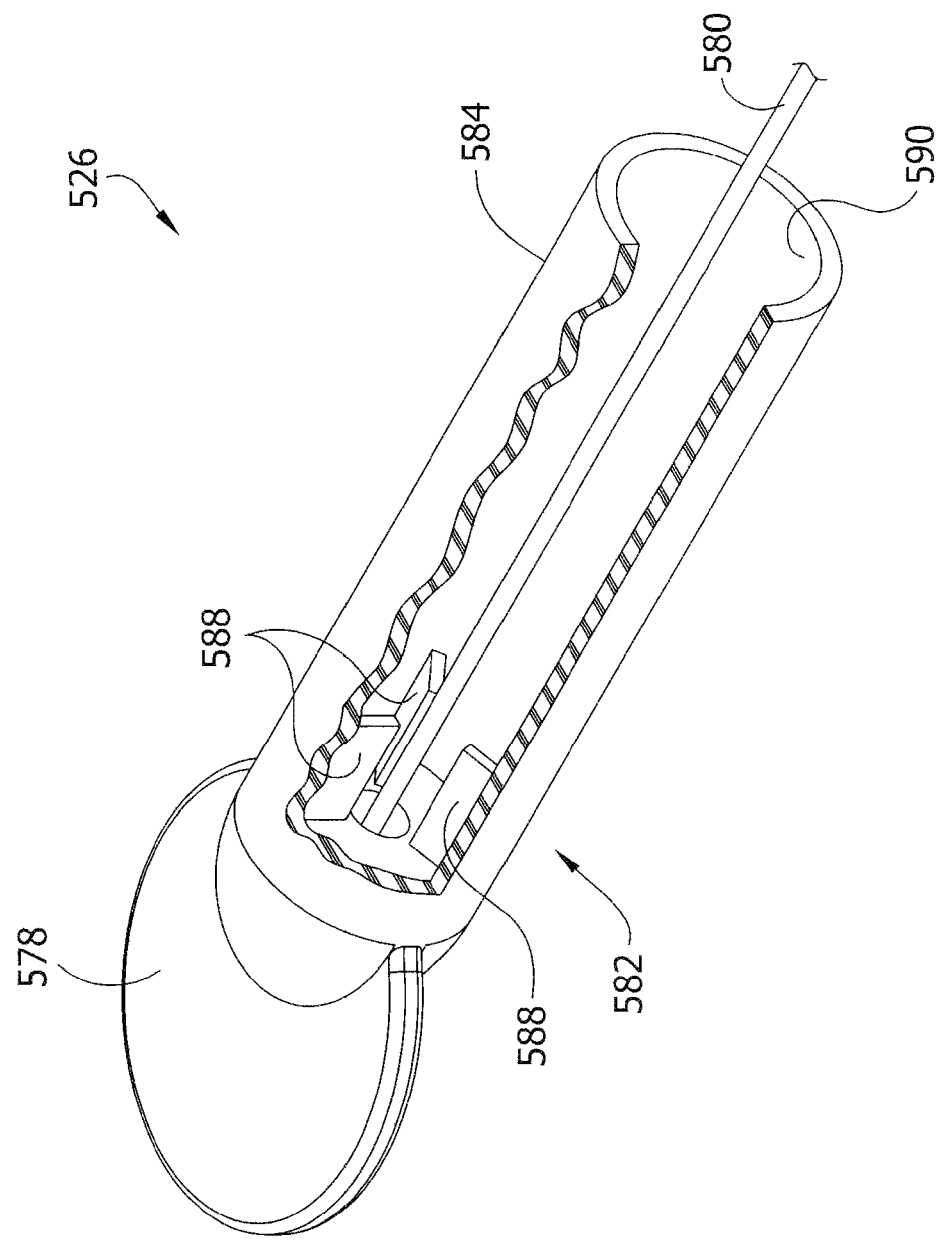
FIG. 26 is a fragmentary perspective of an obturator of the needle assembly of FIG. 25.
Figure 27:
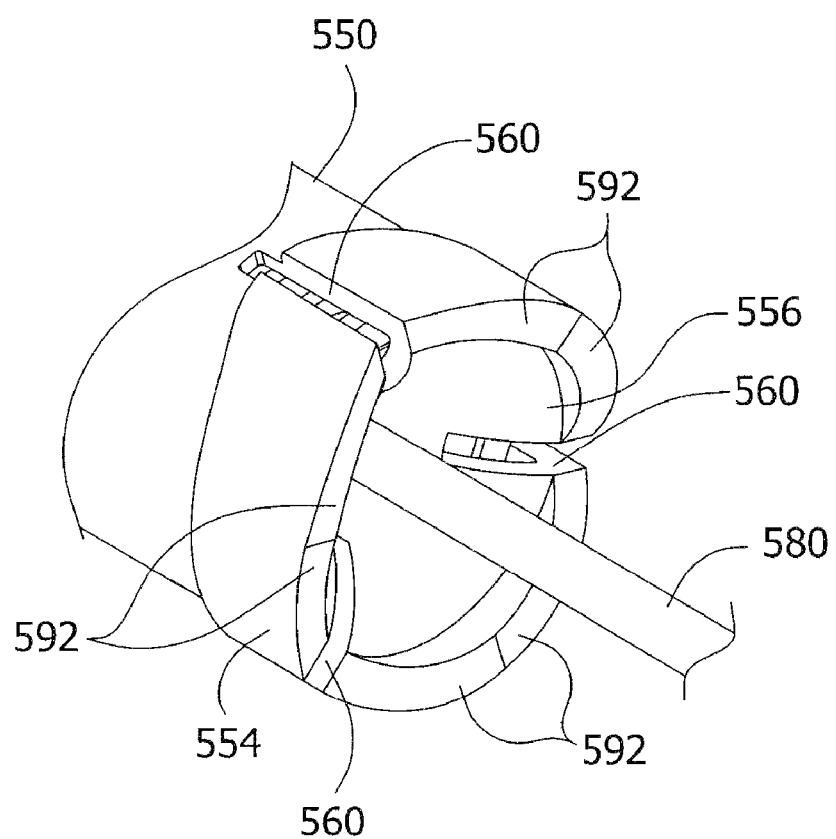
FIG. 27 is a fragmentary perspective of an end of a shield of the needle assembly of FIG. 25.

Referring now to FIGS. 25 and 26, a needle assembly of a fifth embodiment is shown. Parts of the needle assembly of the fifth embodiment are given the same reference numerals as the corresponding parts of the needle assembly of the fourth embodiment, plus "100". A safety shield 516 may have substantially the same construction as the safety shield 516. In particular, the shield 516 includes a tubular housing 550 having peripheral slots 560, as in the fourth embodiment. An obturator 526 and reset key 582 also have similar constructions (e.g., including ribs 588) as in the fourth embodiment. However, a tubular shroud 584 of the fifth embodiment has a length which is sufficiently great so that a central open space 586 of the shroud can receive substantially the entire tubular housing 550. Preferably at least a majority of the tubular housing 550 is received in the open space 586 of the shroud 584. The operation of ribs 588 associated with the tubular shroud 584 to release a locking mechanism 552 may be as described for the fourth embodiment. However by receiving tubular housing 550 in the central open space 586 of the shroud 584, the tubular housing is shielded from being inadvertently grasped as the obturator is pulled away from the safety shield so that the safety shield 516 is not unintentionally pulled off of the cannula 520, or otherwise prematurely removed from the needle. As best seen in FIG. 27, the peripheral edge of a distal end piece 554 of the tubular housing 550 is shaped to include edge segments 592 arranged at converging angles to funnel the ribs 588 into the slots 560 when the ribs engage the distal end piece. Because the ribs 588 are located deep inside the tubular shroud 584 at the bottom of the open space 586, alignment of the ribs with the slots 560 could be difficult. However, the shaped peripheral edge segments 592 engage the ribs 588 and urge the rotation of the obturator 526 to properly orient the reset key 582 so that the ribs move into the slots 560.

Figure 28:
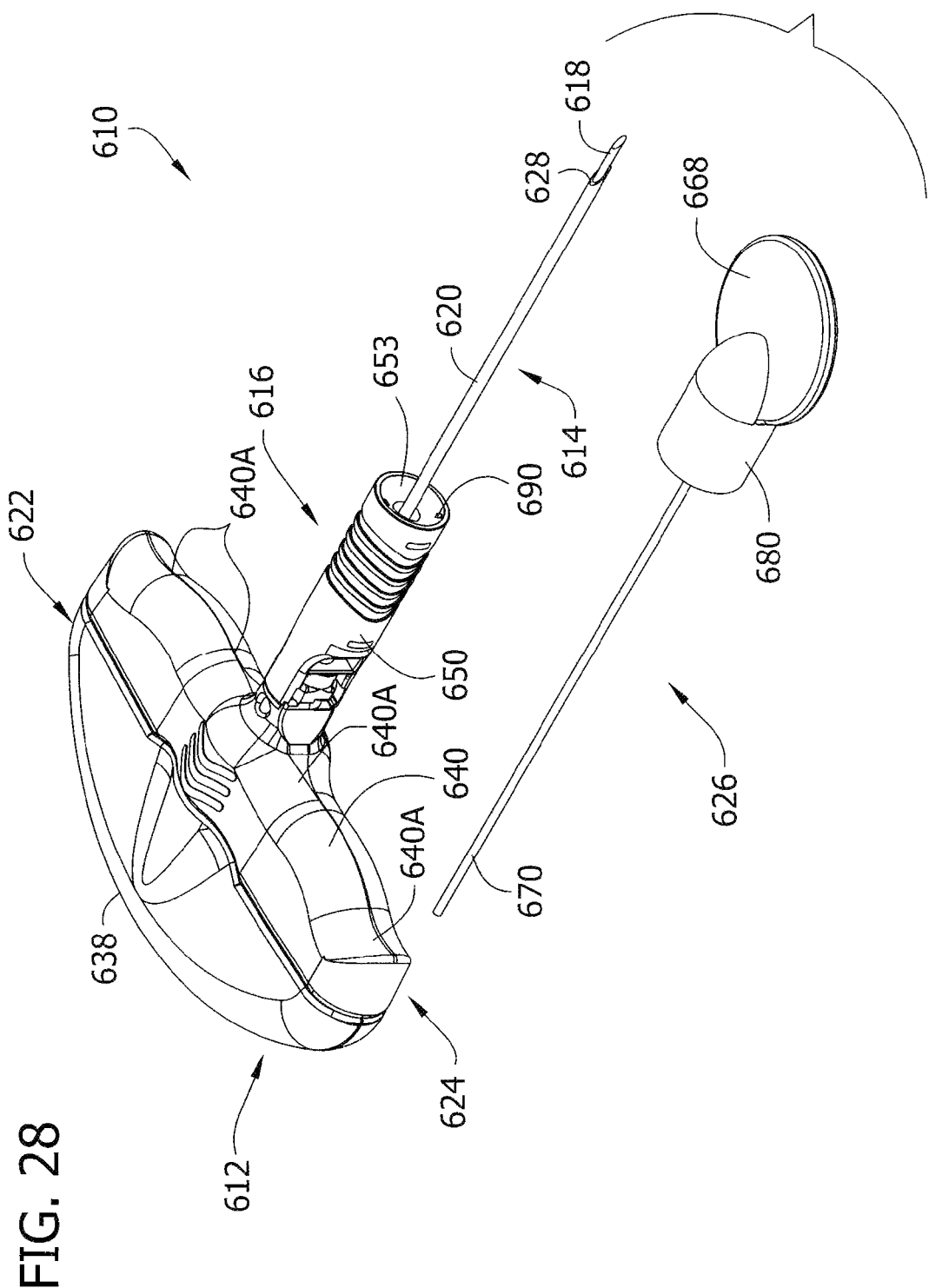
FIG. 28 is a perspective of a bone needle assembly of a sixth embodiment including an obturator.
Figure 29:
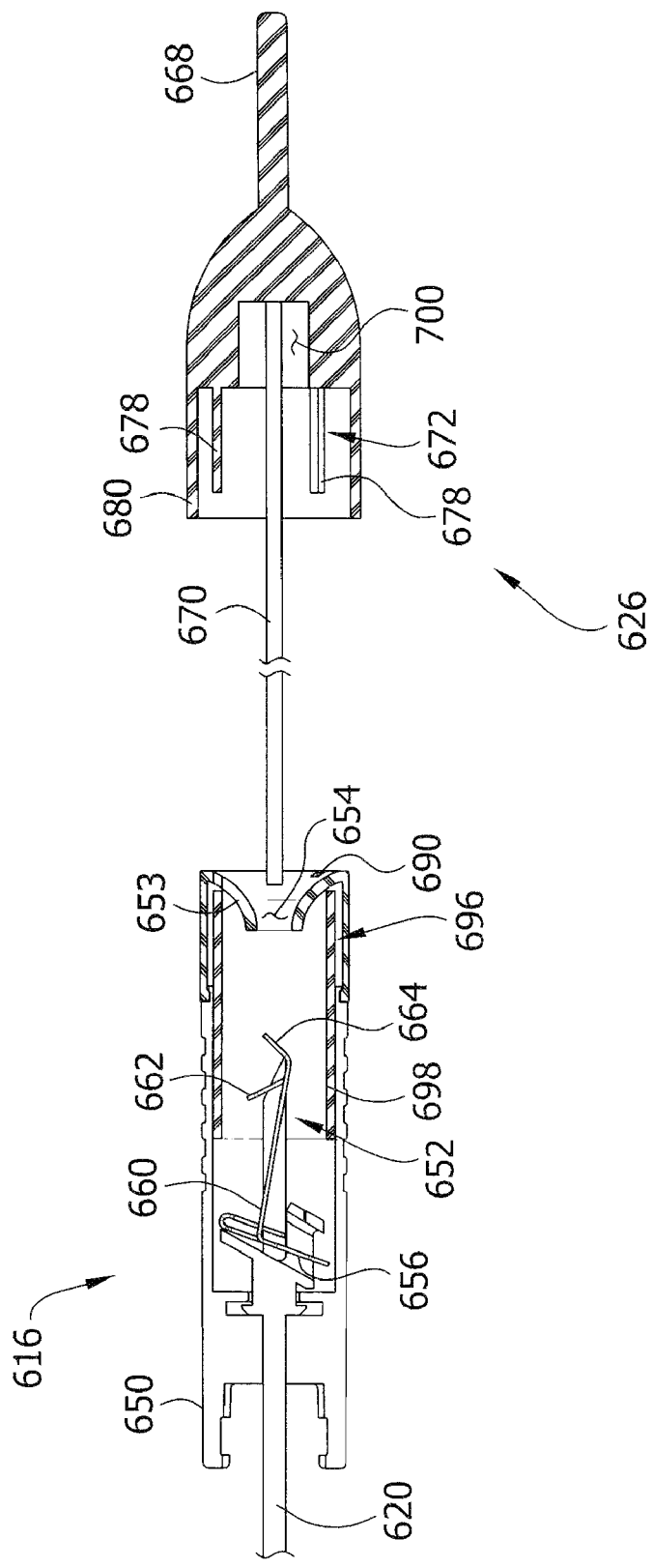
FIG. 29 is a fragmentary partial section of the needle assembly with the obturator entering a safety shield of the needle assembly.

Referring now to FIGS. 28-35, a medical instrument of a sixth embodiment is shown in the form of a bone needle assembly, generally indicated at 610 (FIG. 28). The bone needle assembly includes a handle 612 (broadly, "mounting structure"), a needle 614 and a cannula safety shield 616, all reference numbers indicating their subjects generally. The needle 614 includes a stylet 618 and a cannula 620 that can receive the stylet. The handle 612 includes a first or proximal handle member (indicated generally at 622) mounting the stylet 618, and a second or distal handle member (indicated generally at 624) mounting the cannula 620. It will be understood that a needle could include only a single component part, or more than two parts within the scope of the present invention. Similarly, a handle could be a single part or more than two parts. The mounting structure for the needle 614 can be other than a handle without departing from the present invention. The needle assembly 610 further includes an obturator 626, which is described more fully below, that may be used to remove a sample captured in the cannula 620.

The cannula 620 has a central axial passage extending the length of the cannula and opening at both ends of the cannula. A distal tip 628 of the cannula 620 is beveled and sharpened. A proximal end portion of the cannula 620 is received in the distal handle member 624. The stylet 618 is solid and includes a sharp distal tip, and a proximal end portion of the stylet is received in the proximal handle member 622. The stylet 618 can be inserted through the axial passage opening in the proximal end portion of the cannula 620 and received entirely through the axial passage of the cannula so that its sharp distal tip projects axially outward from the distal tip 628 of the cannula. The stylet 618 provides the tool for penetrating the cortical bone, and can be removed from the cannula 620 once the intramedullary canal is accessed by the needle 614.

The handle 612 formed by the proximal and distal handle members 622, 624 has an ergonomic shape that can be comfortably received in a medical technician's hand, and allows the technician to easily control the needle assembly 610 as he or she applies the substantial forces needed to penetrate the bone. More specifically, the top or proximal surface 638 of the proximal handle member 622 is rounded in conformance with the shape of the palm of the hand. The bottom or distal surface 640 of the distal handle member 624 is also rounded, but is undulating in shape thereby forming finger wells 640A for receiving the technician's fingers. The form of the handle can be other than described herein without departing from the scope of the present invention. The proximal and distal handle members 622, 624 can be connected together in a suitable manner when the stylet 618 is received in the cannula 620, so that the handle 612 acts essentially as a single piece when used to drive the needle 614 through a patient's skin and into the bone. The proximal and distal handle members 622, 624 can be disconnected and moved apart for removing the stylet 618 from the cannula 620.

The cannula safety shield 616 may be moved to cover the distal tip 628 of the cannula 620 after the needle assembly 610 has been used. The safety shield 616 includes a generally tubular housing 650 and an internal locking mechanism (generally indicated at 652 in FIG. 29) capable of releasably locking the tubular housing in position covering the distal tip 628 of the cannula 620. As shown best in FIG. 635, the distal end of the tubular housing 650 includes a funnel-shaped guide 653 leading to an opening 654 directed toward the central axial passageway of the cannula 620. The tubular housing 650 may have any shape that is suitable for hindering access to the sharp tip 628. The tubular housing 650 need not be solid or circular in cross section within the scope of the present invention. The tubular housing 650 and handle 612 may include structure to secure the tubular housing in a retracted position adjacent the handle when not needed. An example of such structure is shown in co-assigned U.S. application Ser. No. 11/146,173, filed Jun 6, 2005, the disclosure of which is incorporated herein by reference.

The locking mechanism 652 inside the safety shield 616 comprises a canting member including a base 656 having a hole and a pair of arms 660 (only one is shown) extending generally axially from the base. The arms 660 are connected together by a U-shaped member 662 at their ends and each has an upwardly (as oriented in the figures) bent tab 664 (only one is shown) projecting axially outward from the end. Before the locking mechanism 652 is activated to lock the tubular housing 650 in position, the ends of the arms 660 ride on the exterior surface of the cannula 620. This holds the canting member so that the base 656 is orthogonal so the longitudinal axis of the cannula 620 and the base can move along the cannula (with the safety shield 616), with the cannula sliding unimpeded through the hole in the base. Once the ends of the arms 660 pass the distal tip 628 of the cannula 620, the locking mechanism 652 is weighted so that the ends of the arms move in a generally radial direction toward an opposite side of the longitudinal axis of the needle 614. This causes the base 656 of the canting member to cant relative to the axis of the needle 614 so that the hole in the base is no longer orthogonal to the axis of the cannula. As a result, the base 656 at the edge of the hole grippingly engages the cannula 620 to lock the safety shield 616 in place. It will be understood that a locking mechanism could take on other forms than shown and described without departing from the scope of the present invention. Moreover, a canting member may take on other configurations (e.g., having only a single arm) within the scope of the present invention.

The needle assembly 610 is driven into the bone by grasping the handle 12 and pushing the stylet 618 through the skin, underlying tissue and cortical bone. Once this penetration has been achieved, the stylet 618 is no longer required. The proximal handle member 622 is disconnected from the distal handle member 624 and moved axially away from the distal handle member so that the stylet 618 slides out of the central axial passageway of the cannula 620 while the cannula remains in the bone. In order to collect a sample of bone marrow, the distal handle member is advanced further into the bone. The sharp tip 628 of the cannula 620 cuts into the bone marrow and a sample is received in the central axial passageway of the cannula. The cannula 620 can then be withdrawn from the patient by pulling on the distal handle member 624. The sample remains lodged in the central axial passageway of the cannula 620 near the sharp tip 628. It will be understood that a needle assembly may be used to collect a sample other than of bone marrow within the scope of the present invention.

The obturator 626 is used to remove a lodged sample of bone marrow that has been collected in the central axial passageway of cannula 620. The obturator 626 includes a grip 668 and a long, thin shaft 670 extending from the grip that is sized to be received in the central axial passageway of the cannula 620 in generally close fitting relation therein. The grip 668 is sized and shaped to be grasped by a user for manipulating the obturator 626, as will be described. As shown best in FIGS. 34 and 35, a reset member, generally indicated at 672, extends from the grip 668 in the same direction as the shaft 670. In the illustrated sixth embodiment, the reset member 672 comprises projecting portions 678 (e.g., three projecting portions) extending from the grip 668 in the same direction as the shaft 6670. The grip 668 further comprises a protective collar 680 extending from the grip 668 to surround the projecting portions 678 and protect the projecting portions from damage. The collar 680 is further adapted to slidably receive the tubular housing 650 in close-fitting relation for proper alignment of the projecting portions 678, as will be discussed in greater detail below with respect to FIG. 31.

Figure 30:
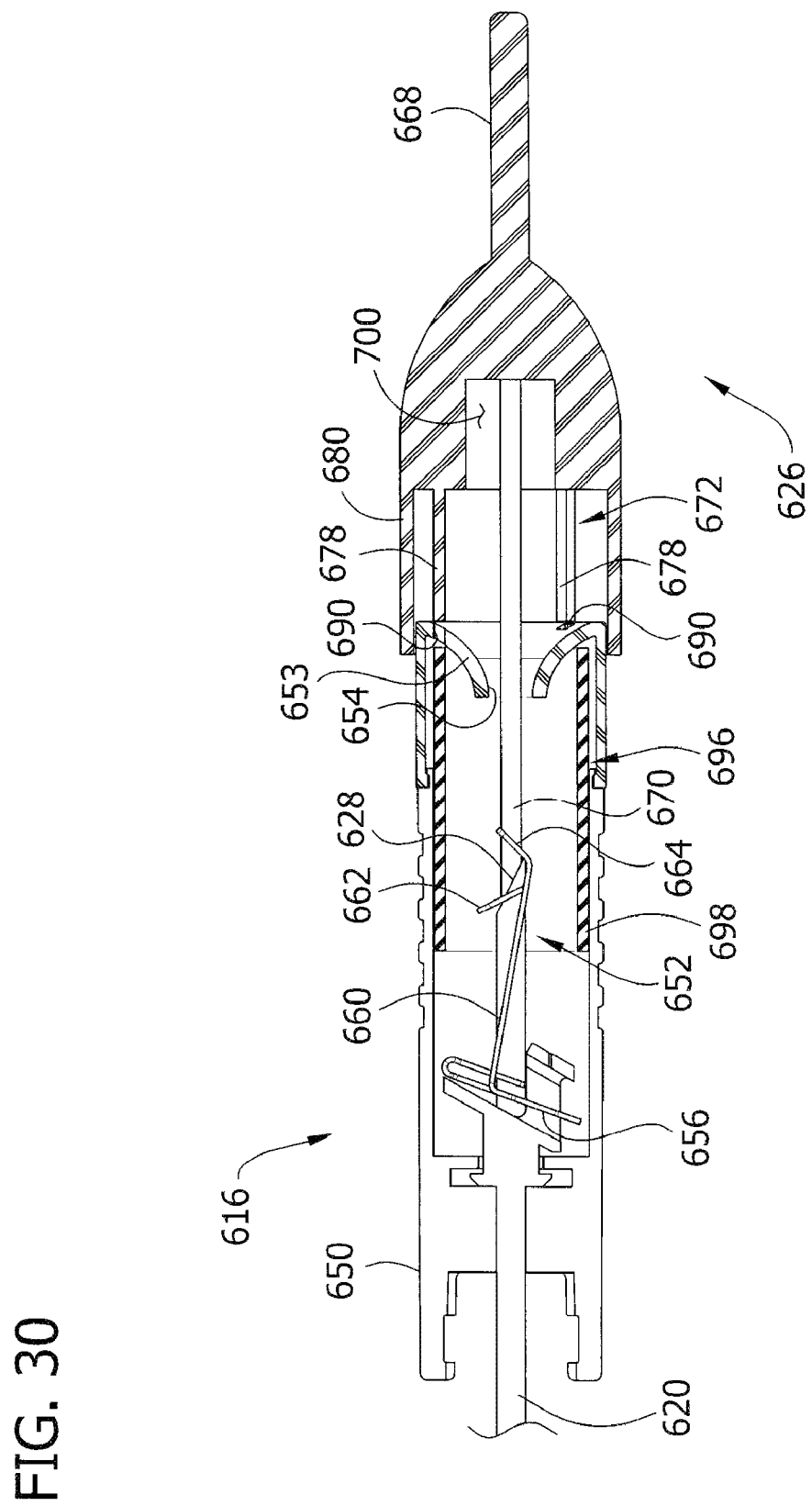
FIG. 30 is the fragmentary elevation of FIG. 29 but showing the obturator inserted to a position in which a sample collected by the needle assembly is pushed out of the needle assembly.
Figure 31:
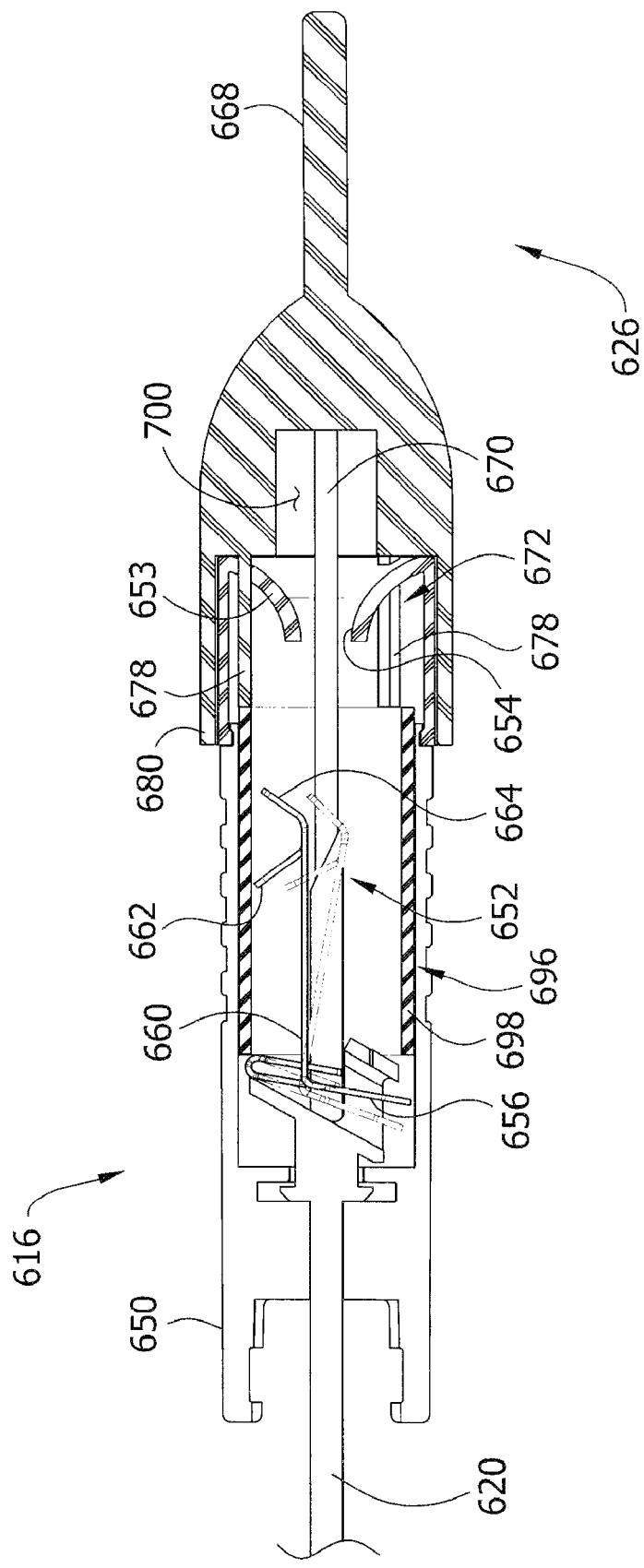
FIG. 31 is the fragmentary elevation of FIG. 29 but showing use of the obturator to reset a locking mechanism of the safety shield.

FIG. 629 illustrates an initial position of the obturator 626 with the shaft 670 entering the distal end of the tubular housing 650. The free end of the shaft 670 has not yet entered the central axial passageway of the cannula 620. As shown best in FIG. 635, the distal end of the tubular housing 650 includes the funnel-shaped guide 653 (broadly, "end wall") for guiding the shaft 670 toward the opening 654 in the funnel-shaped guide leading to the central axial passageway of the cannula 620. The grip 668 is pushed to advance the shaft 670 through the funnel-shaped guide 653 and into the central axial passageway, which pushes the sample toward the proximal end of the central axial passageway. Referring to FIG. 30, the shaft 670 is advanced until it protrudes out of the proximal end of the central axial passageway, thereby pushing the sample (not shown) out of the cannula 620 where it can be collected in a Petri dish or other suitable container. As the shaft 670 is advanced, it slides through the funnel-shaped guide 653 at the distal end of the tubular housing 650. The locking mechanism 652 remains engaged so that the safety shield 616 does not move. In the position shown in FIG. 30, free ends of the projecting portions 678 engage the funnel-shaped guide 653. Thus, the technician experiences a resistance to further inward movement of the shaft 670 into the central axial passageway of the cannula 620 because the funnel-shaped guide 653 is restricting movement of the projecting portions 678 of the obturator 626. As would be readily understood by one skilled in the art, the distal end of the tubular housing 650 may be other than funnel-shaped according to the present invention. For example, the distal end may be generally orthogonal to the central axial passageway (or concave or convex) with an opening leading to the central axial passageway of the cannula 620.

The technician may observe the sample ejected from the central axial passageway of the cannula 620. If it is determined that the sample is satisfactory, the obturator 626 can be pulled so that the shaft 670 slides back through and out of the cannula 620. The needle assembly 610 can be discarded, or possibly but less likely, cleaned and sterilized for a subsequent use. If the sample is not satisfactory, however, it will be necessary to obtain a second sample from the same patient. This can be done using the same needle assembly 610, but the tubular housing 650 is locked in place by the locking mechanism 652 over the sharp tip 628 of the cannula 620. The tubular housing 650 needs to be moved away from the tip 628 before the needle assembly 610 can be used to obtain a second sample.

The obturator 626 of the present invention is particularly adapted to permit the tubular housing 650 to be released and moved back from the sharp tip 628 of the cannula 620, without requiring the technician to remove the contaminated obturator from the cannula. This allows the obturator 626 to be used to both eject the sample and reset the safety shield 616 without utilizing an additional resetting device. This is advantageous because the technician can eliminate the extra steps of removing the obturator, locating the resetting device, and inserting the resetting device. Moreover, removing the obturator 626 is undesirable because it is contaminated and its removal may contaminate surrounding surfaces. It should be understood, however, that even with the benefits of an obturator having resetting capabilities, a device other than an obturator 626 incorporating the resetting, or unlocking, features of the obturator described herein, but not functioning as an obturator, is also contemplated as within the scope of the present invention. From the position shown in FIG. 30, the grip 668 can be advanced toward the tubular housing 650 so that the projecting portions 678 are received into a corresponding number of holes 690 (see FIG. 35) in the funnel-shaped guide 653 of the tubular housing. The holes 690 have a generally rectangular shape corresponding to the cross-sectional shape of the projecting portions 678, although other hole shapes are also contemplated as within the scope of the claimed invention. In the example shown, the holes 690 have a different shape than the opening 654 to encourage a user of the device to correctly insert the cylindrical shaft 670 into the opening and the projecting portions 678 into the holes. The grip 668 and projection portions 678 are rotatable together with respect to the tubular housing 650 about a longitudinal axis of the shaft 670, whereby the obturator 626 may be rotated to a particular angular orientation relative to the tubular housing so that the projecting portions precisely align with respective holes 690. Thus, only at this particular angular orientation will the projecting portions 678 be capable of releasing the locking mechanism 652. Guiding structure (not shown) could be provided to guide the projecting portions 678 into the holes 690.

Figure 35:
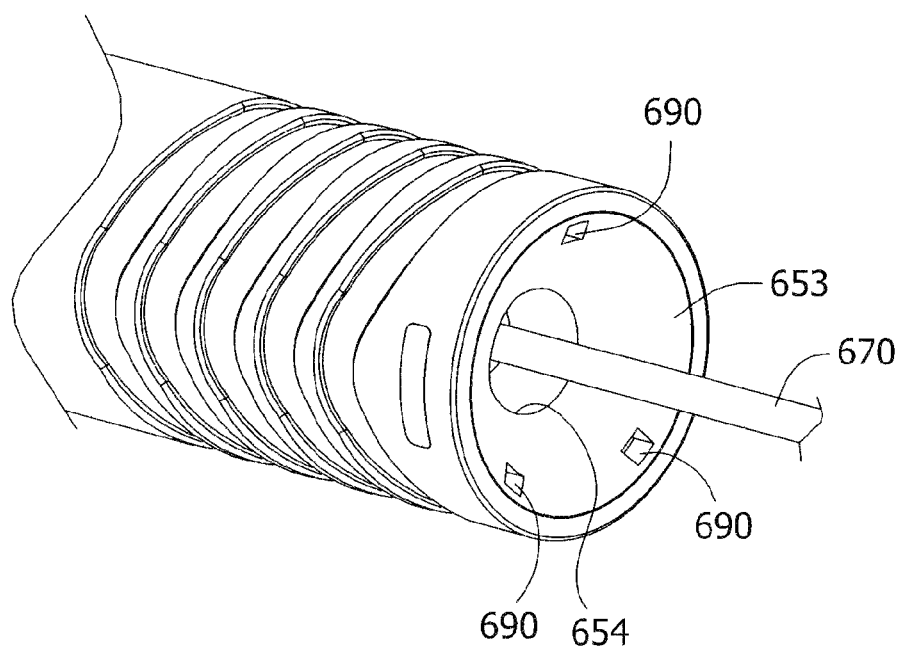
FIG. 35 is a fragmentary perspective of the needle assembly showing the safety shield.
Figure 36:
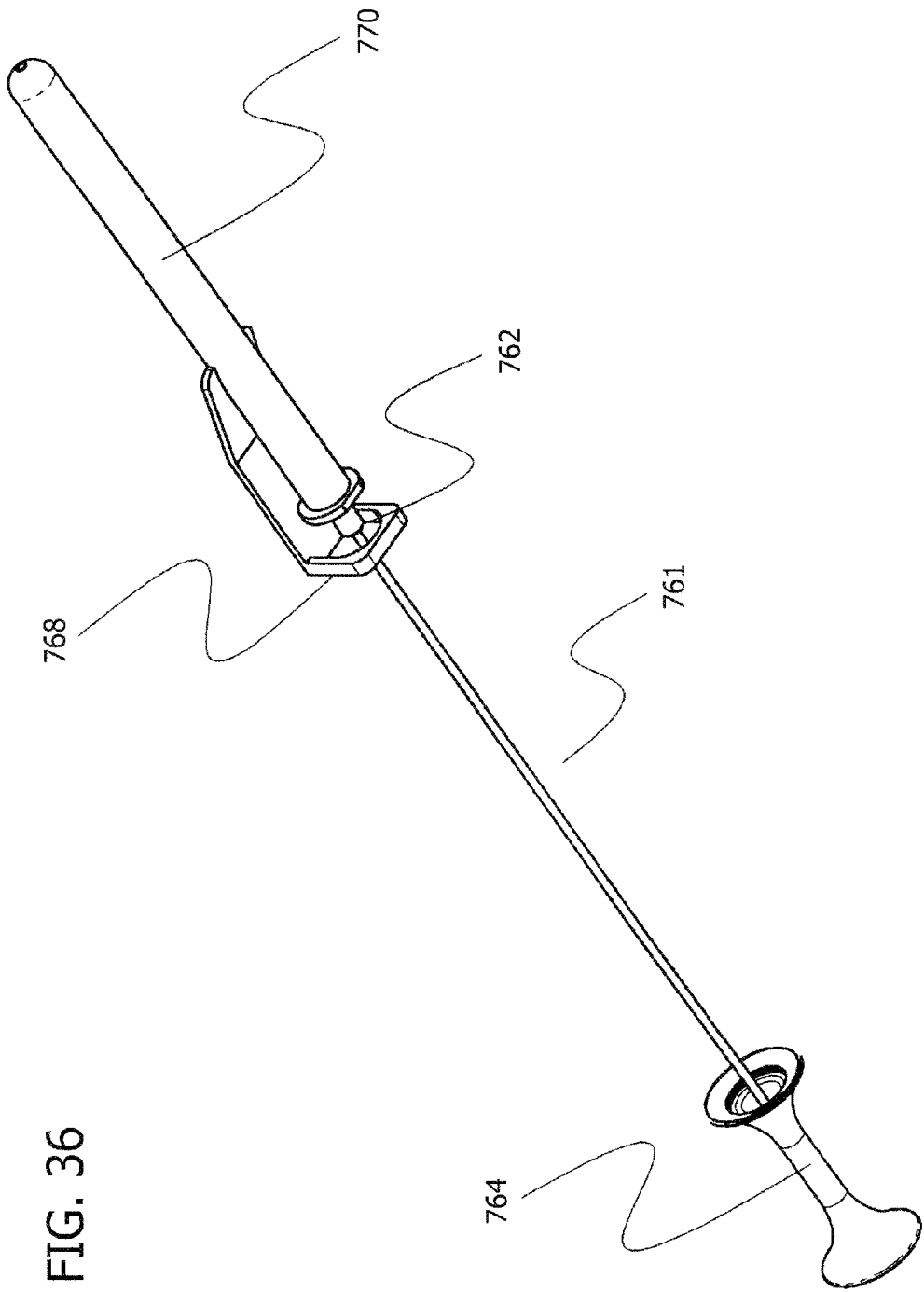
FIG. 36 is a perspective view of an obturator of a needle assembly of a seventh embodiment incorporating an integral funnel guide and reset feature.
Figure 37:
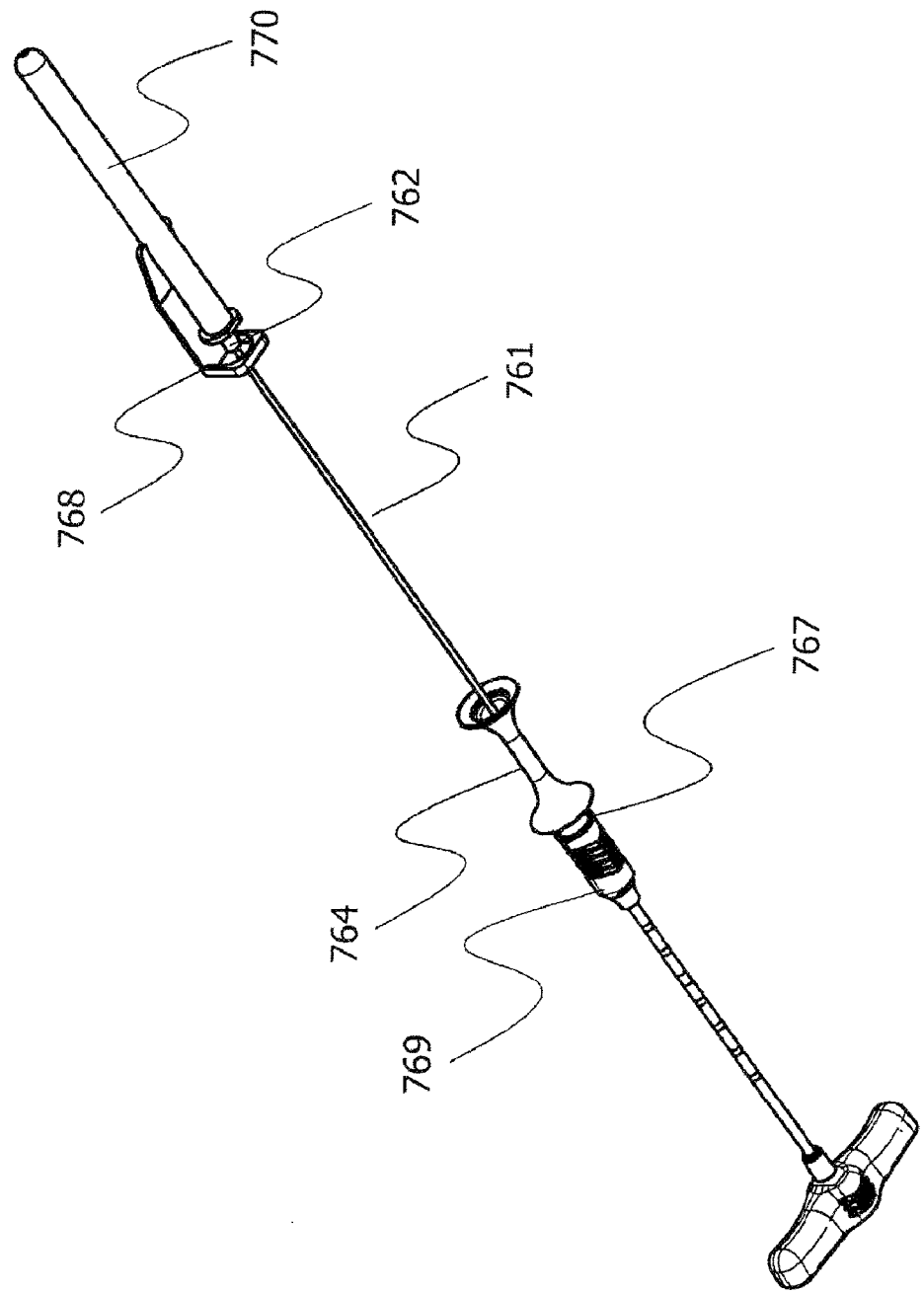
FIG. 37 is a perspective view of the obturator of FIG. 36 and another part of the needle assembly during resettable engagement.
Figure 38:
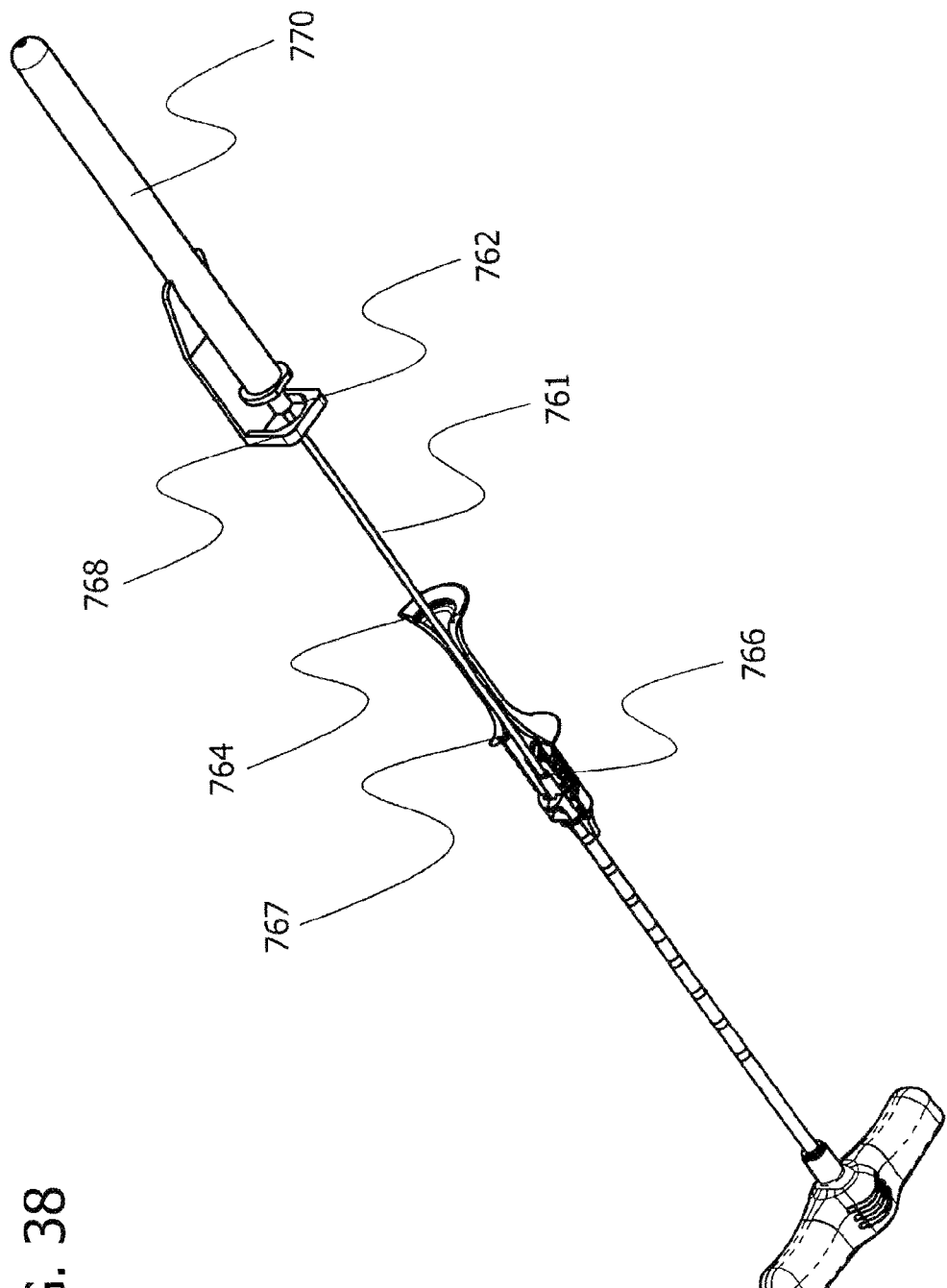
FIG. 38 is the perspective of FIG. 37 with parts broken away to show internal construction.
Figure 39:
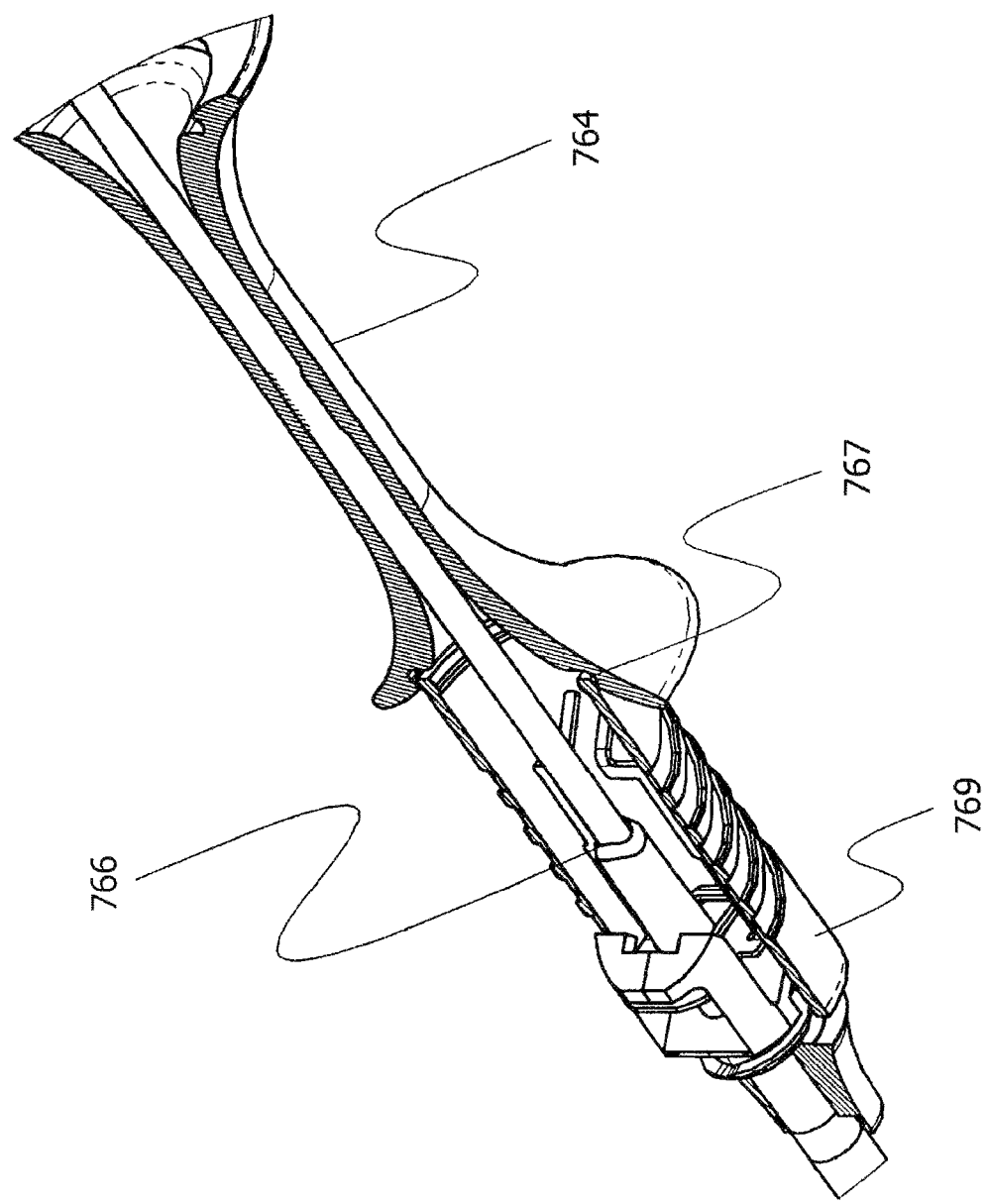
FIG. 39 is an enlarged fragment of the perspective of FIG. 37.
Figure 40:
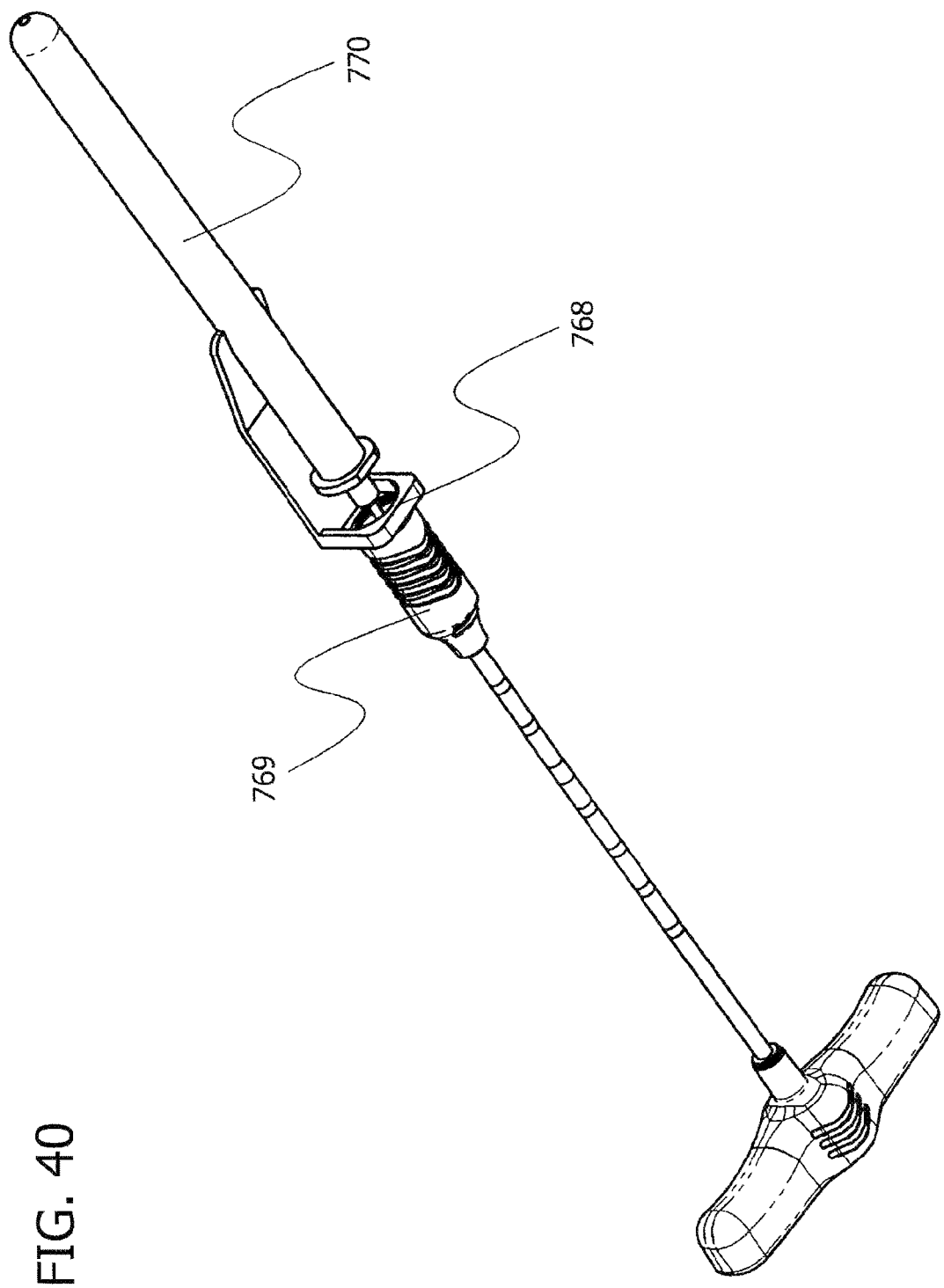
FIG. 40 is the perspective of FIG. 37 with the obturator inserted through a needle of the needle assembly.
Figure 41:
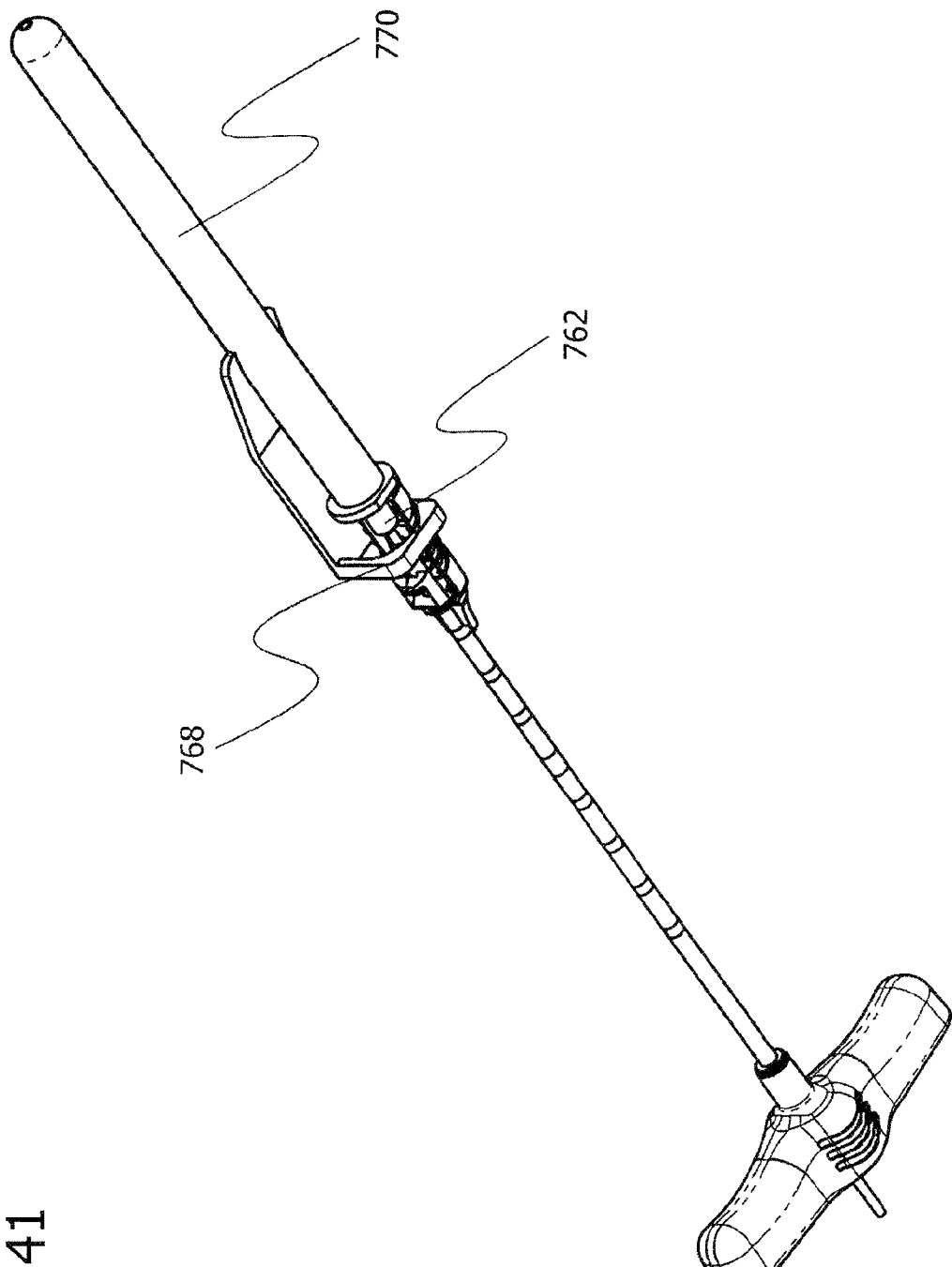
FIG. 41 is the perspective of FIG. 40 with parts broken away to show internal construction.
Figure 42:
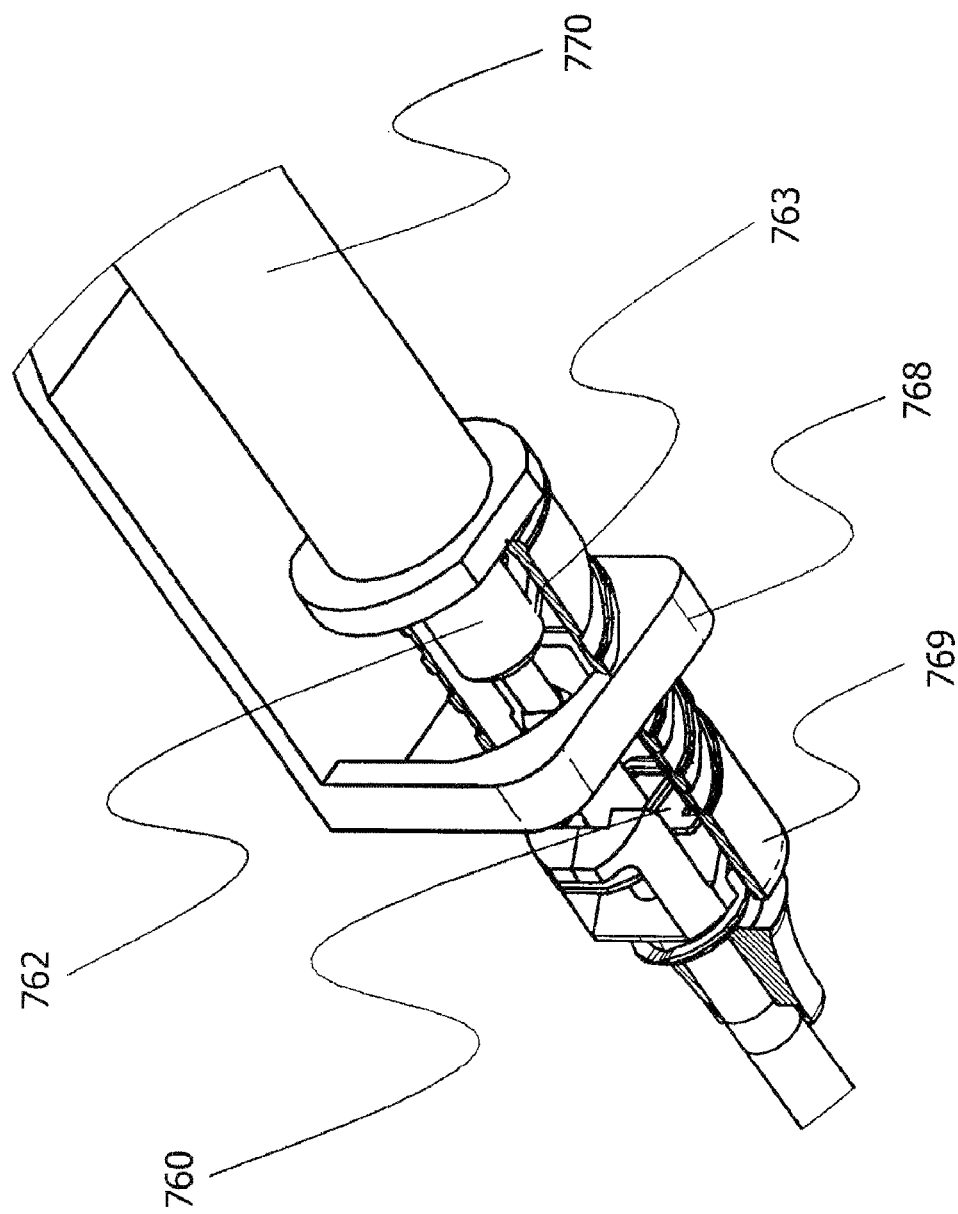
FIG. 42 is an enlarged fragment of the perspective of FIG. 41.
Figure 43:
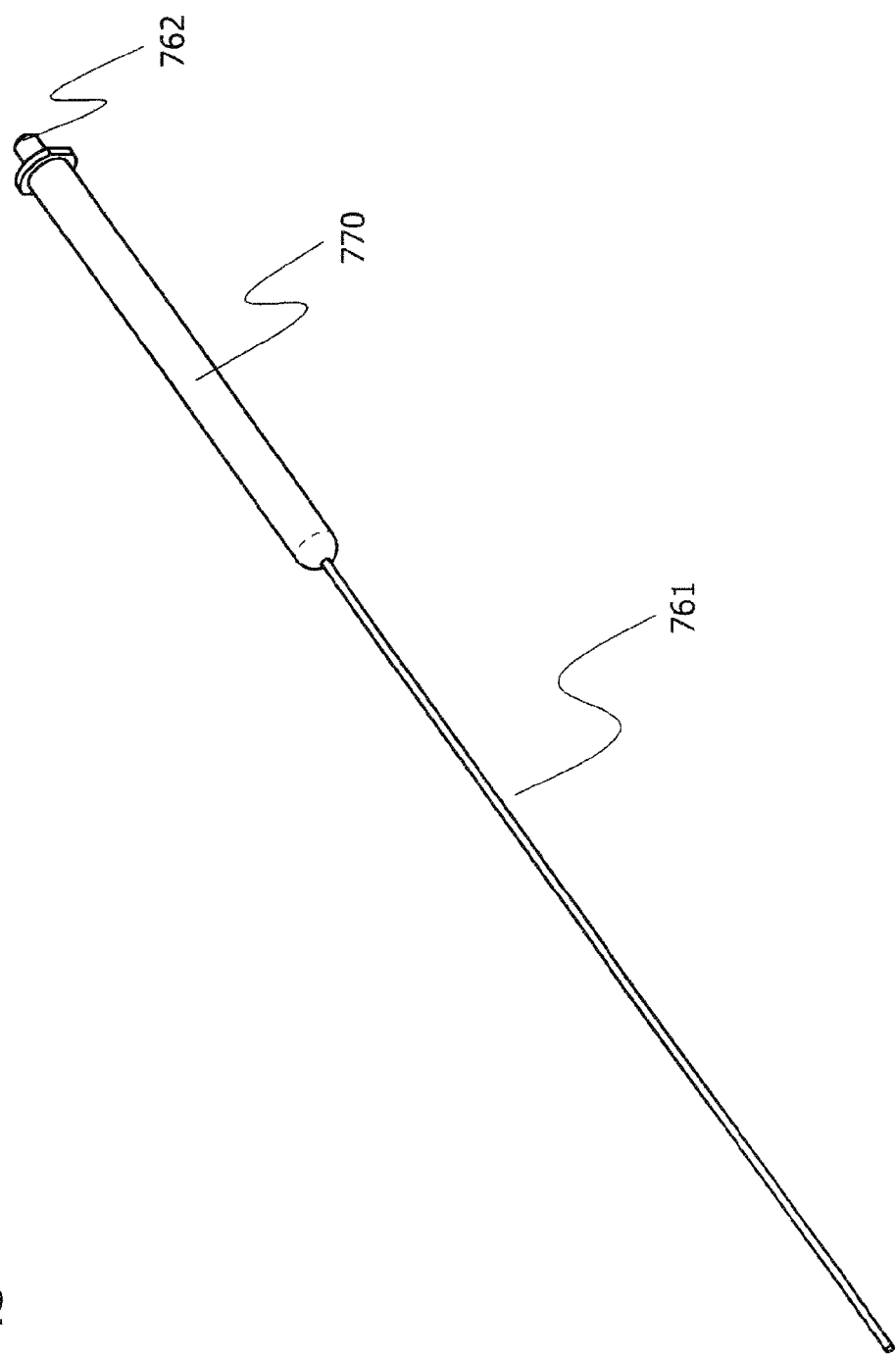
FIG. 43 is a perspective view of an obturator.
Figure 44:
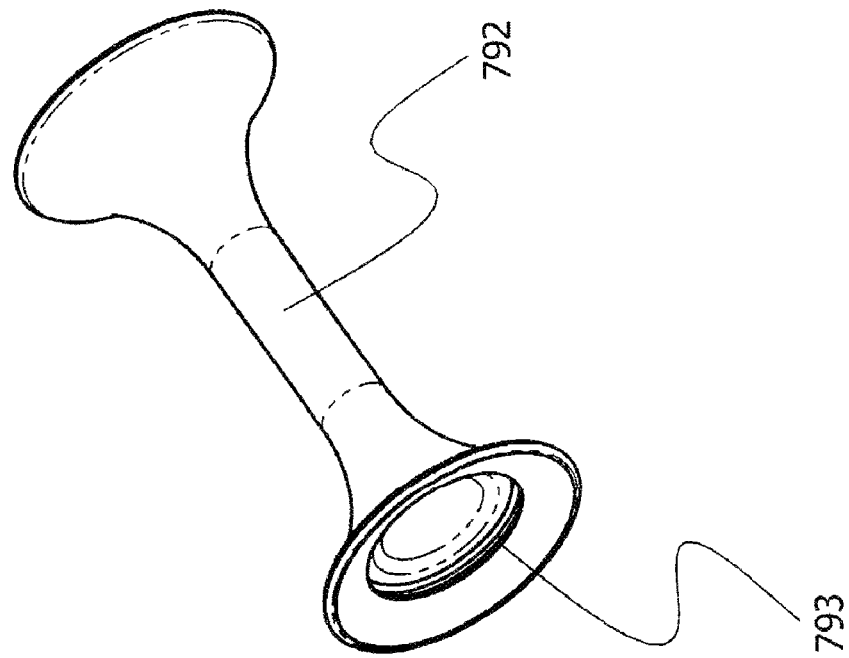
FIG. 44 is a perspective view of a funnel for guiding an obturator.
Figure 45:
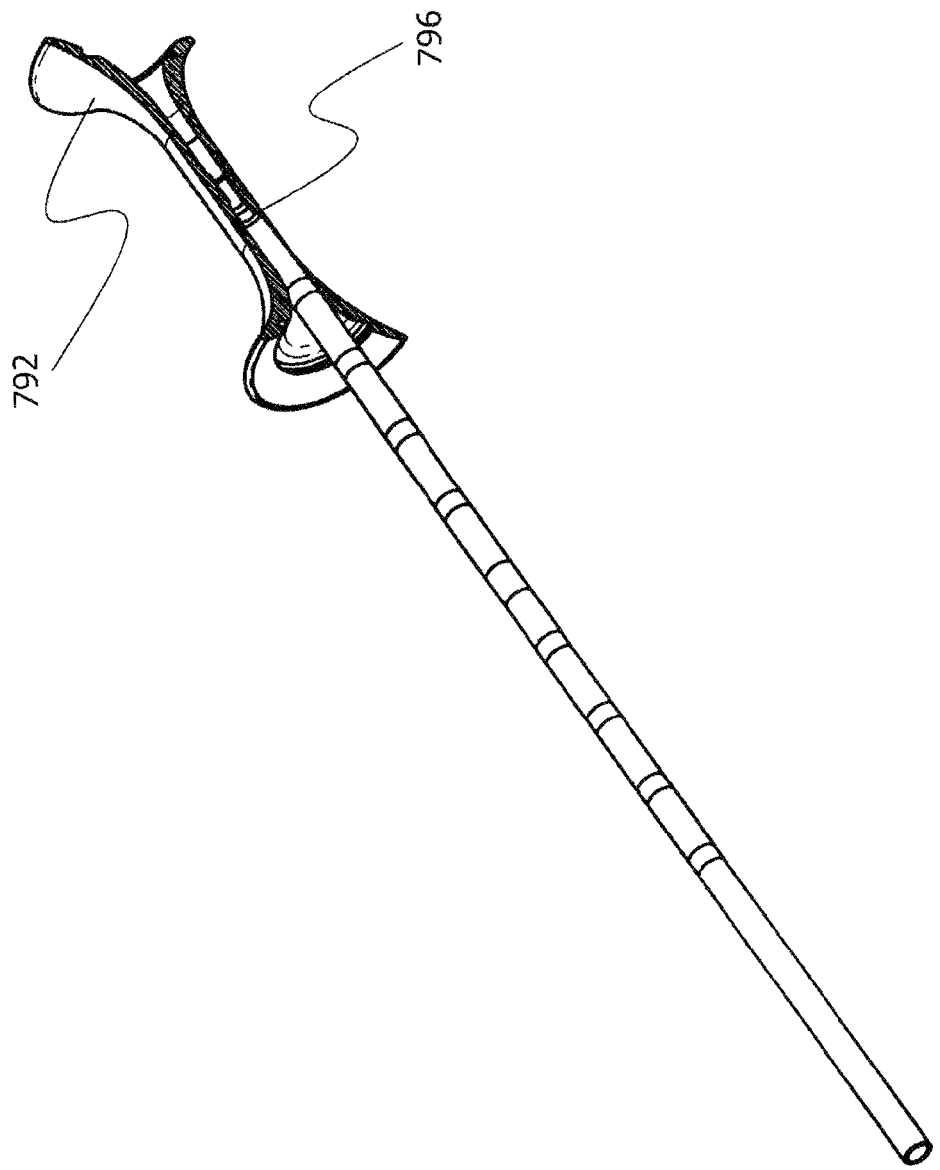
FIG. 45 is a cutaway view of a funnel placed over a needle.
Figure 46:
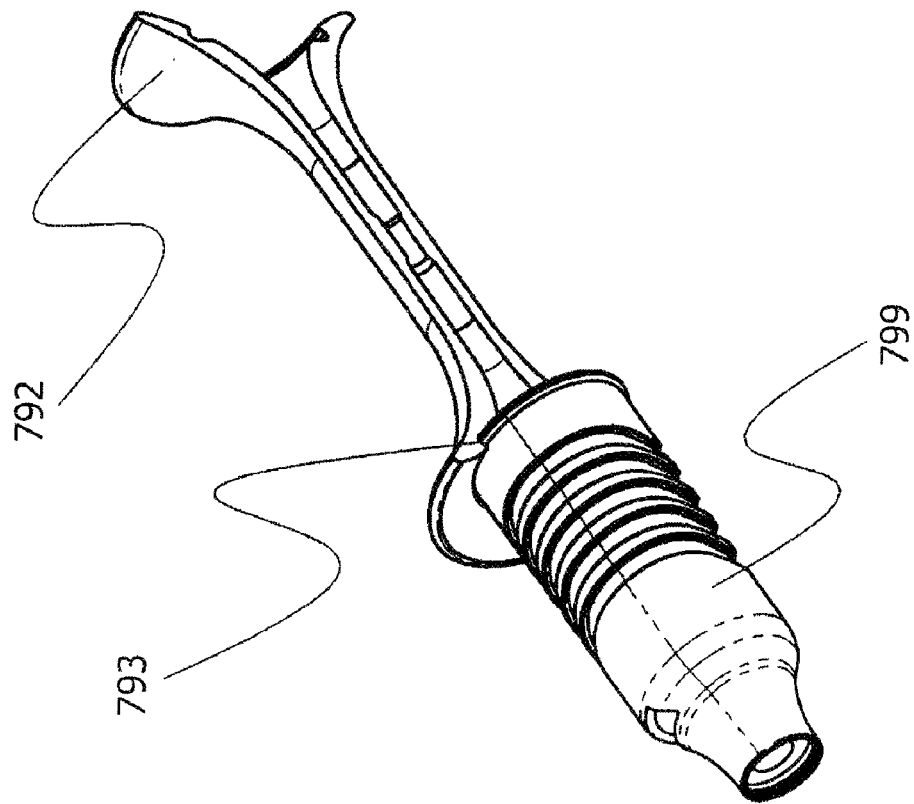
FIG. 46 shows locating features on the safety shield for guiding the obturator to the inner diameter of the needle.
Figure 47:
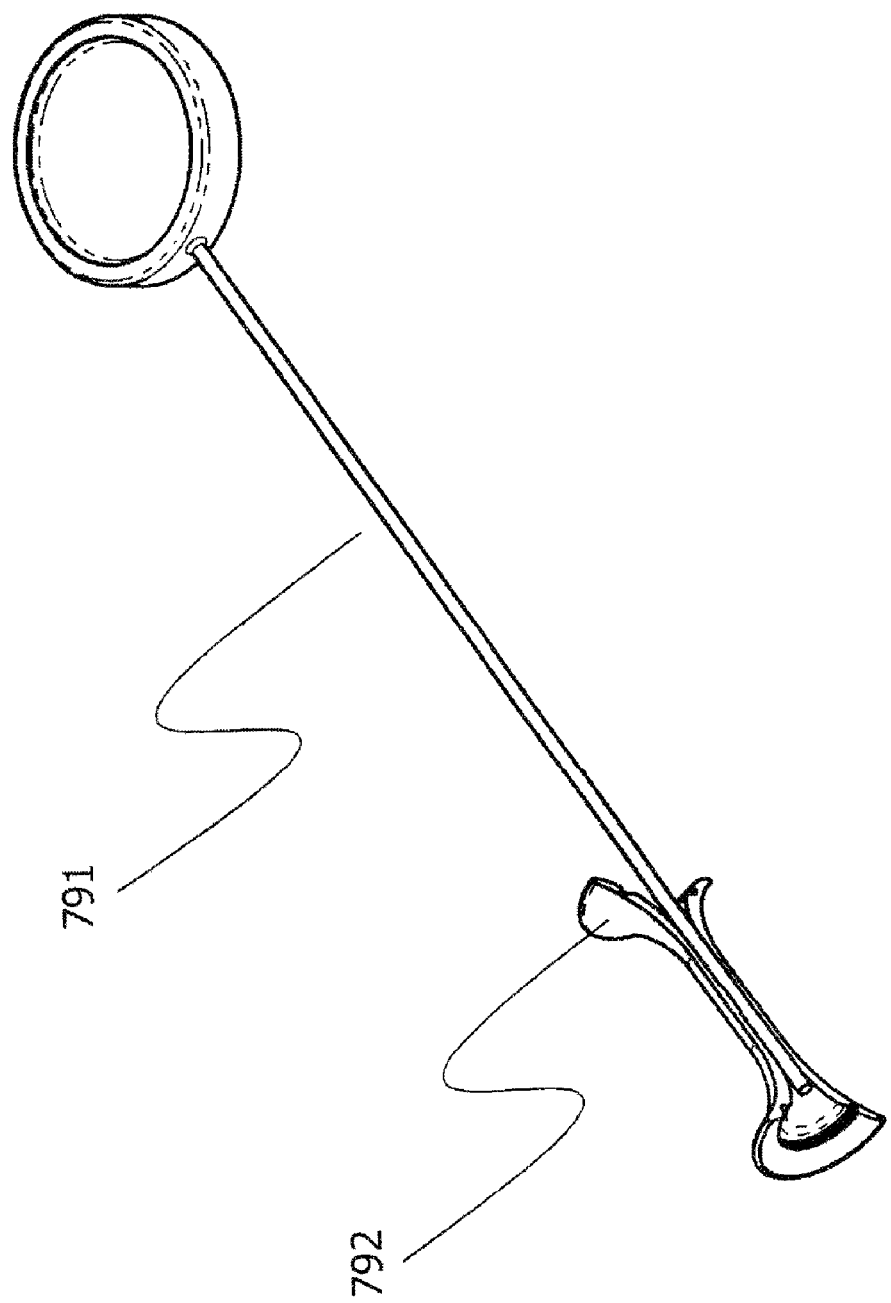
FIG. 47 shows an obturator inserted into a funnel.
Figure 48:
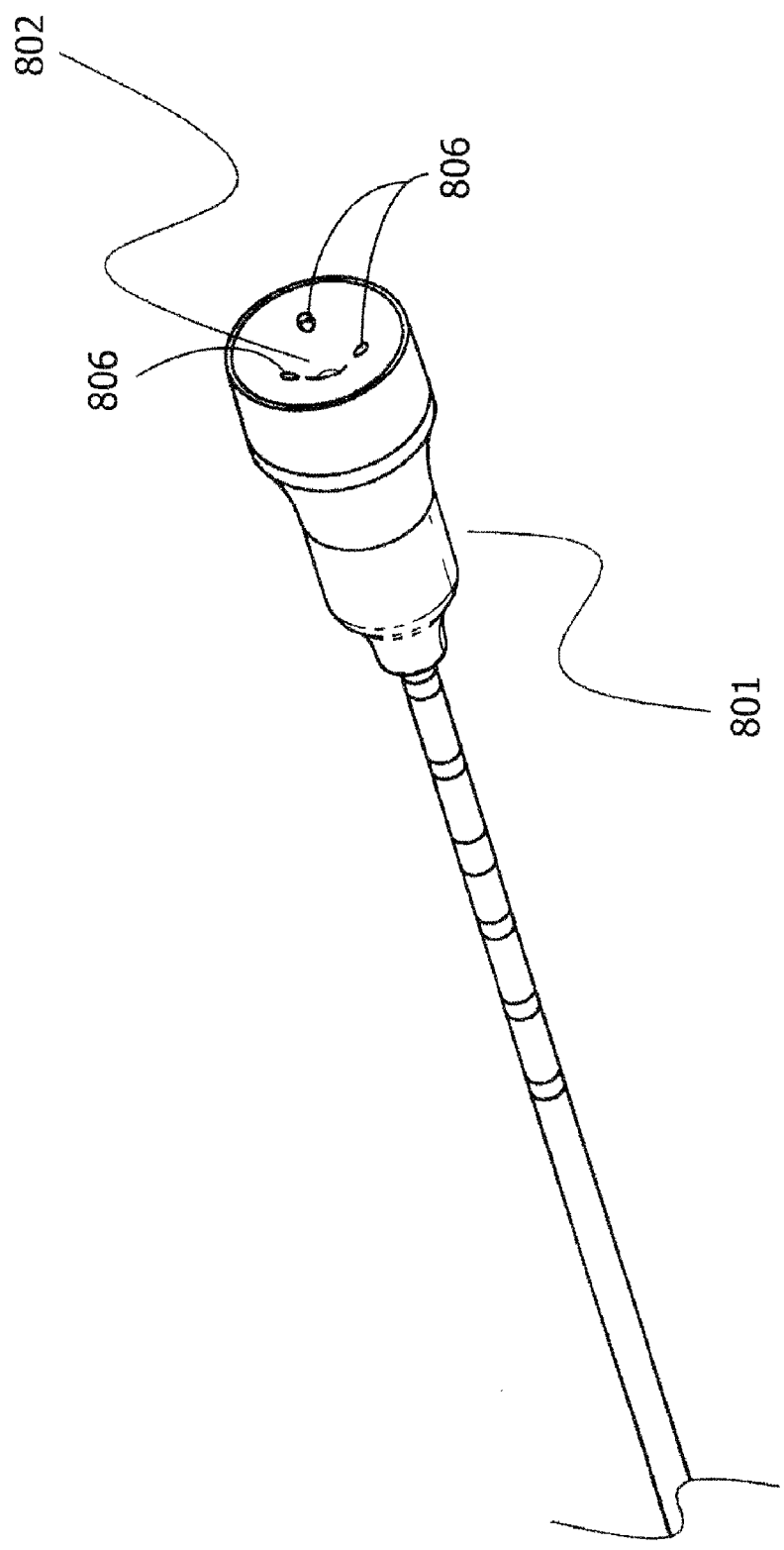
FIG. 48 is a perspective view of an alternative embodiment of the medical needle shield apparatus according to the present disclosure.
Figure 49:
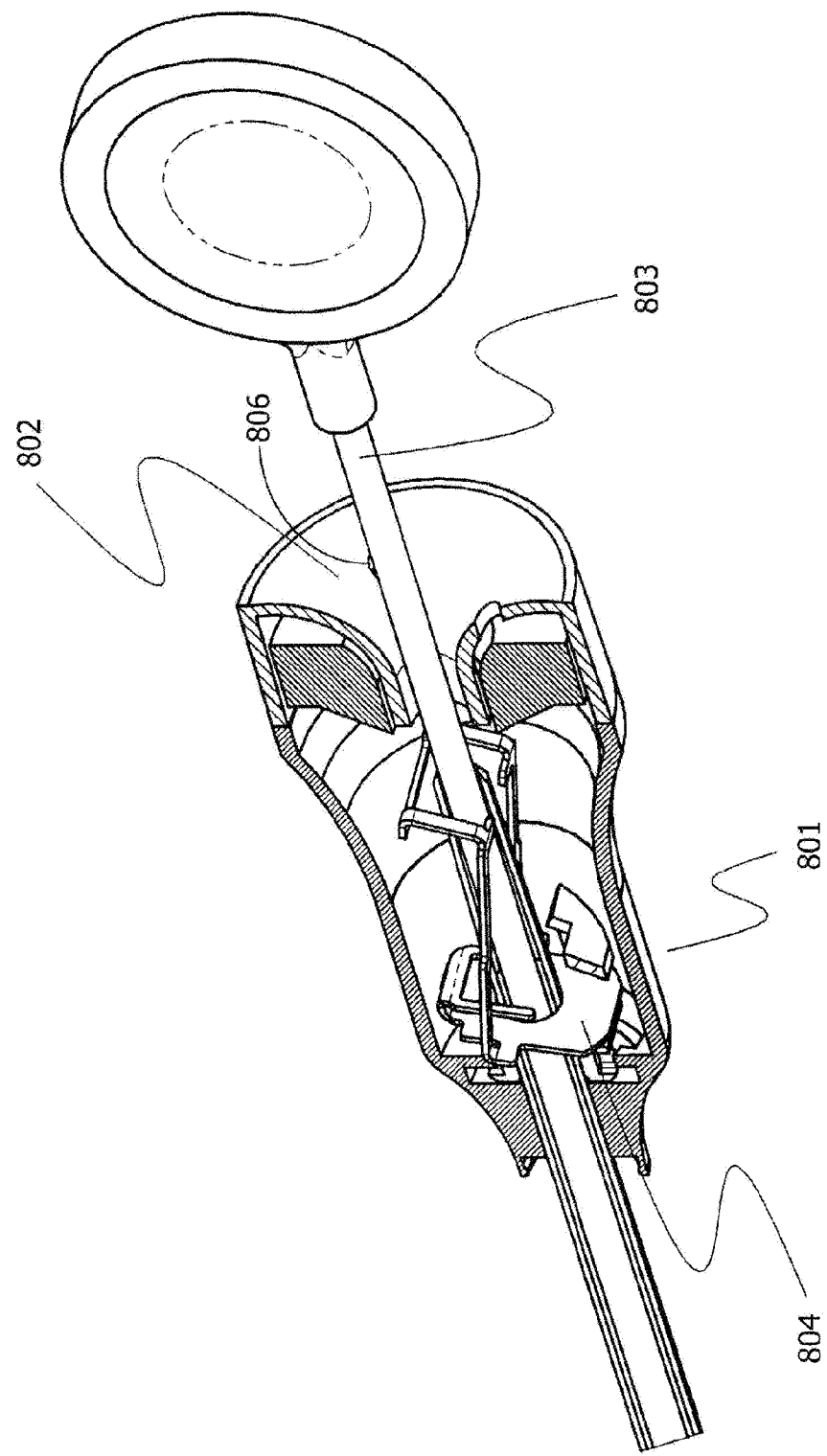
FIG. 49 is a cutaway view of the embodiment shown in FIG. 48.

As depicted in the example of FIG. 35, three holes 690 of the tubular housing 650 are arranged in a pattern having a first order rotational symmetry. In other words, the holes 690 of the tubular housing 650 (FIG. 35) and the projecting portions 678 of the obturator 626 (FIGS. 33 and 34) will only fit together in one angular orientation. In another example (not shown), the holes 690 and projection portions 678 may be located at 120 degree intervals relative one another, providing third order rotational symmetry, whereby the holes of the tubular housing 650 and the projecting portions of the obturator 626 may fit together in three distinct angular orientations. Other orders of rotational symmetry (e.g., second, fourth, fifth, etc.) including a fewer or greater number of projection portions 678 and holes 690 are also contemplated as within the scope of the claimed invention. Generally, a higher order of rotational symmetry provides more angular orientations where the holes 690 of the tubular housing 650 and the projecting portions 678 of the obturator 626 will fit together for unlocking the safety shield 616. It should be understood that the cross-sectional areas and shapes of the projecting portions 678 and holes 690 need not be the same, as long as the holes are large enough to receive corresponding projecting portions. Other means for requiring a particular orientation of the obturator 626 with respect to the tubular housing 650 for releasing the locking mechanism 652 are also contemplated as within the scope of the claimed invention (e.g., corresponding collar and tubular housing shapes, mating channels, etc.).

The safety shield 616 further comprises an unlocking mechanism, generally indicated 696, for selective, movable engagement with the locking mechanism 652 for releasing the locking mechanism to permit the tubular housing 650 to move away from the sharp end 628 of the cannula 620. The unlocking mechanism 696 is movable between a first position in which it is free to lock the safety shield 616 in position relative to the sharp end 628 of the cannula 620 and a second position in which the unlocking mechanism releases the locking mechanism 652 to permit movement of the safety shield relative to the sharp end of the cannula. In one example, the unlocking mechanism 696 comprises a generally rigid body such as a cylindrical sleeve 698, or other annular shape, slidably enclosed within and supported by the tubular housing 650 for movement relative to the tubular housing and the locking mechanism 652. In the example shown, the sleeve 698 moves freely within the tubular housing 650, although connections between the sleeve and the tubular housing or the sleeve and the base 656 are also contemplated as within the scope of the invention. Moreover, the sleeve 698 may be biased away from the base 656 to inhibit inadvertent release of the locking mechanism 652. With the projecting portions 678 aligned with the holes 690, the grip 668 can be advanced toward the tubular housing 650 so that the projecting portions 678 pass through the holes 690 and into the tubular housing to engage the sleeve 698 for movement of the sleeve toward the base 656 of the canting member. During advancement of the grip 668, the collar 680 slidably, yet snugly, receives the tubular housing 650 in relatively close engagement to minimize canting of the collar with respect to the tubular housing, thereby facilitating proper alignment of the projecting portions 678 within the holes 690. Moreover, as a leading edge free portion of the sleeve 698 engages the base 656 of the canting member, the sleeve wedges the base of the canting member up to a position in which the base is again substantially orthogonal to the axis of the cannula 620, as shown in phantom in FIG. 31. This positions the hole in the base 656 so that the cannula 620 can slide easily through the canting member. In another example, the sleeve 698 may engage another portion of the canting member (e.g., the bent tab 664) to reset the canting member, without departing from the scope of the claimed invention.

Figure 32:
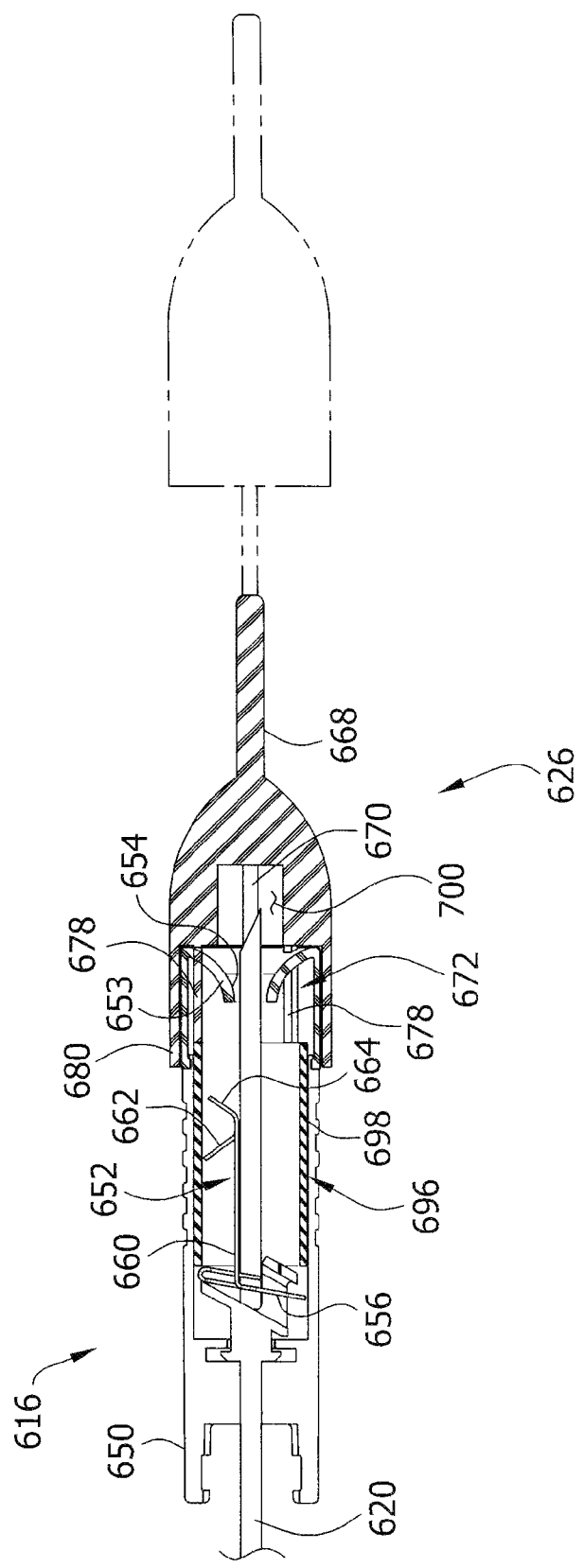
FIG. 32 is the fragmentary elevation of FIG. 29 but showing the safety shield being withdrawn from a sharp end of the needle assembly after release of the locking mechanism.
Figure 33:
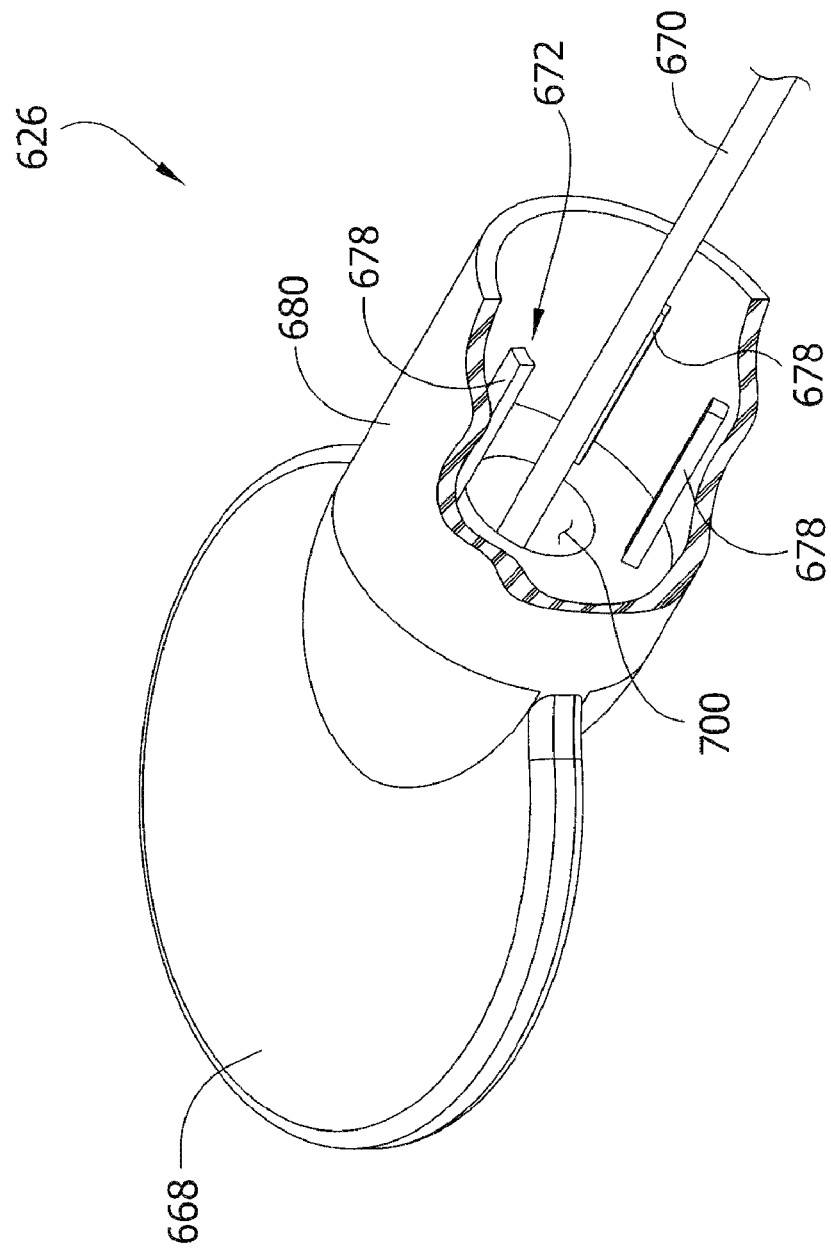
FIG. 33 is a fragmentary perspective of the obturator with parts broken away to show internal construction.
Figure 34:
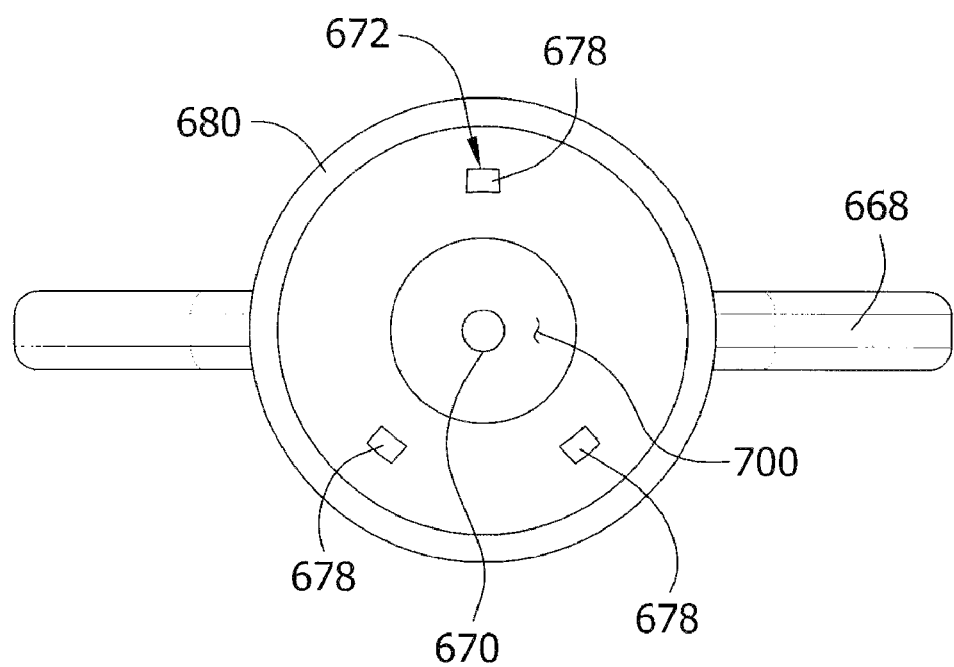
FIG. 34 is an end view of the obturator.

Thus, as shown in FIG. 32, the tubular housing 650 can be grasped to pull back the safety shield 616 toward the distal housing member 624 so that the sharp tip 628 of the cannula 620 can be exposed. The obturator shaft 670 can be removed, as shown in phantom in FIG. 32, and the stylet 618 can be reinserted into the cannula 620 for a second collection of a sample. It will be appreciated that the arrangement of the projecting portions 678 and holes 690 such that only one angular orientation of the obturator 626 will unlock the locking mechanism 652 inhibits the accidental release of the locking mechanism. The technician must intentionally align the projecting portions 678 and holes 690 to de-activate the locking mechanism 652. In this manner, the funnel-shaped guide 653 acts as a reset inhibitor by only permitting de-activation the locking mechanism 652 with proper alignment of the projecting portions 678 and the holes 690.

As would be readily understood by one skilled in the art, the grip 668 may additionally comprise a cavity 700 opposite the open collar 680 and projecting portions 678 for accommodating the portion of the cannula 620 extending from the distal end of the tubular housing 650 when the projecting portions have fully extended into the holes 690 of the tubular housing.

Referring to FIGS. 36-63, there are illustrated additional embodiments of the present invention incorporating a resettable feature. As shown in FIGS. 36-43, an obturator 761 having reset geometry 762 ("a reset member") interacts with a reset element 763.

The obturator 761 may have a handle 770. The handle 770 may include a cavity 765 to protect the needle 766 during resetting. The obturator 761 may also include a funnel 764 to guide the obturator 761 through the safety shield 769 to the inner diameter of the needle 766. The funnel 764 may include locating surfaces 767 on the housing to facilitate guiding. The funnel 764 is slidable along the obturator 761 such that the funnel 764 allows the obturator 761 to pass through the funnel 764. The funnel 764 may be a separate piece. The obturator 761 may also include a blocking element 768 positioned to prevent resetting. The blocking element 768 may also be movable relative to the obturator 761 so that the blocking element 768 may receive the safety shield 769 through the blocking element to allow the resetting geometry 762 to interact with the reset element 763. The means for moving the blocking element 768 includes, but is not limited to, levers, hinges, buttons, locks, snaps, detents, etc.

In this embodiment the obturator 761 is configured such that after the obturator 761 is through the needle 766 and expels a sample, the blocking element 768 in a blocking position engages the safety shield 769 and precludes the resetting geometry 762 from interacting with the reset element 763.

The blocking element 768 is then moved to a non-blocking position such that the resetting geometry 762 interacts with the reset element 763. The resetting geometry 762 interacts with the reset element 763 such that the binding member 760 is released from a locked position. This allows the safety shield 769 to be ready for reuse. It is also envisioned that the resetting geometry 762 may be placed in other locations on the obturator 761 including, but not limited to, the opposite end of the obturator 761.

As illustrated in FIGS. 44-47, a funnel 792 guides an obturator 791 to the inner diameter of a needle 796. The funnel 792 may be configured such that it allows for a locking or friction fit to the needle 796. The funnel 792 may also be configured such that it incorporates locating features 793 on the safety shield 799 for guiding the obturator 791 to the inner diameter of the needle 796. The locating features 793 on the safety shield 799 may also be configured such that a desirable fit is accomplished to maintain position. Such fit interfaces include, but are not limited to, snap fit, friction fit, detents, etc.

The option to use the funnel 792 with or with out the safety shield 799 may be desirable so that clinicians may choose to use the funnel 792 with the safety shield 799 protecting the contaminated sharp to guide an obturator 791 to the inner diameter of the needle 796. This also allows for conventional use without safety devices.

Referring to FIGS. 48-63, in certain applications it may be desirable to funnel an obturator through the needle device. It may also be desirable to incorporate this guiding member in a safety shield, which may require activation of the safety shield prior to using the funnel. Furthermore, it may be desirable to reset a binding member that protects a contaminated sharp (e. g. medical needle, stylet, etc.).

One embodiment illustrates a guiding member 802 that is integral to the safety shield 801. The guiding member 802 includes an interface of a particular geometry that allows for guiding a through-the-needle device, such as an obturator 803, etc. The guiding member 802 is configured such that the through-the-needle device 803 cannot interfere with the locking mechanism 804 in the safety shield 801. Other embodiments include a geometry that continues to allow for guiding of guiding member 802, but which also provides reset areas 806 for the safety shield 801.

Figure 50:
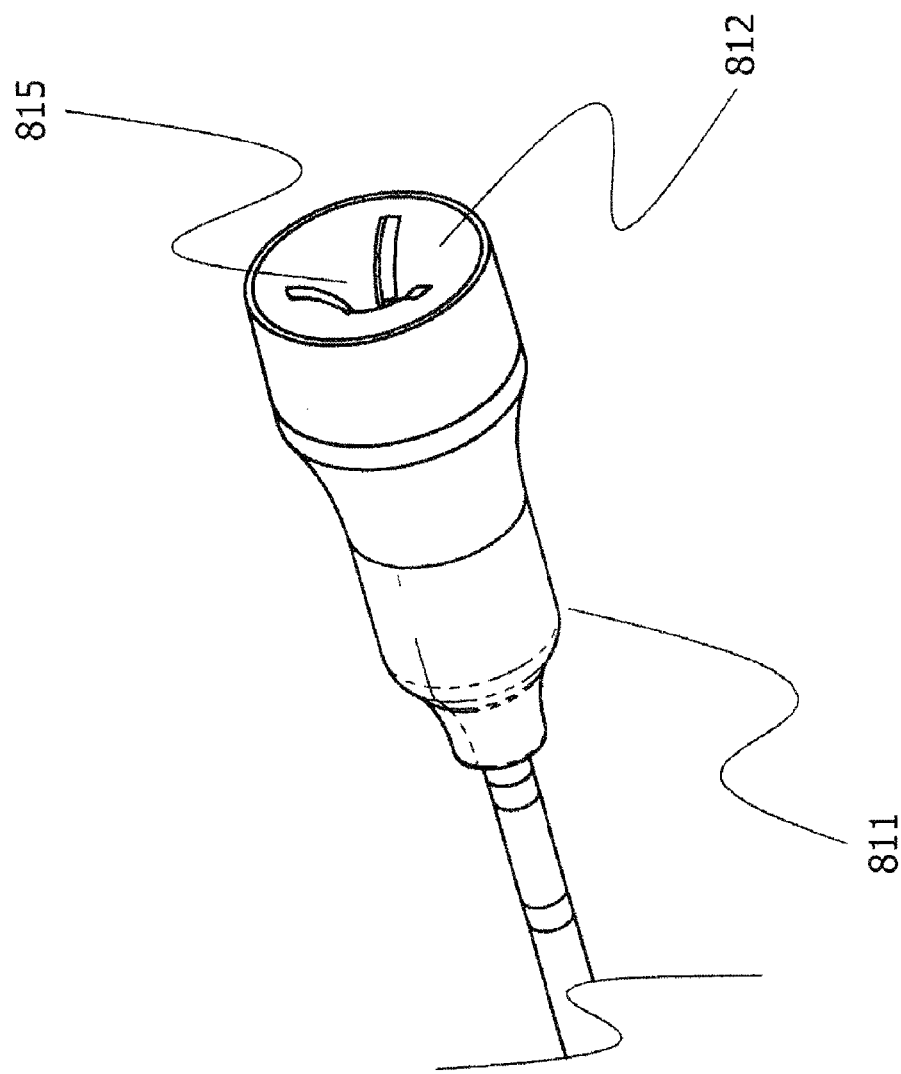
FIG. 50 is an enlarged view of the safety shield of the embodiment shown in FIG. 48.
Figure 51:
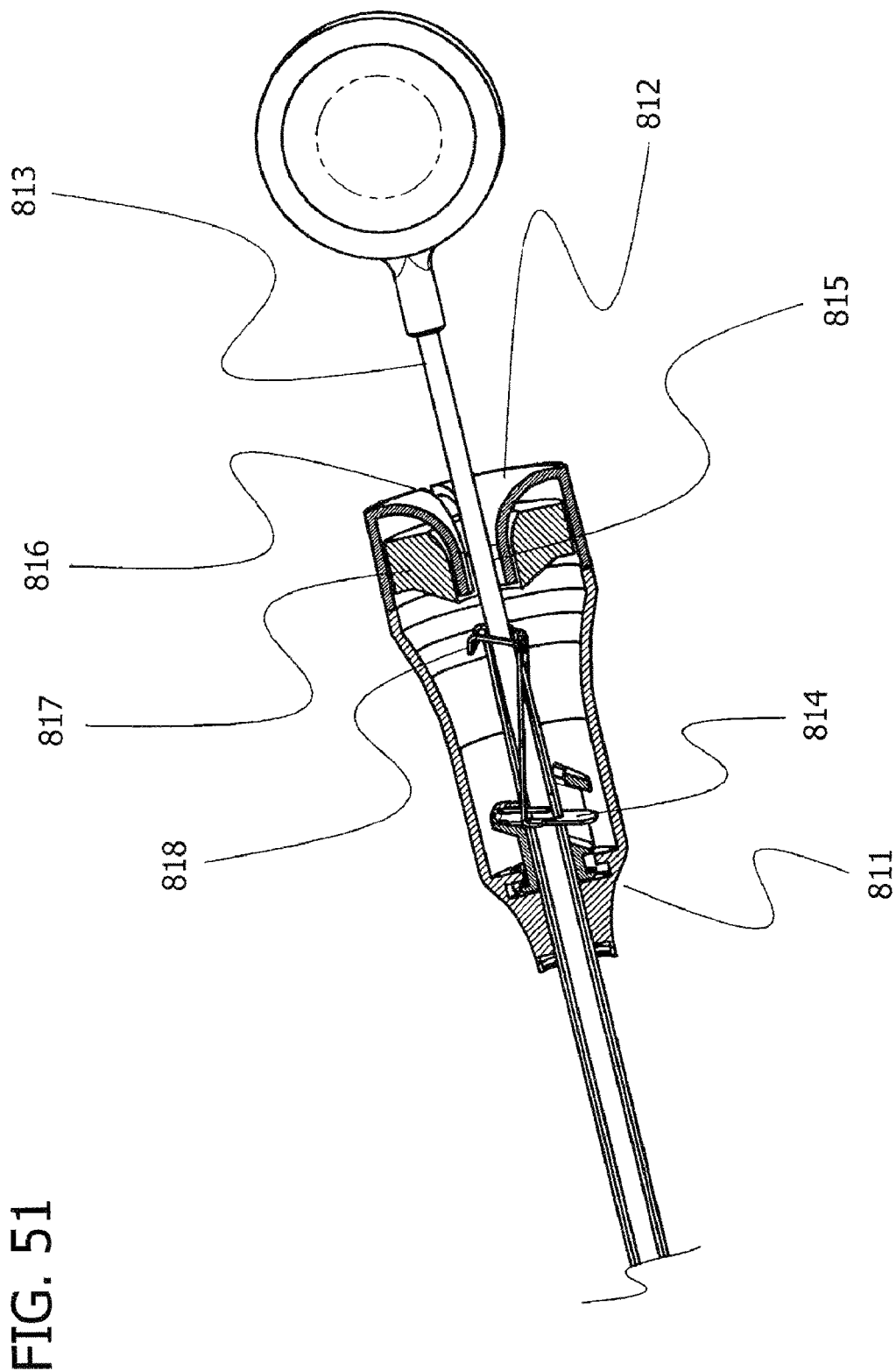
FIG. 51 is a cutaway view of the safety shield having a needle inserted.

FIGS. 50-51 show a guiding member 812 having flexible members 815 allowing the guiding member 812 to change sizes. This allows for guiding of a through the needle device 813 (e.g., an obturator). The flexible members 815 also allow for a larger opening that provides a reset area 816. The reset area 816 is an area that will allow reset geometry 817 ("reset member"), or other geometry that interacts with the reset geometry 817, to be brought into a position such that it interacts with the reset element 818 to allow the locking mechanism 814 to be released from binding the safety shield 811 in place on the needle. This allows for the safety shield 811 to be ready for reuse.

Figure 52:
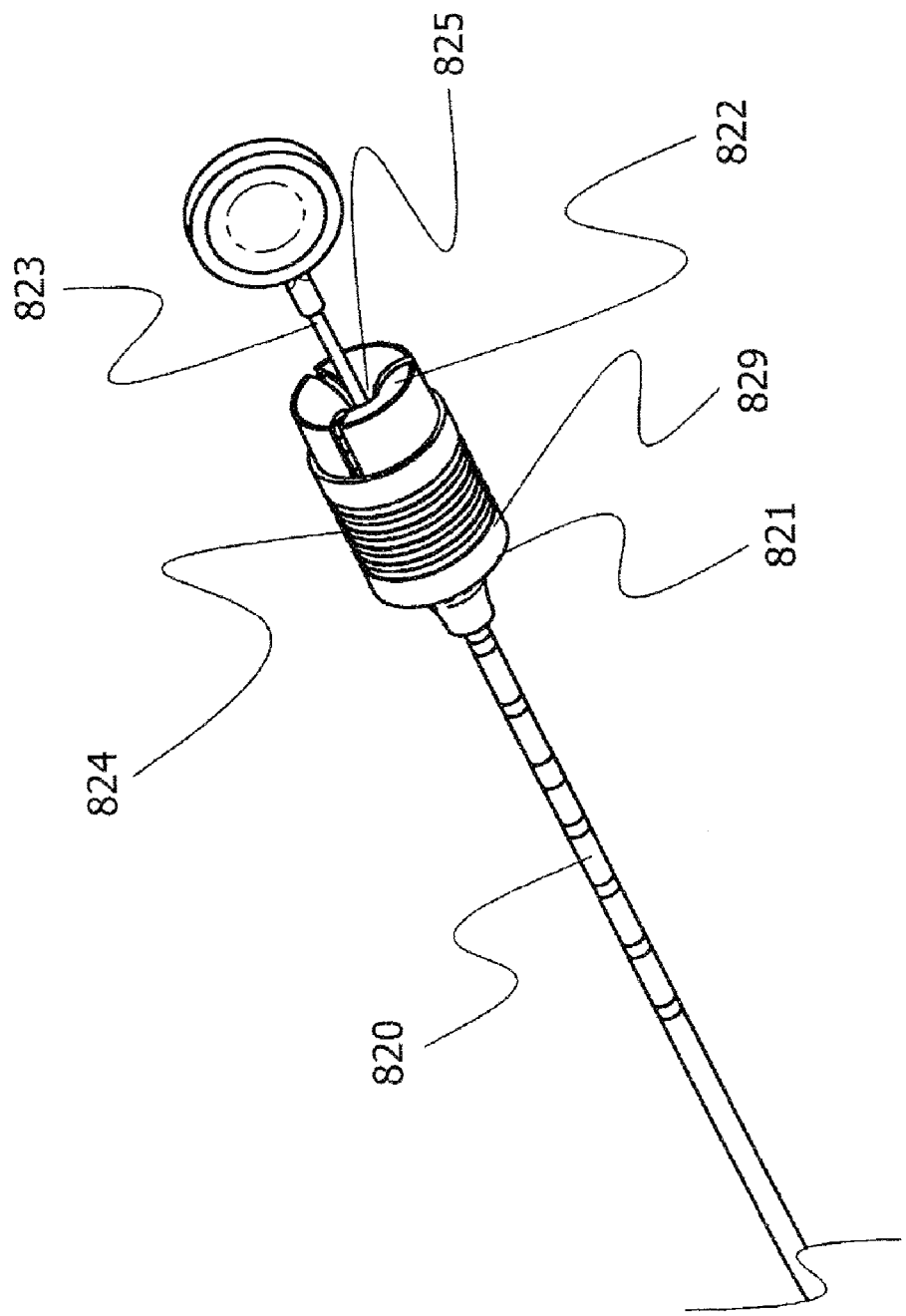
FIG. 52 is a perspective view of the safety shield having an obturator inserted.
Figure 53:
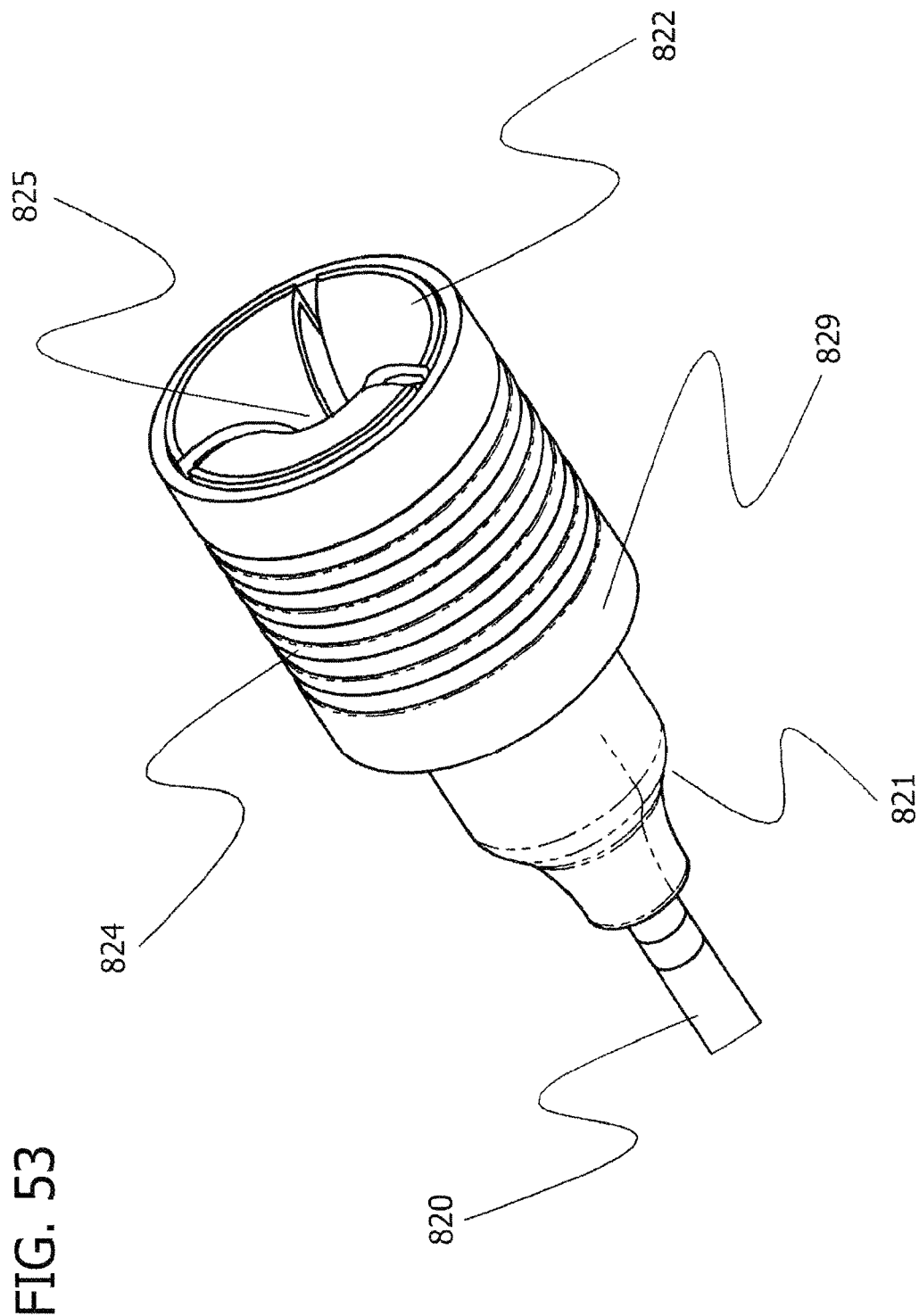
FIG. 53 is an enlarged perspective view of the safety shield having an adjustable guide.
Figure 54:
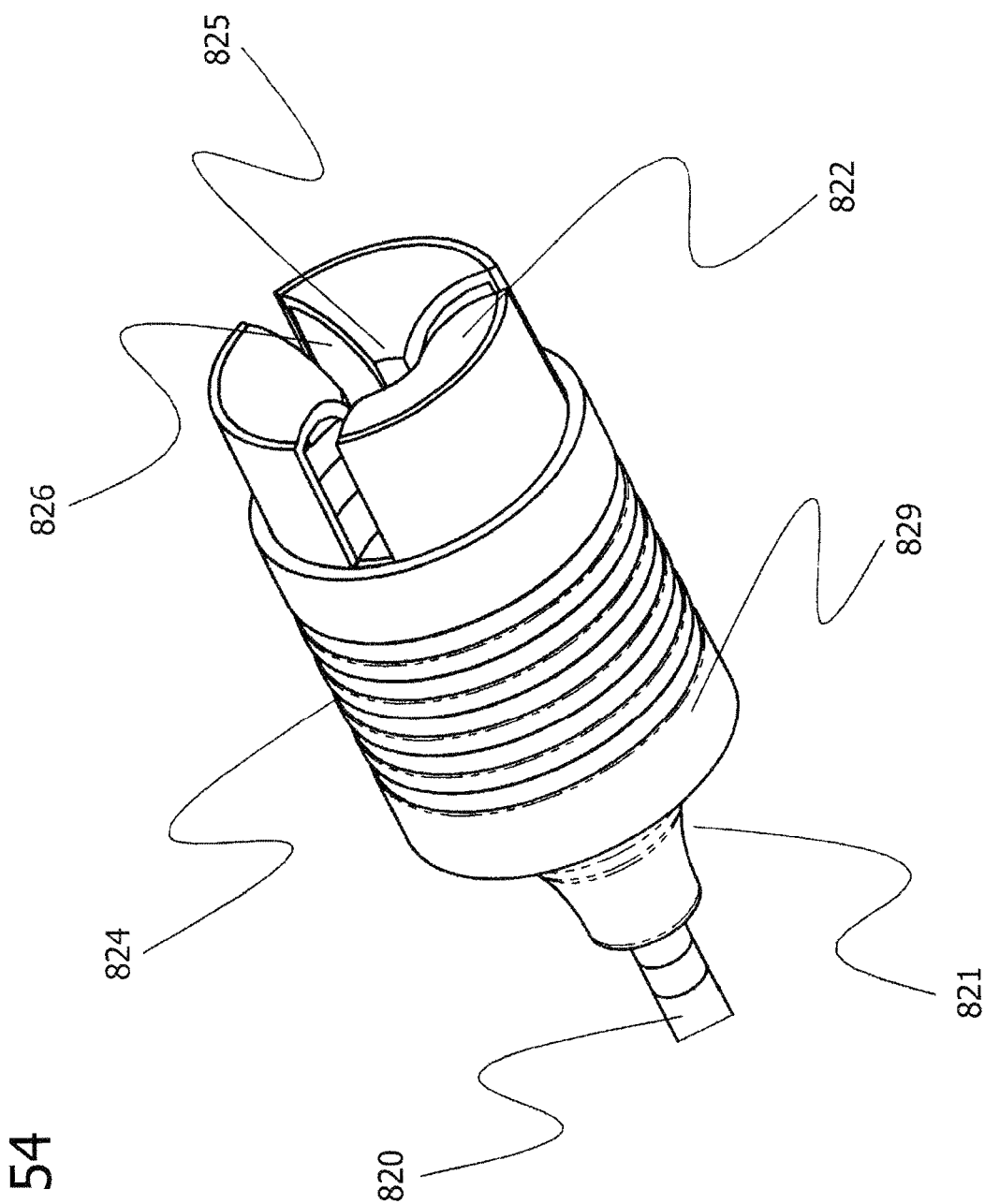
FIG. 54 is an enlarged perspective view of the safety shield having an adjustable guide with a reset area.

As shown in FIGS. 52-54, another embodiment includes a guiding member 822 having adjustable members 825 that can be positioned by a positioning member 829. The adjustable members 825 may be either rigid or flexible. The positioning member 829 may include, but is not limited to, a sleeve, button, lever, collar, or other member intended to interact with the adjustable members 825. The adjustable members 825 are configured such that the positioning member 829 interact with the adjustable members 825 causing the adjustable members 825 to be positioned so as to guide a through-the-needle device 823 (e.g., an obturator). The adjustable members 825 may be configured such that a tighter guiding member 822 may be obtained, than otherwise may fit around the needle 820. The positioning member 829 may contain grip surfaces 824. The grip surfaces 824 may be configured such that upon subsequent activation of the safety shield 821, the positioning member 829 will position the flexible members 825 upon activation. The positioning member 829 may also be configured such that the positioning member 829 may be repositioned wherein the adjustable members 825 provide a reset area 826.

Figure 55:
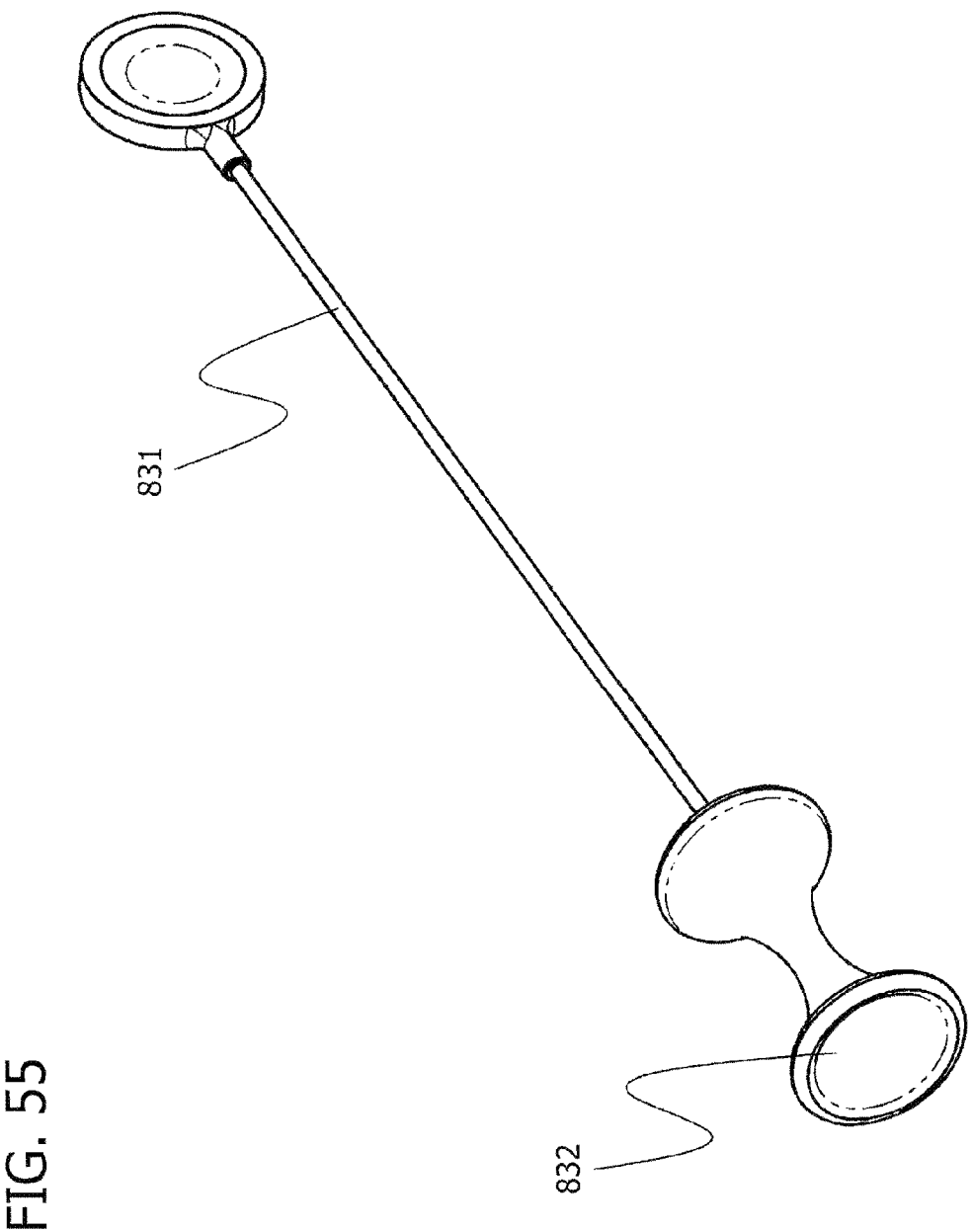
FIG. 55 is a guiding member integrated with an obturator.
Figure 56:
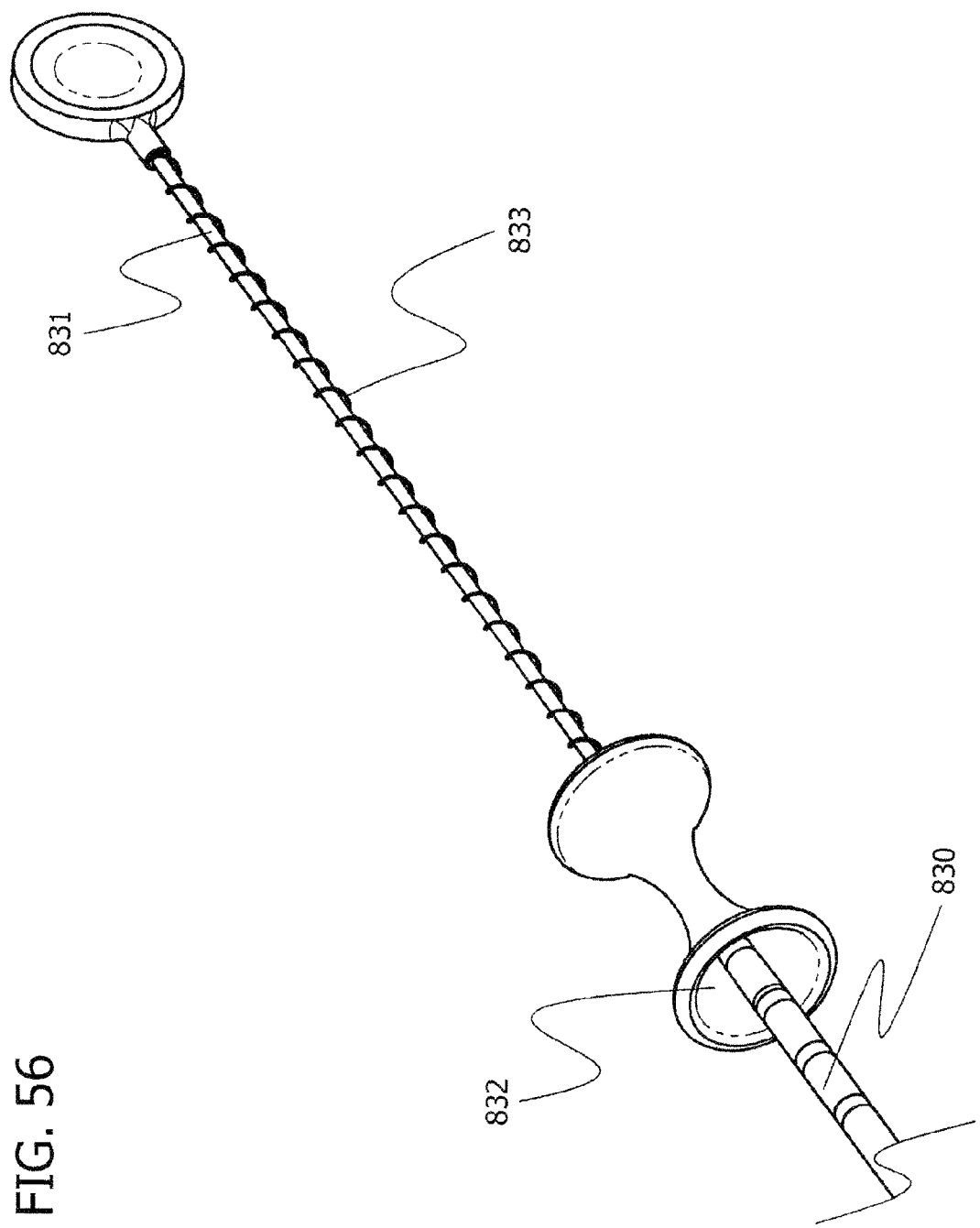
FIG. 56 is a guiding member integrated with an obturator having a spring.
Figure 57:
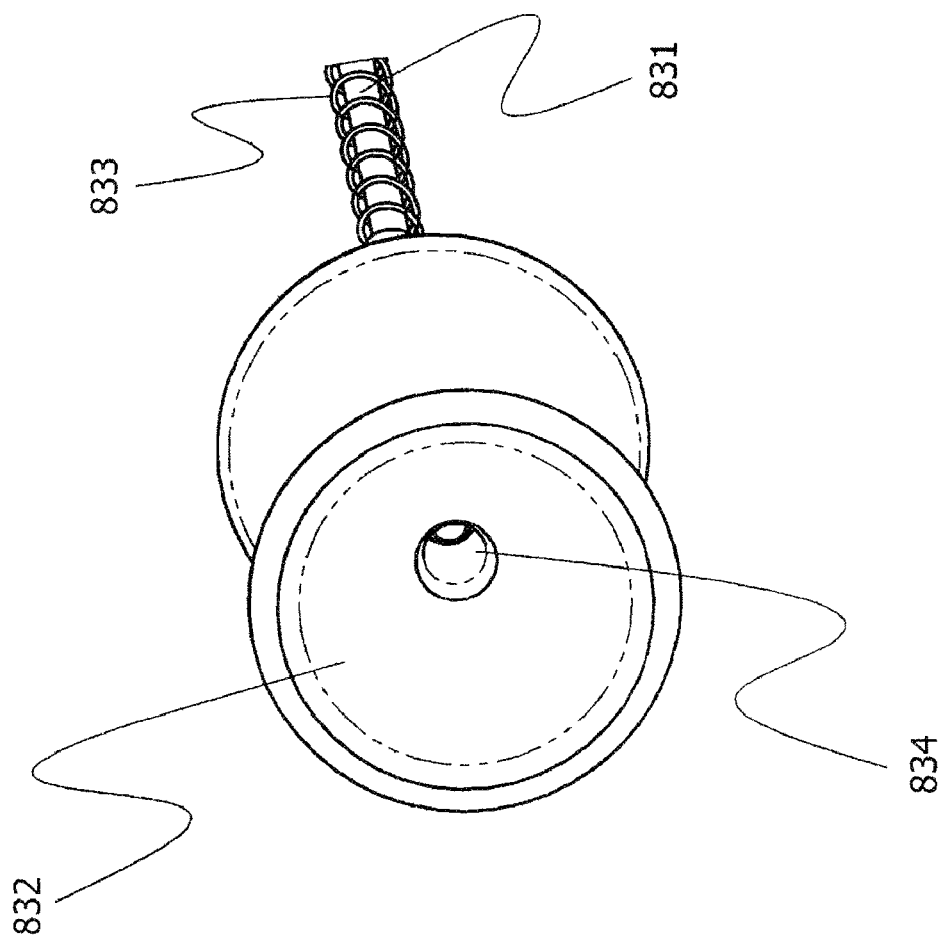
FIG. 57 is an enlarged view of the guiding member shown in FIG. 56.

As seen in FIGS. 55-57, another embodiment is illustrated wherein a guiding member 832 is integrated with the obturator 831. The guiding member 832 may be configured such that it remains attached to the obturator 831. The guiding member 832 may also be configured such that it is slidable along the obturator 831.

This embodiment depicts the guiding member 832 having a spring 833 (see FIGS. 56-57). The spring 833 may include, but is not limited to, a spring, folded plastic, telescoping features, line, wire, etc. It is configured such that the natural resting position of the guiding member 832 is at the end of the obturator 831. This allows for guiding of the obturator 831. The guiding member 832 is configured such that when the needle 830 is brought toward the obturator 831, the guiding member 832 guides the needle to the center. This guiding takes place with little resistance. When the needle 830 contacts the center of the guiding member 832, there are locking surfaces 834 configured such that the needle 830 tends to lock onto the guiding member 832, such as for example a luer taper. After the needle 830 is locked onto the guiding member 832, continued motion tends to make the guiding member 832 slide along the obturator 831. The obturator 831 is then guided into the needle 830 and expels the sample.

Figure 58:
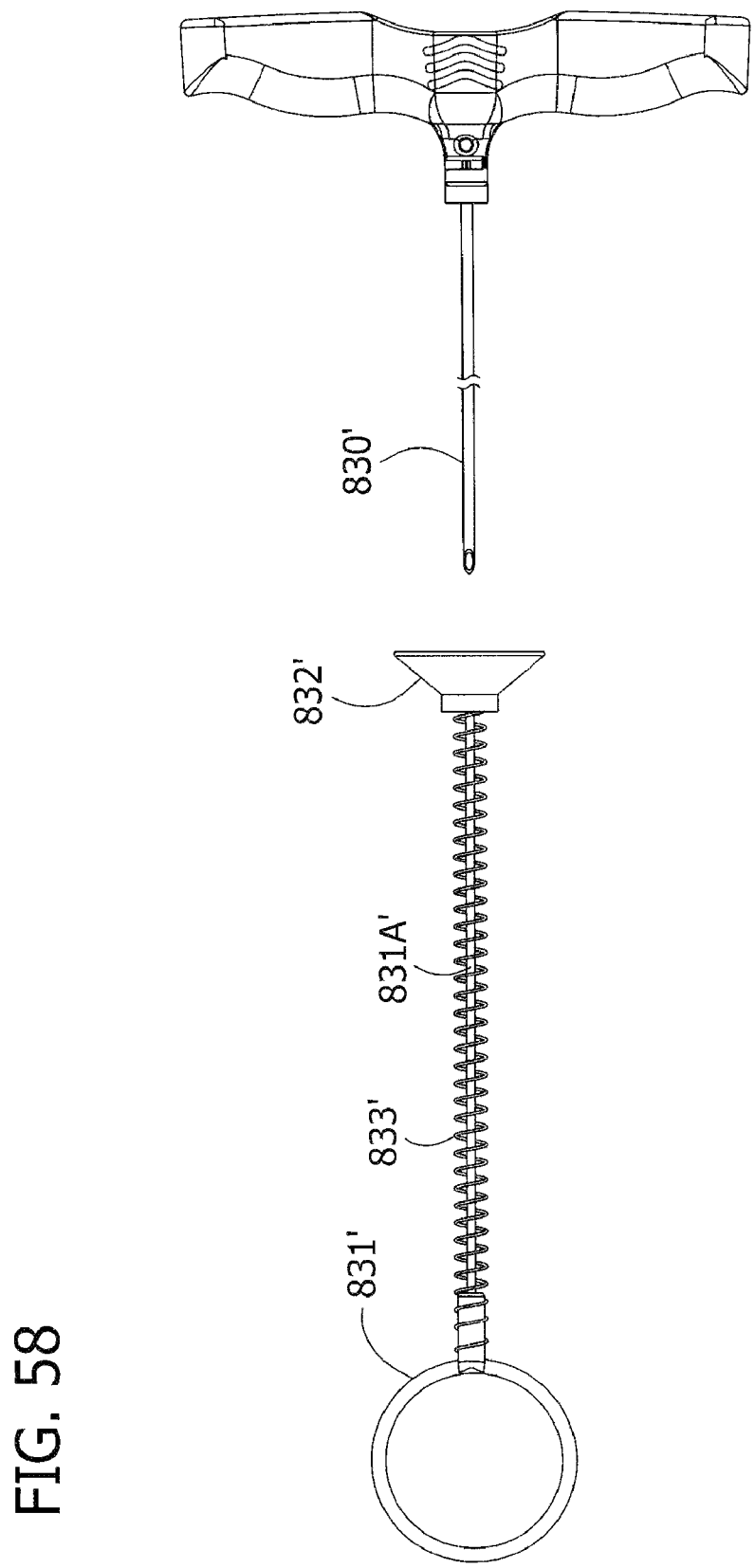
FIG. 58 is an elevation of a guiding member integrated with an obturator of another embodiment just prior to mating with a cannula.
Figure 59:
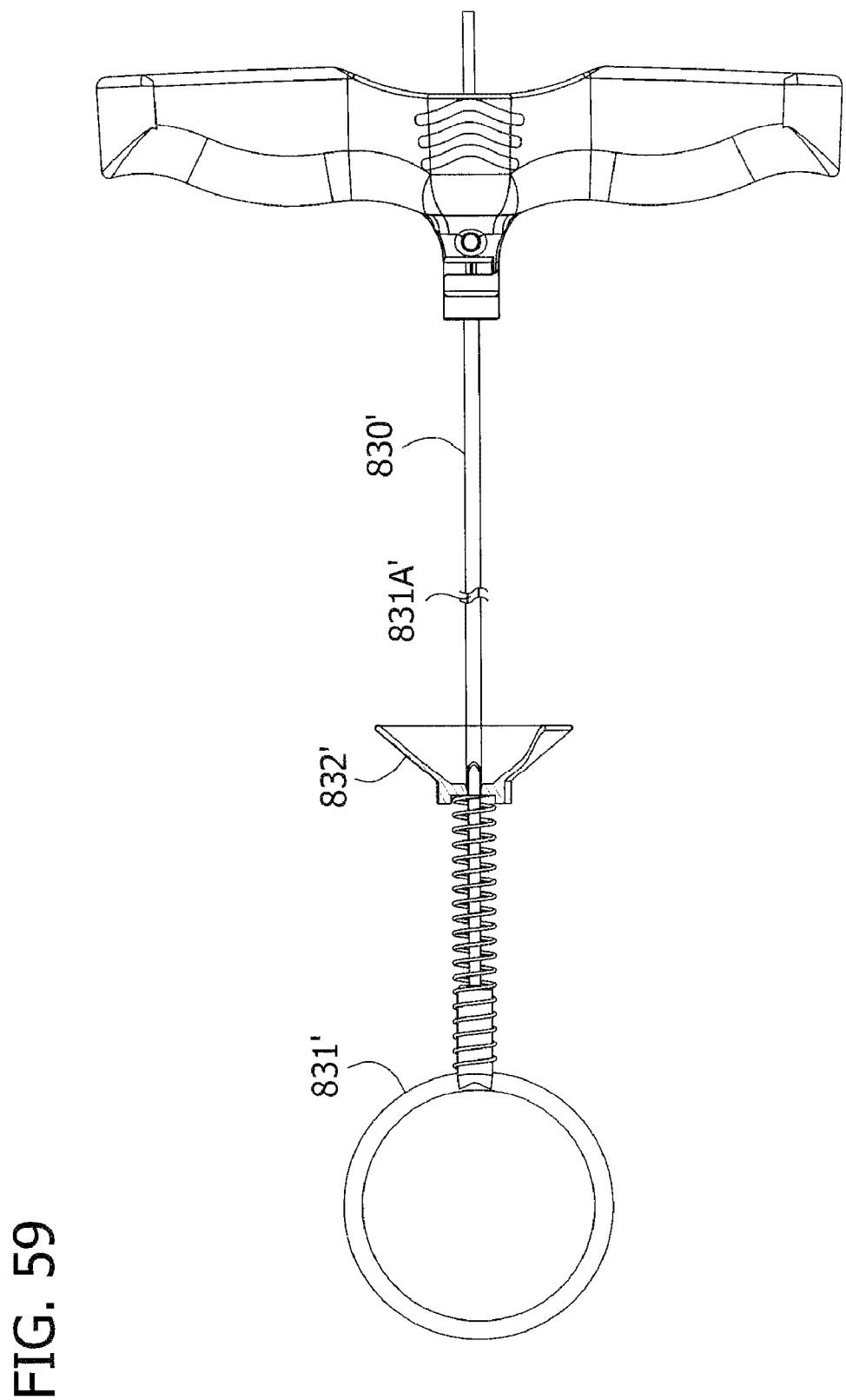
FIG. 59 is the elevation of FIG. 58 with the obturator inserted into the cannula.

In another embodiment shown in FIGS. 58 and 59, a shield 832' similar to the guiding member 832 is slidably secured to the obturator 831' so that the obturator can slide through the guiding member while compressing a spring 833'. The shield 832' substantially covers the sharpened end of the needle 830' to protect the user from an accidental stick. The spring 833' keeps the shield 832' in place on the end of the needle 830' throughout the operation of removing the sample illustrated schematically in FIGS. 58 and 59. The shield 832' may or may not have a guiding function for guiding the obturator 831' into the central passageway of the hollow needle 830'. The sharpened tip of the needle 830' is received in a tapered opening that also passes a shaft 831A' of the obturator 831' through the shield 832', but is blocked from passing through the shield by the size of the opening. The shaft 831A' of the obturator 831' will enter the central passageway of the needle 830' as the two parts are pushed further together (see, FIG. 59). However, the shield 832' remains in place, held by the sharpened end of the needle 830' and the bias of the spring 833'. As the obturator 831' is removed from the needle 830', the bias of the spring 833' keeps the shield 832' against the sharpened end of the needle so that the sharpened end is substantially covered at all times during the operation of removing the sample. Once the shaft 831A' of the obturator 831' is completely withdrawn from the needle 830', further separation will move the shield 832' off of the sharpened end of the needle so that the needle can be used again. Preferably, the shield 832' is retained on the obturator shaft 831A' at all times.

Figure 60:
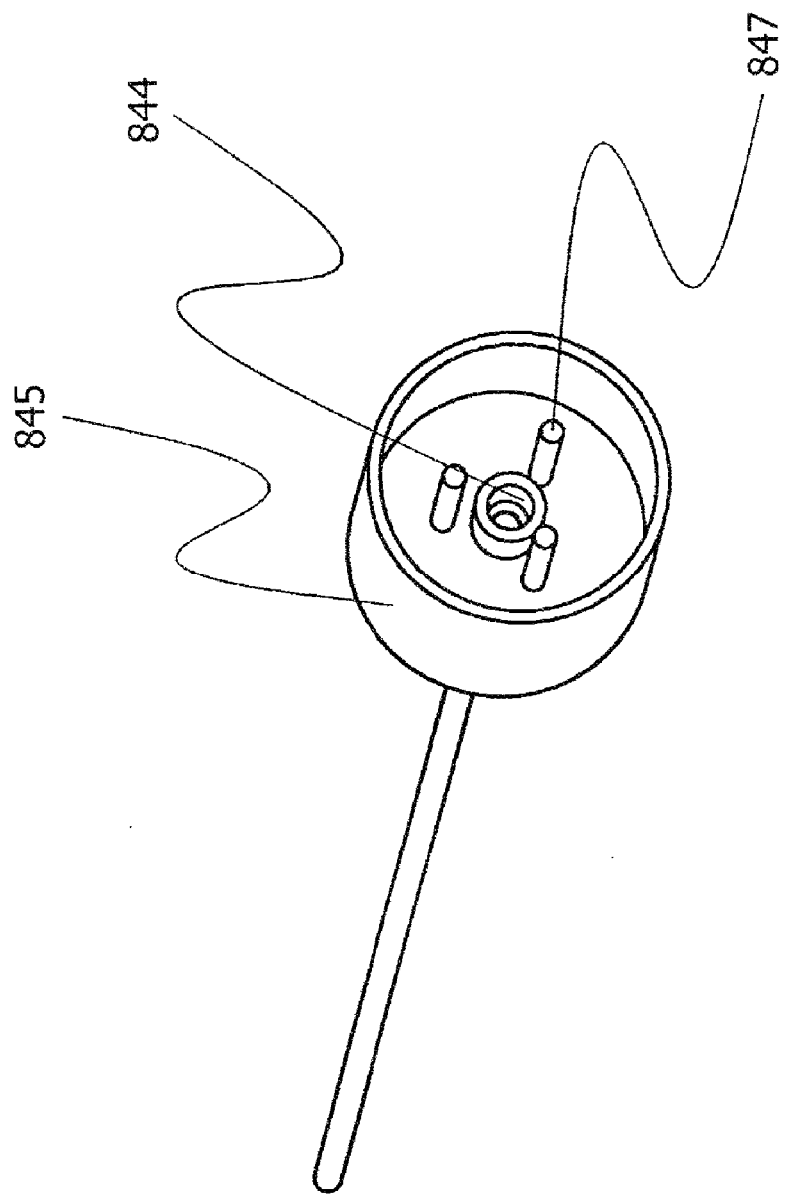
FIG. 60 is an obturator handle having a resettable feature.
Figure 61:
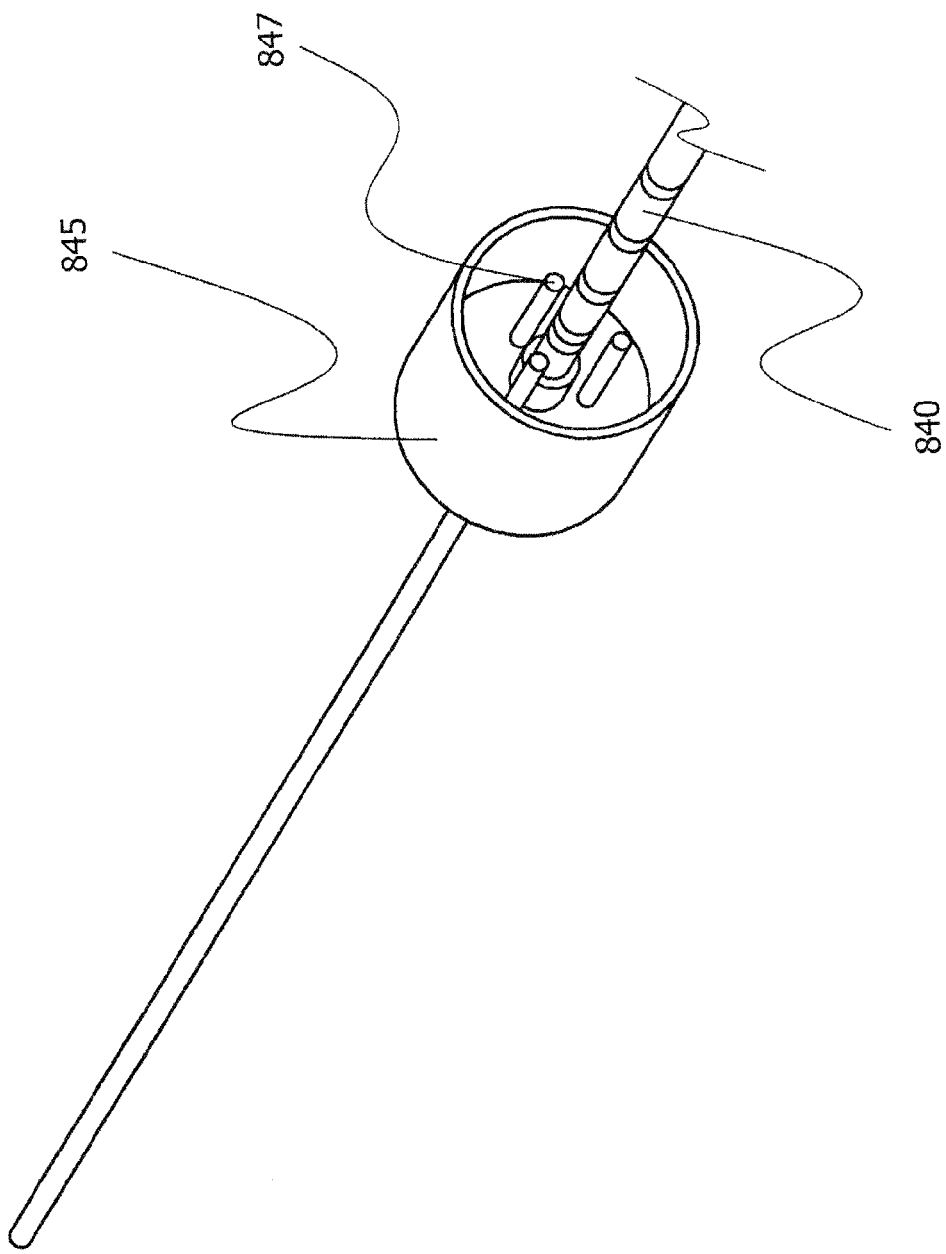
FIG. 61 is an obturator handle having a resettable feature.

As shown in FIGS. 60-61, the obturator grip or handle 845 may be configured such that reset geometry (or a "reset member") in the form of three pins 847 is integrated onto the obturator handle 845. The obturator handle 845 may also contain locking surfaces 844 configured such that the needle 840 tends to lock onto the obturator handle 845. The number of pins may be other than three within the scope of the present invention.

Figure 62:
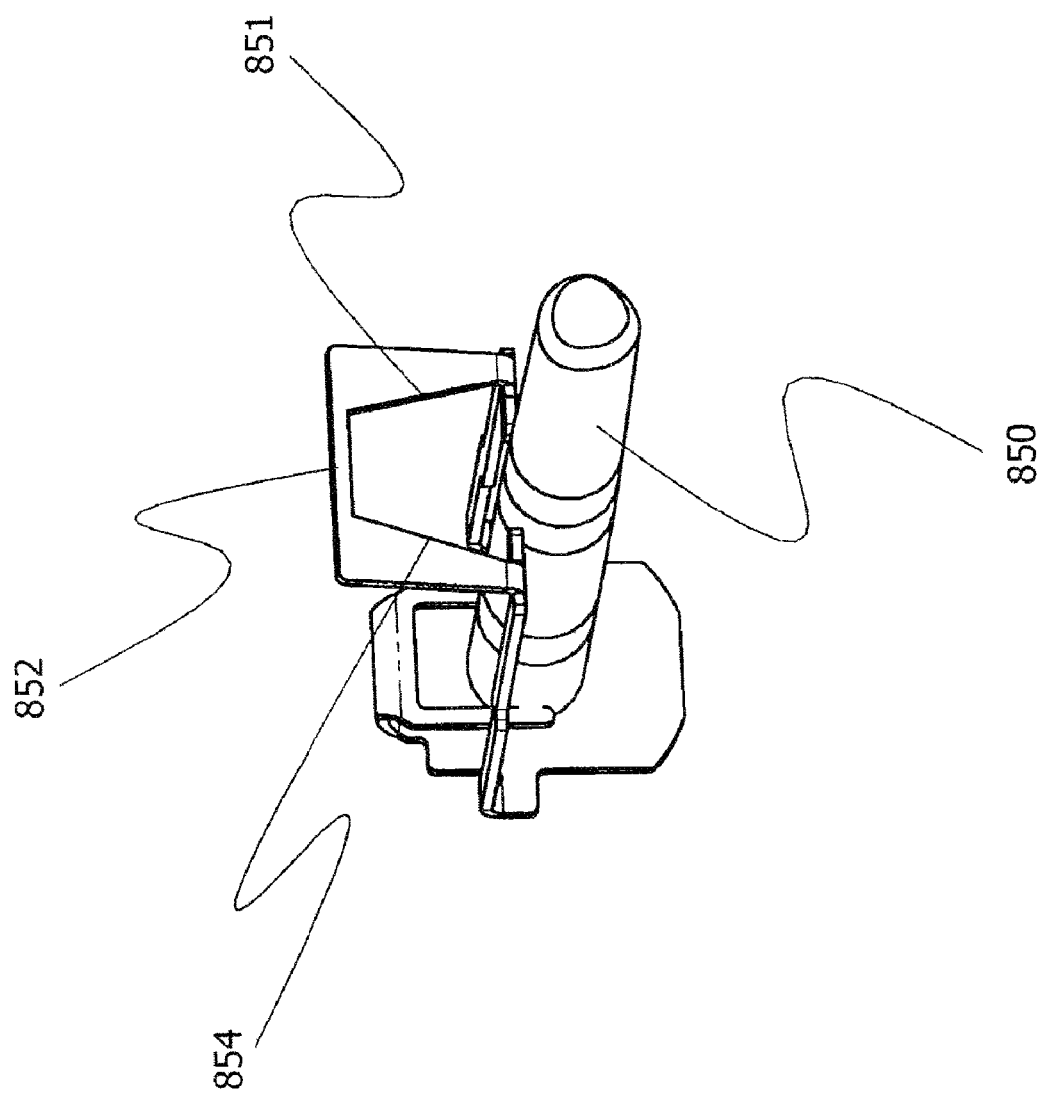
FIG. 62 is an obturator handle having a resettable feature inserted into a needle.

Other embodiments include modifications to the end sensing member 852 (see FIG. 62). The end sensing member 852 includes needle communicating surfaces 851 that rides on the needle 850 and provides a force to resist binding. When the geometry of the needle 850 changes (e. g., end of the needle, needle grind, needle taper, etc.), the end sensing member 852 senses the change of the needle 850 and binding is no longer resisted. Changing the needle 850 geometry includes, but is not limited to, angled surfaces, notched surfaces, bumps, or any surface intended to amplify end sensing. Angled surfaces 854 are shown in FIG. 62. The angled surfaces 854 are configured such that a slight needle 850 geometry change causes the angled surfaces 854 to translate dramatically. This is due to the geometry condition that exists from the angled surfaces 854.

Figure 63:
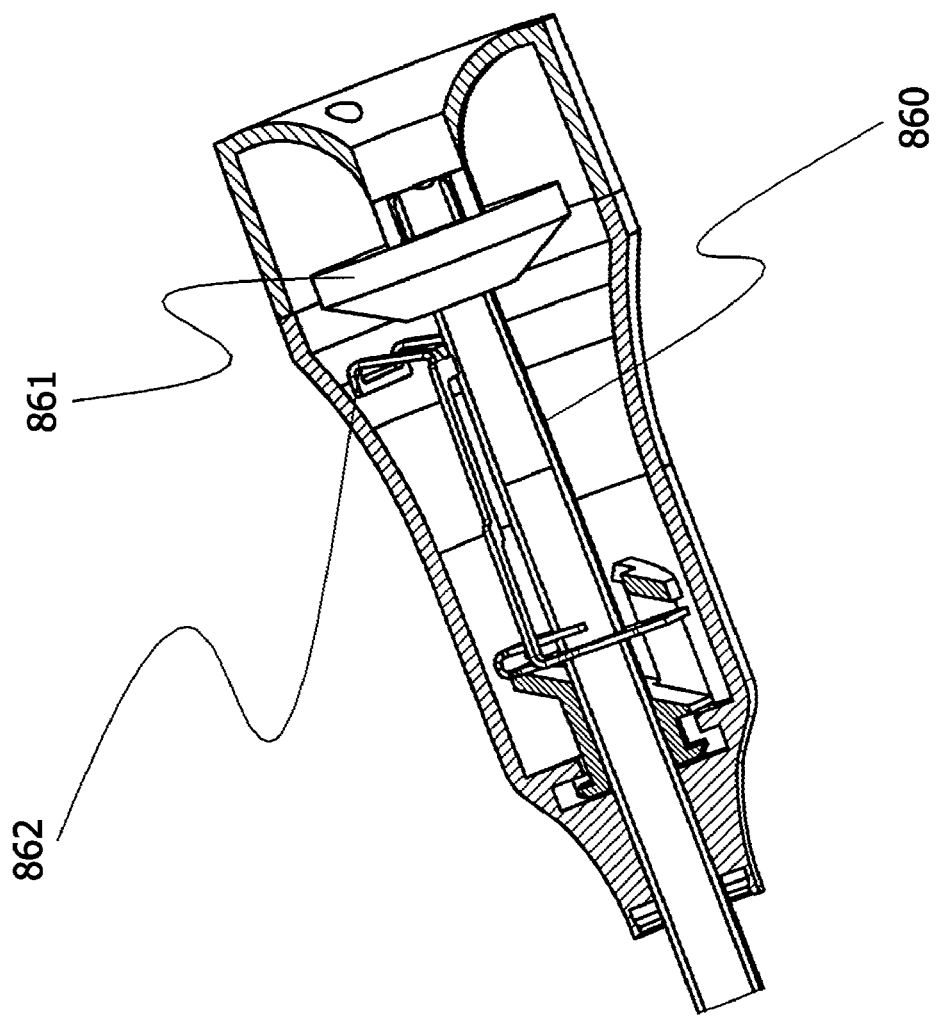
FIG. 63 is an alternative embodiment of the medical needle shield apparatus according to the present disclosure.

Another embodiment is shown in FIG. 63 having a separate needle communicating surface 861. This needle communicating surface 861 applies a frictional force to the needle 860. This force is used in combination with needle communicating members 862 to oppose binding. The frictional force that opposes binding on the needle 860 is available for geometry changes in the needle 860 that prevent the friction forces from being applied (e. g., needle taper, needle grind, end of the needle, etc.).

Figure 64:
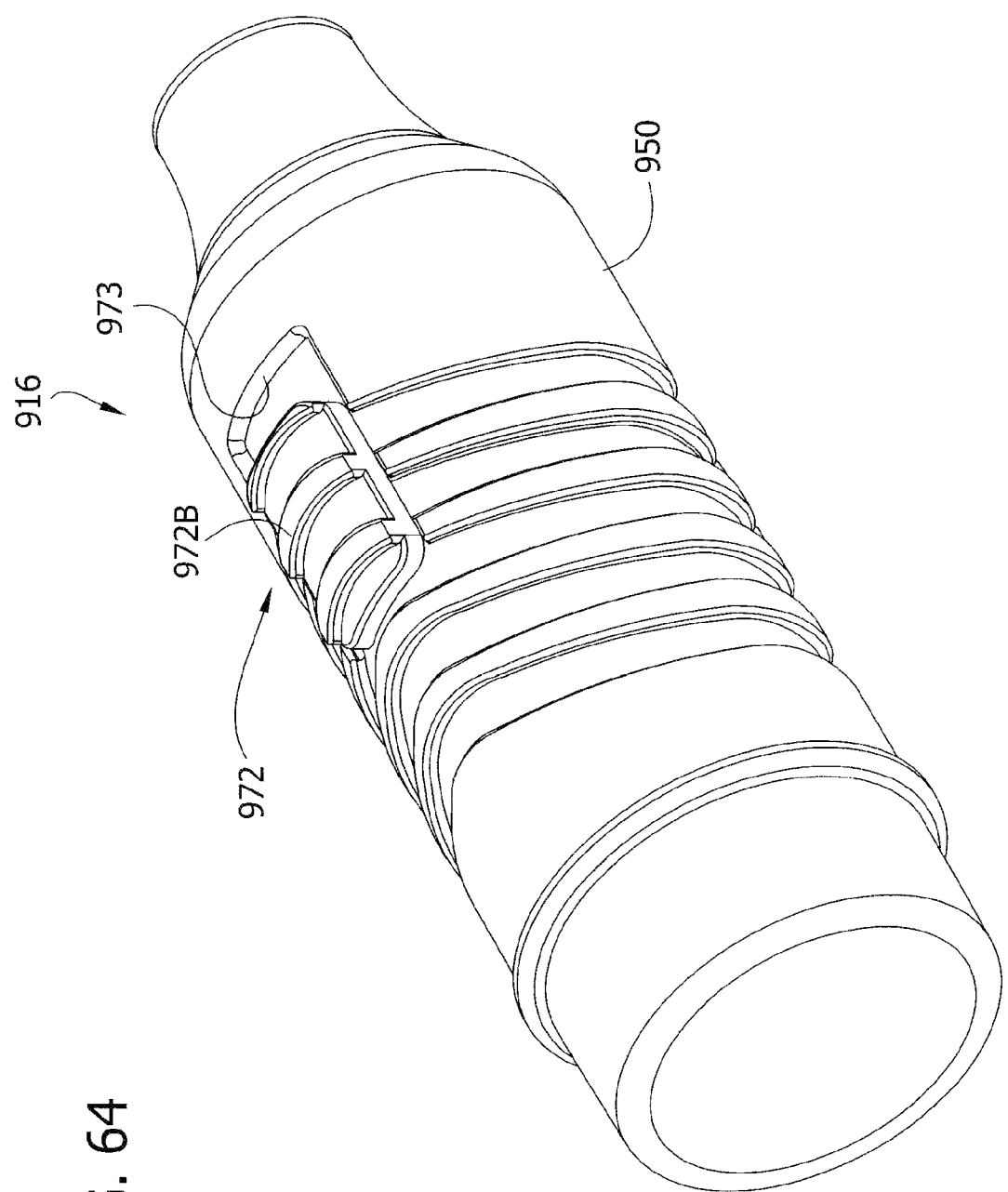
FIG. 64 is a safety shield incorporating a reset member.
Figure 65:
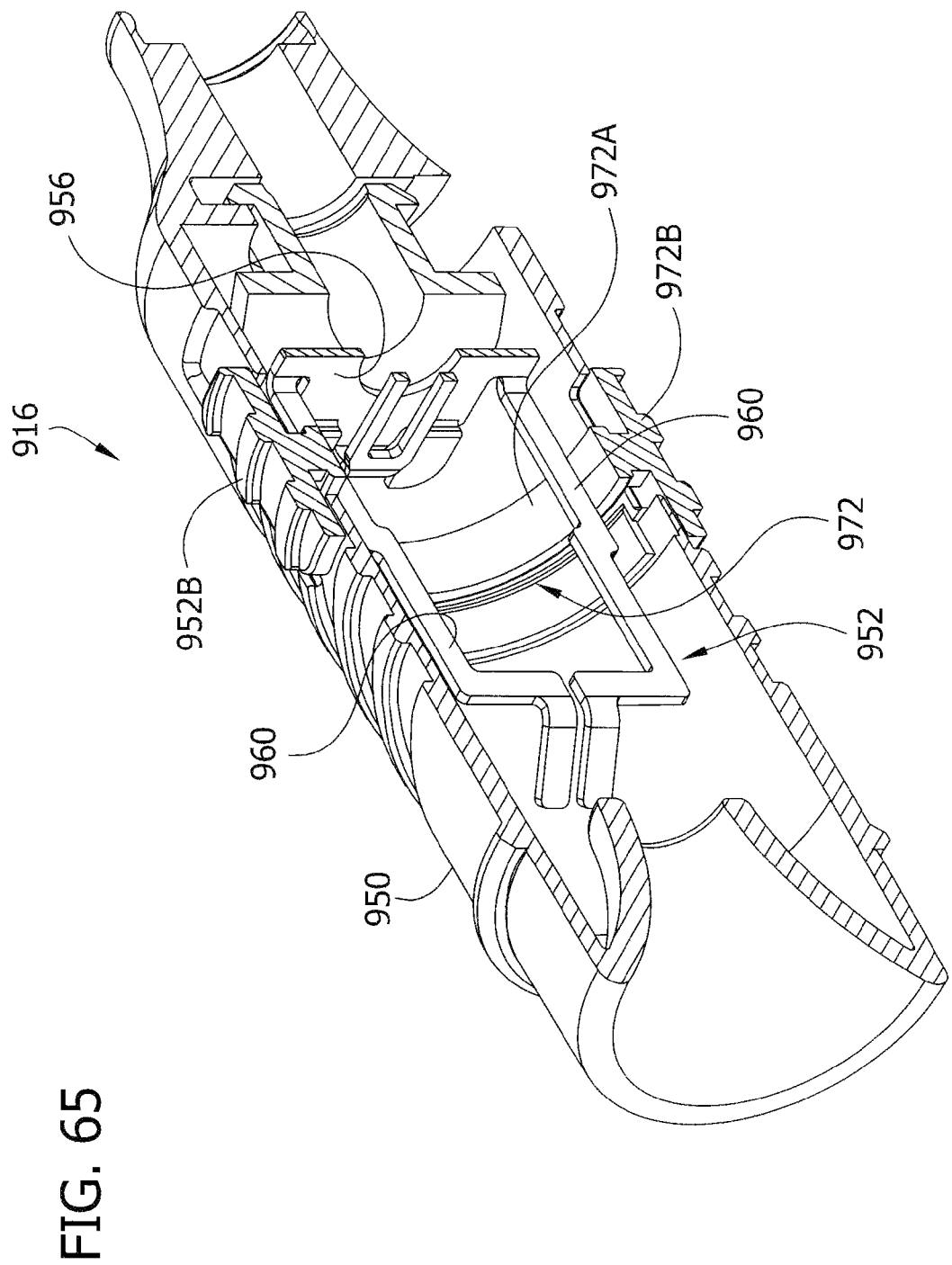
FIG. 65 is a longitudinal section of the safety shield.

Referring now to FIGS. 64 and 65, a safety shield 916 of a needle assembly is shown to comprise a tubular housing 950 containing a locking mechanism 952 substantially similar to the locking mechanisms (52, etc.) described above. The safety shield 916 can be used with needle assemblies as shown and described previously herein. In the embodiment of FIGS. 64 and 65, a reset member 972 comprises an annular engaging portion 972A and a pair of slides 972B (broadly, "actuating members"). The engaging portion 972A is located inside the tubular housing 950 and the slides 972B are located on the exterior of the housing. The connection of the engaging portion 972A with the slides 972B occurs through respective slots 973 in the tubular housing. Moving the slides 972B in a direction that is generally parallel to the outer surface of the tubular housing 950 toward the proximal end of the tubular housing moves the engaging portion 972A into engagement with a base 956 of the locking mechanism 952. The engaging portion 972A can push the base 956 so that the locking mechanism 952 releases its lock on the needle (not shown), allowing the safety shield 916 to be moved away from a sharpened end of the needle so that the needle can be reused. As described for earlier embodiments, in the release position the locking mechanism base 956 is more nearly perpendicular to the longitudinal axis of the needle and arms 960 of the locking mechanism are more nearly parallel to the longitudinal axis of the needle. The reset member 972 can be biased in a direction out of engagement with the locking mechanism 952 so that it does not interfere with normal operation of the locking mechanism.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "up", "down", "top" and "bottom" and variations of these terms is made for convenience, but does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A needle assembly comprising:
    mounting structure;
    a needle mounted on the mounting structure and extending outwardly therefrom, the needle having a longitudinal axis, a sharp end and a central axial passageway;
    a safety shield associated with the needle and comprising a tubular housing having an open end, the tubular housing being adapted for movement relative to the needle between a stowed position in which the tubular housing is spaced from the sharp end of the needle and a deployed position in which the tubular housing covers the sharp end, and a locking mechanism adapted to releasably lock the tubular housing in position covering the sharp end of the needle; and
    a reset member selectively operatively engageable with the locking mechanism of the safety shield for releasing the locking mechanism to permit the tubular housing to be moved away from the sharp end of the needle;

the safety shield further comprising a resilient membrane substantially covering the open end of the tubular housing, the membrane comprising a thin sheet of resilient material extending in a plane across the tubular housing, the membrane being resiliently deformable upon engagement with the reset member to permit the reset member to move into operative engagement with the locking mechanism for releasing the locking mechanism;

wherein the membrane is generally annular and has a central opening generally in alignment with the central axial passageway of the needle, the central opening having a diameter less than a diameter of the reset member, the membrane being adapted to stretch to enlarge the central opening upon engagement with the reset member for passage of the reset member into the tubular housing to engage the locking mechanism.

2. A needle assembly as set forth in claim 1 further comprising an obturator including a shaft adapted to be received through the central opening of the membrane for guiding the shaft into the central axial passageway of the needle.

3. A needle assembly as set forth in claim 1 wherein the reset member is supported by the obturator shaft.

4. A needle assembly comprising:
mounting structure;
a needle mounted on the mounting structure and extending outwardly therefrom, the needle having a longitudinal axis, a sharp end and a central axial passageway;
a safety shield associated with the needle and comprising a tubular housing, the tubular housing being adapted for movement relative to the needle between a stowed position in which the tubular housing is spaced from the sharp end of the needle and a deployed position in which the tubular housing covers the sharp end, and a locking mechanism adapted to releasably lock the tubular housing in position covering the sharp end of the needle; and
a reset member supported on the safety shield for sliding movement relative to the safety shield generally parallel to an outer surface of the safety shield, the reset member being selectively operatively engageable with the locking mechanism of the safety shield for releasing the locking mechanism to permit the tubular housing to be moved away from the sharp end of the needle, wherein the reset member further comprises an actuating portion located on an outer surface of the safety shield, the actuating potion comprising a slide configured to slide relative to the housing of the safety shield to engage the reset member with the locking member.

5. A needle assembly as set forth in claim 4 wherein the reset member includes an engaging portion disposed in the safety shield and capable of engaging the locking mechanism to release the locking mechanism.

6. A needle assembly as set forth in claim 5 wherein the engaging portion is annular in shape and generally coaxial with the longitudinal axis of the needle.

* * * * *